(12) United States Patent
Rajasekaran et al.

(10) Patent No.: US 10,900,964 B2
(45) Date of Patent: Jan. 26, 2021

(54) PEPTIDE MICROARRAYS AND NOVEL BIOMARKERS FOR CELIAC DISEASE

(71) Applicant: VIBRANT HOLDINGS, LLC, San Carlos, CA (US)

(72) Inventors: John J. Rajasekaran, Hillsborough, CA (US); Vasanth Jayaraman, San Mateo, CA (US); Kang Bei, San Mateo, CA (US); Tianhao Wang, San Mateo, CA (US); Karthik Krishna, Foster City, CA (US); Hari Krishnan Krishnamurthy, San Mateo, CA (US)

(73) Assignee: VIBRANT HOLDINGS, LLC, San Carlos, CA (US)

( * ) Notice: Subject to any disclaimer, the term of this patent is extended or adjusted under 35 U.S.C. 154(b) by 332 days.

(21) Appl. No.: 15/510,223

(22) PCT Filed: Sep. 10, 2015

(86) PCT No.: PCT/US2015/049528
§ 371 (c)(1),
(2) Date: Mar. 9, 2017

(87) PCT Pub. No.: WO2016/040703
PCT Pub. Date: Mar. 17, 2016

(65) Prior Publication Data
US 2017/0269077 A1 Sep. 21, 2017

Related U.S. Application Data

(60) Provisional application No. 62/048,537, filed on Sep. 10, 2014.

(51) Int. Cl.
*G01N 33/564* (2006.01)
*C07K 7/08* (2006.01)
(Continued)

(52) U.S. Cl.
CPC .......... *G01N 33/564* (2013.01); *A61K 38/10* (2013.01); *A61K 39/00* (2013.01); *C07K 7/08* (2013.01);
(Continued)

(58) Field of Classification Search
CPC .......... A61K 38/10; A61K 39/00; C07K 7/08; C40B 40/10; G01N 33/564;
(Continued)

(56) References Cited

U.S. PATENT DOCUMENTS

2002/0076834 A1 6/2002 Detlef et al.
2002/0086319 A1 7/2002 Ellson et al.
(Continued)

FOREIGN PATENT DOCUMENTS

CN 103675291 3/2014
WO WO 98/03872 A2 1/1998
(Continued)

OTHER PUBLICATIONS

Robinson et al. (Proc. Natl. Acad. Sci., 1998, 95:5929-5934) (Year: 1998).*

(Continued)

*Primary Examiner* — Jeremy C Flinders
(74) *Attorney, Agent, or Firm* — Goodwin Procter LLP

(57) ABSTRACT

The present disclosure relates generally to biomarkers and peptide arrays, and, more particularly, to a method of using a peptide array to identify biomarkers for an autoimmune disease such as, e.g., celiac disease. Furthermore, a set of novel biomarkers for celiac disease, having high sensitivity and specificity, are disclosed in addition to method of treatment using the novel biomarkers.

9 Claims, 17 Drawing Sheets

Specification includes a Sequence Listing.

(51) Int. Cl.
  *C40B 40/10* (2006.01)
  *A61K 39/00* (2006.01)
  *A61K 38/10* (2006.01)
  *G01N 33/68* (2006.01)

(52) U.S. Cl.
  CPC .......... *C40B 40/10* (2013.01); *G01N 33/6854* (2013.01); *G01N 33/6878* (2013.01); *G01N 2800/02* (2013.01); *G01N 2800/24* (2013.01)

(58) Field of Classification Search
  CPC ........... G01N 33/6854; G01N 33/6878; G01N 2800/02; G01N 2800/24
  See application file for complete search history.

(56) References Cited

U.S. PATENT DOCUMENTS

| | | |
|---|---|---|
| 2003/0148401 A1 | 8/2003 | Agrawal et al. |
| 2003/0228605 A1 | 12/2003 | Sloostra et al. |
| 2004/0027093 A1 | 2/2004 | Tashiro et al. |
| 2005/0240811 A1 | 10/2005 | Safford et al. |
| 2011/0190210 A1 | 8/2011 | Adini et al. |
| 2011/0293644 A1 | 12/2011 | Anderson et al. |
| 2012/0172309 A1 | 7/2012 | Dal Farra et al. |
| 2016/0040703 A1 | 2/2016 | Schnaufer et al. |

FOREIGN PATENT DOCUMENTS

| | | | | |
|---|---|---|---|---|
| WO | WO 2003/104273 A2 | 12/2003 | | |
| WO | WO 2010/060155 A1 | 6/2010 | | |
| WO | WO 2011/027048 A1 | 3/2011 | | |
| WO | WO 2013/119845 A1 | 8/2013 | | |
| WO | WO-2013119845 A1 * | 8/2013 | ....... | G01N 33/54353 |
| WO | 2016040703 A1 | 3/2016 | | |

OTHER PUBLICATIONS

Dai et al. (Clinical and Vaccine Immunology, 2012, pp. 338-342) (Year: 2012).*
da Silveira et al. (Trends in Parasitology, 2001, 17(6):286-291) (Year: 2001).*
Ripalti et al. (Journal of Clinical Microbiology, 1994, pp. 358-363) (Year: 1994).*
Van der Wal et al. (Proc. Natl. Acad. Sci. USA, 1998, 95:10050-10054) (Year: 1998).*
PCT Invitation to Pay Additional Fees, PCT Application No. PCT/US15/49528, Nov. 20, 2015, 3 pages.
PCT International Search Report and Written Opinion, PCT Application No. PCT/US15/49528, dated Feb. 1, 2016, 18 pages.
Australian First Examination Report, Australian Application No. 2015314934, dated Feb. 13, 2018, 3 pages.
European Partial Supplementary Search Report, European Application No. 15839169.8, dated Mar. 12, 2018, 20 pages.
Choung, R.S. et al., "Determination of B-Cell Epitopes in Patients with Celiac Disease: Peptide Microarrays," PLOS One, Jan. 29, 2016, e0147777, pp. 1-16, vol. 11, No. 1.
Beyer, M. et al., "Combinatorial Synthesis of Peptide Arrays onto a Microchip," Science, vol. 318, Dec. 21, 2007, p. 1888.
Beyer, M. et al., "Supporting Online Material for Combinatorial Synthesis of Peptide Arrays onto a Microchip," Science, vol. 318, Dec. 21, 2007, six pages.
Piehler, J. et al., "Protein Interactions in Covalently Attached Dextran Layers," Colloid and Surfaces B: Biointerfaces 13 (1999), pp. 325-336.
United States Office Action, U.S. Appl. No. 14/941,404, dated May 30, 2018, ten pages.
New Zealand First Examination Report, New Zealand Application No. 730519, dated Oct. 25, 2017, 6 pages.
Ballew, J.T., "Antibody Biomarker Discovery Through in Vitro Directed Evolution of Consensus Recognition Epitopes," Proceedings of the National Academy of Sciences of the United States of America, Nov. 26, 2013, pp. 19330-19335, vol. 110, No. 48.
Buus, S. et al., "High-Resolution Mapping of Linear Antibody Epitopes Using Ultrahigh-Density Peptide Microarrays," Molecular & Cellular Proteomics, Dec. 2012, pp. 1790-1800, vol. 11, No. 12.
PCT International Preliminary Report on Patentability, International Application No. PCT/US2015/049528, Sep. 27, 2016, 13 pages.
Robinson Optimizing the stability of single-chain proteins by linker length and composition mutagenesis Proc. Natl. Acad. Sci., 1998, 95:5929-5934.
Dai et al., Evaluation of a recombinant multiepitope peptide for serodiagnosis of Toxoplasma gondii infection, Clinical and Vaccine Immunology, 2012, pp. 338-342).
Da Silveira et al., Chagas disease: recombinant Trypanosoma cruzi antigens for serological diagnosis, Trends in Parasitology, 2001, 17(6):286-291.
Ripalti et al., Construction of Polyepitope fusion antigens of human cytomegalovirus ppUL32: Rectivity with human antibodies, Journal of Clinical Microbiology, 1994, pp. 358-363.
Choung et al. "Determination of B-cell epitopes in patients with celiac disease: peptide microarrays." PLoS One 11, No. 1 (2016): e0147777, 16 pages.

* cited by examiner

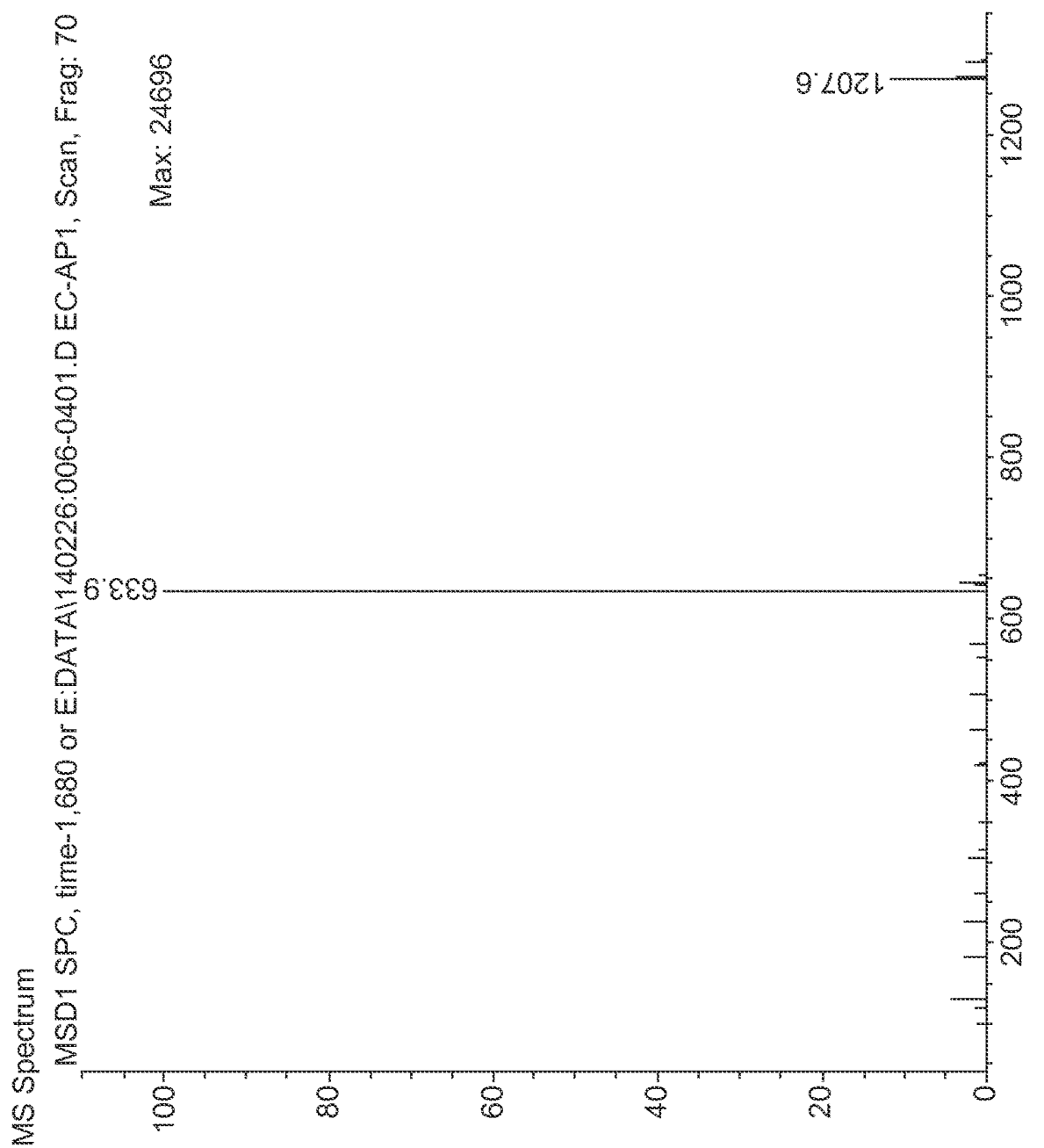

| | QPE% | PEQ% | EQP% | QPF% | FPE% | PFP% | FPQ% | PQP% | PQQ% |
|---|---|---|---|---|---|---|---|---|---|
| %QPE% | 9% | 7% | 8% | 14% | 3% | 12% | 3% | 0% | 0% |
| %PEQ% | 21% | 27% | 21% | 24% | 1% | 10% | 12% | 1% | 12% |
| %EQP% | 11% | 16% | 25% | 22% | 1% | 18% | 10% | 10% | 4% |
| %QPF% | 44% | 5% | 12% | 9% | 1% | 7% | 8% | 7% | 1% |
| %FPE% | 20% | 22% | 19% | 0% | 0% | 0% | 0% | 0% | 8% |
| %PFP% | 34% | 37% | 8% | 5% | 0% | 4% | 5% | 5% | 5% |
| %FPQ% | 21% | 28% | 17% | 2% | 0% | 3% | 5% | 4% | 2% |
| %PQP% | 6% | 14% | 7% | 9% | 0% | 2% | 1% | 1% | 0% |
| %PQQ% | 13% | 17% | 7% | 3% | 0% | 1% | 3% | 0% | 5% |

FIG. 6A

|        | QPE% | PEQ% | EQP% | QPF% | FPE% | PFP% | FPQ% | PQP% | PQQ% |
|--------|------|------|------|------|------|------|------|------|------|
| %QPE%  | 7%   | 6%   | 14%  | 23%  | 7%   | 25%  | 2%   | 2%   | 0%   |
| %PEQ%  | 17%  | 27%  | 24%  | 31%  | 5%   | 22%  | 20%  | 2%   | 14%  |
| %EQP%  | 9%   | 19%  | 31%  | 28%  | 5%   | 29%  | 18%  | 23%  | 5%   |
| %QPF%  | 61%  | 10%  | 19%  | 15%  | 3%   | 17%  | 15%  | 20%  | 4%   |
| %FPE%  | 17%  | 17%  | 18%  | 0%   | 0%   | 0%   | 1%   | 0%   | 13%  |
| %PFP%  | 48%  | 52%  | 13%  | 8%   | 1%   | 9%   | 10%  | 15%  | 7%   |
| %FPQ%  | 21%  | 25%  | 25%  | 2%   | 0%   | 3%   | 3%   | 5%   | 2%   |
| %PQP%  | 6%   | 8%   | 11%  | 16%  | 0%   | 2%   | 0%   | 0%   | 0%   |
| %PQQ%  | 6%   | 9%   | 5%   | 3%   | 0%   | 1%   | 2%   | 0%   | 3%   |

FIG. 6B

PEPTIDE MICROARRAYS AND NOVEL BIOMARKERS FOR CELIAC DISEASE

CROSS-REFERENCE TO RELATED APPLICATIONS

This application is the National Stage of International Application No. PCT/US2015/049528, filed Sep. 10, 2015, which claims the benefit of U.S. Provisional Patent Application No. 62/048,537, filed Sep. 10, 2014, the disclosure of which is incorporated herein by reference.

SEQUENCE LISTING

The instant application contains a Sequence Listing which has been submitted via EFS-Web and is hereby incorporated by reference in its entirety. Said ASCII copy, created on Mar. 9, 2017, is named 30699 US_Sequence_Listing.txt, and is 32,789 bytes in size.

BACKGROUND

The development of accurate, inexpensive, and high fidelity tools for biomarker discovery for routine diagnostic assays to detect the presence of an autoimmune disease is crucial to meet the clinical needs of early detection of disease for developing a preventative strategy. Detection of antibodies correlated with an autoimmune disease through binding to the biomarkers is one of the main approaches for the diagnosis of many diseases, including autoimmune disorders, infectious diseases, and cancers.[1-3] Indeed, the development of antibody-based diagnostic assays has been intensively pursued for the diagnosis and treatment of disease, however only a small number of biomarkers have been identified as effective disease markers.[1,4] There are many challenges to the development of biomarkers, such as heterogeneity of antibodies, variability of host responses, and reagents among others. However, improved methods of discovery of biomarkers and improved biomarkers for diagnosis and treatment of disease are needed to better identify and treat patient populations.

One such autoimmune disease is celiac disease. Celiac disease, also known as coeliac disease or celiac sprue (coeliac sprue), affects approximately 1% of people in Europe and North America. In many of those affected, celiac disease is unrecognised, but this clinical oversight is now being rectified with greater clinical awareness. A gluten free diet is the only current treatment for celiac disease, and because regular ingestion of as little as 50 mg of gluten (equivalent to 1/100$^{th}$ of a standard slice of bread) damages the small intestine, chronic inflammation of the small bowel is commonplace in subjects on a gluten free diet. Persistent inflammation of the small intestine has been shown to increase the risk of cancer, osteoporosis and death. As gluten is so widely used, for example, in commercial soups, sauces, ice-creams, etc., maintaining a gluten free diet is difficult. Therefore novel epitopes for diagnosis and treatment of celiac disease are needed.

SUMMARY

Provided herein are novel polypeptide arrays for detection or diagnosis of celiac disease in a subject. In certain embodiments, an array of features attached to a surface at positionally-defined locations is provided, the features comprising at least one engineered polypeptide chain comprising at least two epitope sequences from a bioactive polypeptide that generates an immune response in subject having celiac disease, wherein the polypeptide chain further comprises at least one randomly generated polypeptide sequence. In an embodiment, the bioactive polypeptide is selected from the group consisting of: alpha gliadin, beta gliadin, gamma gliadin, and omega gliadin. In an embodiment, the at least one engineered polypeptide chain comprises at least 1, 2, 3, 4, 5, 6, 7, 8, 9, 10, 20, 30, 40, 50, 60, 70, 80, 90, or 100 sequences selected from the group consisting of SEQ ID NOS: 1-127, or a biologically active fragment or variant of any one or more thereof.

In some embodiments, the features are from 6 to 15 amino acids in length. In an embodiment, the features are 12 amino acids in length. In some embodiments, the features attached to the surface of the array are configured to have at least 90% sensitivity and 90% specificity for detection of celiac disorder after contact of the features with a sample from a subject suspected of having celiac disorder. In some embodiments, each of the at least two discontinuous epitopes consists of three amino acids. In some embodiments, each of the at least two discontinuous epitopes consists of 3, 4, 5, 6, 7, 8, 9, 10, or 11 amino acids. In an embodiment, each of the at least two discontinuous epitopes consists of 3 amino acids with at least 20% sensitivity for binding to an antibody in a celiac positive sample, wherein the peptide chain is 7, 8, 9, 10, 11, 12, 13, 14, or 15 amino acids in length.

In some embodiments, the array further comprises at least 10,000 features, each feature is attached to a surface of the array at a different positionally-defined location, the positionally defined location of each feature corresponds to a positionally-defined location of a pillar, wherein the top surface of each pillar is at least 1 µm$^2$ in size. In some embodiments, each feature comprises a different engineered peptide chain compared to the other features, each feature comprises at least 500 identical full-length peptide chains, wherein each identical full-length peptide chain has an engineered full-length of at least 7 amino acids in length, and the purity of each feature with regards to the fraction of full-length engineered peptide chains is a fraction F of the full-length engineered peptide chains of each feature having a engineered sequence and a engineered full-length sequence length N being characterized by $F=10^{(N+1) \cdot log(E/100\%)}$ with an average coupling efficiency E of at least 98.5% for coupling each amino acid of the engineered sequence, and the sequence length N being at least 7 amino acids in length, the fraction of the less than full-length engineered peptide chains equaling (1-F)

In some embodiments, the surface of the array comprises a substrate, the substrate comprising: a planar layer having an upper surface and a lower surface, and a plurality of pillars operatively coupled to the layer in the positionally-defined locations, wherein each pillar has a planar surface extended from the layer, wherein the distance between the surface of each pillar and the upper surface of the layer is between 1,000-5,000 angstroms, and wherein the plurality of pillars are present at a density of greater than 10,000/cm$^2$.

Also provided herein is a method of identifying novel epitopes for binding to an antibody associated with an autoimmune disorder, the method comprising: synthesizing a plurality of polypeptides on a first array, the plurality of polypeptides comprising overlapping polypeptide sequences from a protein suspected of comprising epitopes that bind to an antibody associated with an immune disorder; contacting the first array with a first sample from a subject with the immune disorder; determining which of the overlapping polypeptide sequences are bound to an antibody from the first sample to generate binding data; analyzing the binding data to identify a plurality of continuous epitopes in the protein; further analyzing each of the plurality of continuous epitopes to identify a plurality of discontinuous epitope pairs with the highest sensitivity (false positive rate) of binding to the antibody from the sample, thereby identifying novel epitopes for binding to the antibody associated with the autoimmune disorder.

In some embodiments, the method of identifying novel epitopes for binding to an antibody associated with an autoimmune disorder further comprises synthesizing a plurality of synthetic polypeptides on a second array, each synthetic polypeptide comprising at least two of the plurality of discontinuous epitopes, each synthetic polypeptide further comprising a random polypeptide sequence; contacting the second array with a second sample from a subject with the immune disorder; determining the sensitivity (false positive rate) and specificity (false negative rate) of binding of antibodies from the second sample to each of the plurality of synthetic polypeptides; identifying the synthetic polypeptides with the highest sensitivity and/or specificity of binding to an antibody associated with the immune disorder, thereby identifying refined novel epitopes for binding to the antibody associated with the autoimmune disorder.

In some embodiments, the plurality of polypeptides comprises a deamidated polypeptide sequence from the protein. In an embodiment, the plurality of polypeptides are 6-15 amino acids in length. In an embodiment, the autoimmune disorder is celiac disease. In an embodiment, the antibodies from the first or second sample are IgA or IgG antibodies. In an embodiment, the synthetic polypeptide is 6-15 amino acids in length. In an embodiment, the synthetic polypeptide is 12 amino acids in length. In some embodiments the plurality of continuous epitopes each bind to an antibody in at least 20%, 30%, 40%, or 50% of samples comprising the autoimmune disorder.

Also provided herein is an array of features attached to a surface at positionally-defined locations, the features comprising at least one novel epitope identified by the methods disclosed herein.

Also provided herein is a method of identifying an autoimmune disorder in a subject, comprising: contacting a sample from the subject with an array of one or more of the embodiments described herein; and analyzing binding of antibodies in the sample to the features on the array to determine whether the subject has the autoimmune disorder. In some embodiments, the autoimmune disorder is celiac disease. In some embodiments, the method comprises a sensitivity (false positive rate) of detection of the autoimmune disorder of at least 90%, 91%, 92%, 93%, 94%, 95%, 96%, 97%, 98%, or 99%. In some embodiments, the method comprises a specificity (false negative rate) of detection of the autoimmune disorder least 90%, 91%, 92%, 93%, 94%, 95%, 96%, 97%, 98%, or 99%. In some embodiments, the method comprises a sensitivity of detection of the Marsh classification of celiac disorder in the subject of at least 90%, 91%, 92%, 93%, 94%, 95%, 96%, 97%, 98%, or 99%.

Also provided herein are compositions comprising one or more isolated polypeptides comprising a sequence selected from the group consisting of SEQ ID NOS: 1-127, or biologically active fragments or variants of any one or more thereof.

Furthermore disclosed are substantially purified and/or recombinant polypeptides comprising an amino acid sequence selected from the group consisting of SEQ ID NOS: 1-127, biologically active fragments or variants of any one or more thereof.

Methods of treating celiac disorder or a celiac related disorder in a patient are disclosed, comprising administering to said patient a formulation comprising an amino acid sequence selected from the group consisting of SEQ ID NOS: 1-127, or biologically active fragments or variants of any one or more thereof.

Biomarkers for celiac disease are disclosed comprising a polypeptide epitope for a celiac antibody, wherein the polypeptide epitope is selected from the group consisting of SEQ ID NOS: 1-127, or biologically active fragments or variants of any one or more thereof.

In some embodiments, the disclosed methods for synthesizing arrays involves generalized de-protection with selective activation, providing benefits, such as a higher fidelity of peptide synthesis and a greatly reduced time requirement for each step. Thus, in some embodiments, it is this combination of high-fidelity synthesis, shorter processing time that may result in a much higher yield and the ability to generate a large number of chips quite inexpensively with very high fidelity required for diagnostic testing.

Celiac disease is a good model to explore the early stage of disease development as one of the representative autoimmune diseases, because the target protein, gluten, which storage proteins from wheat, barley, and rye, are well known to be immunogenic[10-12]. While the pathogenesis of celiac disease appears to be T-cell mediated,[13] the diagnosis relies on the presence of self-reactive antibodies. The most common antibodies currently in use are directed against host proteins such as tissue transglutaminase (tTG) and endomysium[10], and may serve as markers of autoimmunity rather than as participants in the initiation of the disease, which results from responses to gluten proteins.[14] Further, the production of these antibodies can be used to predict the stage and severity of disease and to monitor dietary compliance; however, they lack the ability to discriminate amongst clinically relevant phenotypes. Gliadin specific antibodies provide examples that have not shown adequate sensitivity and specificity for the diagnosis of CD. Further, it is not understood how gliadin specific antibodies and epitopes contribute to the pathogenesis of celiac disease, especially in the early stage of development.[15-18]

How the pathogenic epitopes are recognized by B cells and evolved in celiac disease may help in understanding both the mechanism of disease initiation and to develop better clinical tools. Such epitopes of gliadin peptides may be modified by transglutaminase and evolved toward being more immunogenic to host. To demonstrate the possibility of a novel technology for identifying the biomarker for CD diagnosis, continuous epitopes of gliadin with post-translational modified peptide sequences, discontinuous peptide sequences, which were combined with peptide sequences of gliadin, and random 3- or 6-mer peptide sequences were synthesized. Methods for identifying the biomarker of CD diagnosis by the novel platform and technology with semiconductor high volume manufacturing process to generate continuous and discontinuous peptide sequences from the established antigen in an autoimmune disease are described herein.

BRIEF DESCRIPTION OF THE SEVERAL VIEWS OF THE DRAWINGS

FIGS. 5A, 5B and 5C show (A) fluorescein results for LKWLDSFTEQ (SEQ ID NO: 128), (B) for DKYYEPHLERA (SEQ ID NO: 129), and (C) mass spectroscopy analysis for peptide purity, according to an embodiment.

FIGS. 6A and 6B illustrate a celiac subsequence matrix, according to an embodiment. 3-mer subsequences with maximum occurrences amongst sequences with high sensitivity and specificity amongst IgG and IgA were determined and the best combinations of subsequences were plotted as a matrix table. These sequences were combined along with random 3-mers and 6-mers to form new sequences.

Figure 1A:
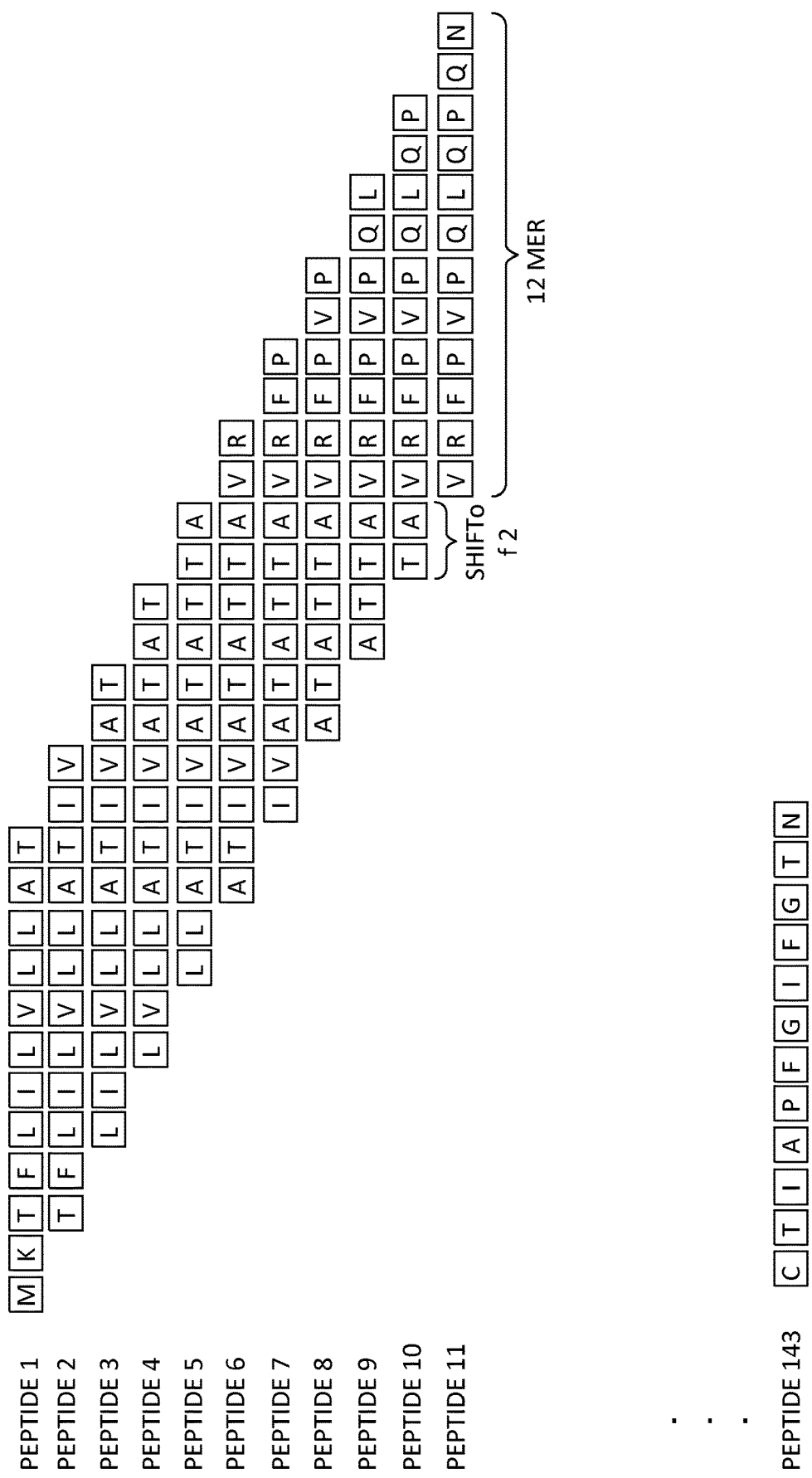
FIGS. 1A and 1B illustrate a proposed scheme for peptide synthesis on an array, according to an embodiment. (A) Arrays were designed with 2.1 million overlapping 12 amino acids long with a 2-amino-acid lateral shift covering the whole antigen sequences. (B) Examples of deamidation of native gliadin sequences one at a time and two at a time.

One skilled in the art will readily recognize from the following discussion that alternative embodiments of the structures and methods illustrated herein may be employed without departing from the principles of the invention described herein.

DETAILED DESCRIPTION

Terms and Definitions

Terms used in the claims and specification are defined as set forth below unless otherwise specified.

As used herein the term "wafer" refers to a slice of semiconductor material, such as silicon or a germanium crystal generally used in the fabrication of integrated circuits. Wafers can be in a variety of sizes from, e.g., 25.4 mm (1 inch) to 300 mm (11.8 inches) along one dimension with thickness from, e.g., 275 μm to 775 μm.

As used herein the term "photoresist" or "resist" or "photoactive material" refers to a light-sensitive material that changes its solubility in a solution when exposed to ultra violet or deep ultra violet radiation. Photoresists are organic or inorganic compounds that are typically divided into two types: positive resists and negative resists. A positive resist is a type of photoresist in which the portion of the photoresist that is exposed to light becomes soluble to the photoresist developer. The portion of the photoresist that is unexposed remains insoluble to the photoresist developer. A negative resist is a type of photoresist in which the portion of the photoresist that is exposed to light becomes insoluble to the photoresist developer. The unexposed portion of the photoresist is dissolved by the photoresist developer.

As used herein the term "photomask" or "reticle" or "mask" refers to an opaque plate with transparent patterns or holes that allow light to pass through. In a typical exposing process, the pattern on a photomask is transferred onto a photoresist.

As used herein the term "coupling molecule" or "monomer molecule" includes any natural or artificially synthesized amino acid with its amino group protected with a fluorenylmethyloxycarbonyl group or a t-butoxycarbonyl group. These amino acids may have their side chains protected as an option. Examples of coupling molecules include Boc-Gly-Oh, Fmoc-Trp-Oh. Other examples are described below.

As used herein the term "coupling" or "coupling process" or "coupling step" refers to a process of forming a bond between two or more molecules such as a linking molecule or a coupling molecule. A bond can be a covalent bond such as a peptide bond. A peptide bond can be a chemical bond formed between two molecules when the carboxyl group of one coupling molecule reacts with the amino group of the other coupling molecule, releasing a molecule of water ($H_2O$). This is a dehydration synthesis reaction (also known as a condensation reaction), and usually occurs between amino acids. The resulting CO—NH bond is called a peptide bond, and the resulting molecule is an amide.

As used herein the terms "biomolecule," "polypeptide," "peptide," or "protein" are used interchangeably to describe a chain or polymer of amino acids that are linked together by bonds. Accordingly, the term "peptide" as used herein includes a dipeptide, tripeptide, oligopeptide, and polypeptide. The term "peptide" is not limited to any particular number of amino acids. In some embodiments, a peptide contains about 2 to about 50 amino acids, about 5 to about 40 amino acids, about 5 to about 20 amino acids, or about 7 to about 15 amino acids. A molecule, such as a protein or polypeptide, including an enzyme, can be a "native" or "wild-type" molecule, meaning that it occurs naturally in nature; or it may be a "mutant," "variant," "derivative," or "modification," meaning that it has been made, altered, derived, or is in some way different or changed from a native molecule or from another molecule such as a mutant.

As used herein the term "linker molecule" or "spacer molecule" includes any molecule that does not add any functionality to the resulting peptide but spaces and extends out the peptide from the substrate, thus increasing the distance between the substrate surface and the growing peptide. This generally reduces steric hindrance with the substrate for reactions involving the peptide (including uni-molecular folding reactions and multi-molecular binding reactions) and so improves performance of assays measuring one or more embodiments of peptide functionality.

As used herein the term "developer" refers to a solution that can selectively dissolve the materials that are either exposed or not exposed to light. Typically developers are water-based solutions with minute quantities of a base added. Examples include tetramethyl ammonium hydroxide in water-based developers. Developers are used for the initial pattern definition where a commercial photoresist is used. Use of developers is described in Example 1 below.

As used herein the term "protecting group" includes a group that is introduced into a molecule by chemical modification of a functional group in order to obtain chemoselectivity in a subsequent chemical reaction. Chemoselectivity refers to directing a chemical reaction along a desired path to obtain a pre-selected product as compared to another. For example, the use of tboc as a protecting group enables chemoselectivity for peptide synthesis using a light mask and a photoacid generator to selectively remove the protecting group and direct pre-determined peptide coupling reactions to occur at locations defined by the light mask.

As used herein the term "microarrays" refers to a substrate on which different probe molecules of protein or specific DNA binding sequences have been affixed at separate locations in an ordered manner thus forming a microscopic array.

As used herein the term "microarray system" refers to a system usually comprised of biomolecular probes formatted on a solid planar surface like glass, plastic or silicon chip plus the instruments needed to handle samples (automated robotics), to read the reporter molecules (scanners) and analyze the data (bioinformatic tools).

As used herein the term "patterned region" or "pattern" or "location" refers to a region on the substrate on which are grown different features. These patterns can be defined using photomasks.

As used herein the term "derivatization" refers to the process of chemically modifying a surface to make it suitable for biomolecular synthesis. Typically derivatization includes the following steps: making the substrate hydrophilic, adding an amino silane group, and attaching a linker molecule.

As used herein the term "capping" or "capping process" or "capping step" refers to the addition of a molecule that prevents the further reaction of the molecule to which it is attached. For example, to prevent the further formation of a peptide bond, the amino groups are typically capped with an acetic anhydride molecule.

As used herein the term "diffusion" refers to the spread of a chemical through random motion from regions of higher concentration to regions of lower concentration.

As used herein the term "dye molecule" refers to a dye which typically is a colored substance that can bind to a substrate. Dye molecules can be useful in detecting binding between a feature on an array and a molecule of interest.

As used herein, the terms "immunological binding" and "immunological binding properties" refer to the type of non-covalent interactions that occurs between an immunoglobulin molecule (or variant thereof such as an scFv) and an antigen for which the immunoglobulin is specific.

As used herein the term "biological sample" refers to a sample derived from biological tissue or fluid that can be assayed for an analyte(s) of interest. Such samples include, but are not limited to, sputum, amniotic fluid, blood, blood cells (e.g., white cells), tissue or fine needle biopsy samples, urine, peritoneal fluid, and pleural fluid, or cells therefrom. Biological samples may also include sections of tissues such as frozen sections taken for histological purposes. Although the sample is typically taken from a human patient, the assays can be used to detect analyte(s) of interest in samples from any organism (e.g., mammal, bacteria, virus, algae, or yeast) or mammal, such as dogs, cats, sheep, cattle, and pigs. The sample may be pretreated as necessary by dilution in an appropriate buffer solution or concentrated, if desired.

As used herein, the term "assay" refers to a type of biochemical test that measures the presence or concentration of a substance of interest in solutions that can contain a complex mixture of substances.

The term "subject" includes inter alia an individual, patient, target, host or recipient regardless of whether the subject is a human or non-human animal including mammalian species and also avian species. The term "subject", therefore, includes a human, non-human primate (for example, gorilla, marmoset, African Green Monkey), livestock animal (for example, sheep, cow, pig, horse, donkey, goat), laboratory test animal (for example, rat, mouse, rabbit, guinea pig, hamster), companion animal (for example, dog, cat), captive wild animal (for example, fox, deer, game animals) and avian species including poultry birds (for example, chickens, ducks, geese, turkeys). The preferred subject, however, is a human.

The term "antigen" as used herein refers to a molecule that triggers an immune response by the immune system of a subject, e.g., the production of an antibody by the immune system and/or activation of the cellular arm of the immune system (e.g., activation of phagocytes, natural killer cells, and antigen-specific cytotoxic T-lymphocytes, along with release of various cytokines in response to an antigen). Antigens can be exogenous, endogenous or auto antigens. Exogenous antigens are those that have entered the body from outside through inhalation, ingestion or injection. Endogenous antigens are those that have been generated within previously-normal cells as a result of normal cell metabolism, or because of viral or intracellular bacterial infection. Auto antigens are those that are normal protein or protein complex present in the host body but can stimulate an immune response.

As used herein the term "epitope" or "immunoactive regions" refers to distinct molecular surface features of an antigen capable of being bound by component of the adaptive immune system, e.g., an antibody or T cell receptor. Antigenic molecules can present several surface features that can act as points of interaction for specific antibodies. Any such distinct molecular feature can constitute an epitope. Therefore, antigens have the potential to be bound by several distinct antibodies, each of which is specific to a particular epitope.

As used herein the term "antibody" or "immunoglobulin molecule" refers to a molecule naturally secreted by a particular type of cells of the immune system: B cells. There are five different, naturally occurring isotypes of antibodies, namely: IgA, IgM, IgG, IgD, and IgE.

As used herein the term "immune-related molecule" refers to a biological molecule involved in the activation or regulation of an immune response. These include, for example, an antibody, T cell receptor, or MHC complex (e.g., human leukocyte antigen).

As used herein, the term "inflammatory response molecule" refers to molecules that signal or mediate an inflammatory response, e.g., cytokines such as interleukin and tumor necrosis factor. Inflammatory response molecules include, for example, pro-inflammatory molecules.

As used herein, the term "autoimmune disorder" refers to any of a large group of diseases characterized by abnormal functioning of the immune system that causes a subject's immune system to damage the subject's own tissues. Celiac disorder, lupus erythematosis, and rheumatoid arthritis are examples of autoimmune disorders. Autoimmune disorders may be induced by environmental factors.

The term "percent identity" or "percent sequence identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website. Percent identity scores can be calculated using default values for this program as available on the National Center for Biotechnology Information website as of the priority date of this application.

As used herein the term "biologically active fragment" or variant thereof refers to a polypeptide capable of generating a substantially equal or greater T cell response in a subject sensitive to gluten as the polypeptide (e.g., gliadin) from which it is derived. In another embodiment, biologically active fragments are capable of generating at least 50%, more preferably at least 75% of the T cell response in a subject sensitive to gluten as the polypeptide from which it is derived. In an embodiment, biologically active fragments are 14, 13, 12, 11, 10, 9, 8 and no less than 7 amino acids in length. Deletions and/or additions at either end of any of the peptides are particularly contemplated. Examples of biologically active fragments disclosed herein include SEQ ID NO: 1-127.

The term "celiac disease" refers to a chronic inflammatory disease of the small intestine. The disease encompasses a spectrum of conditions characterised by varying degrees of gluten sensitivity, including a severe form characterised by a flat small intestinal mucosa (hyperplastic villous atrophy) and other forms characterised by milder symptoms including fatigue, chronic diarrhea, malabsorption of nutrients, weight loss, abdominal distension, anemia as well as a substantially enhanced risk for the development of osteoporosis and intestinal malignancies (lymphoma and carcinoma).

The term "sensitive to gluten" refers to the state in which any one or more of the symptoms of celiac disease or an inappropriate T cell response are exhibited by a subject exposed to gluten, or peptide fragment thereof. In a subject who is not sensitive to gluten, there is little or no T cell response caused by ingestion of gluten. By contrast, in a subject sensitive to gluten there is an inappropriate $CD4^+$ T cell mediated immune response to peptides derived from gluten after ingestion thereof.

The terms "immune tolerance", "immunological tolerance", "tolerance" or "desensitise" are here defined as to make a sensitised or hypersensitive subject, less sensitive, insensitive or nonreactive to gluten by reducing the immunological reactivity of a subject towards gluten. Immune tolerance may be generated, for example, by exposure of mucosal surfaces to tolerance-inducing antigenic fragments of gluten as defined herein. Mucosal administration of both high- and low-dose antigen may result in immune tolerance, in which the immune response to subsequent systemic administration of antigen is reduced. At least two mechanisms of immune tolerance may exist. Tolerance to high-doses of an antigen appears to occur by inactivation or clonal deletion of Th1 and Th2 cells. In contrast, tolerance to low doses of antigen leads to bystander immune suppression mediated by stimulation of Treg cells to produce suppressive cytokines such as interleukin-4 (IL-4), interleukin-10 (IL-10) and TGFβ.

The term "inducing immune tolerance" as used herein refers to bringing about, producing, or causing immune tolerance to gluten in a subject sensitive to gluten.

The term "hypersensitive" is here defined as abnormally susceptible physiologically to gluten.

The term "anergy" refers to a state of reversible unresponsiveness or hyporesponsiveness of a T cell (or B cell) to an antigen.

As used herein, "Treg" refers to a subclass of T cells whose major role is to bring T cell-mediated immunity during an immune reaction to an end, and to suppress auto-reactive T cells that escaped negative selection in the thymus. A "Treg response", as used herein, is characterised by the differentiation and proliferation of the population of $CD4^+$ or $CD8^+$ Treg cells which express the forkhead family transcription factor FOXP3 (forkhead box p3) and/or the MHC Class II associated protein LAG-3, and/or express high levels of the IL-2 receptor alpha chain (CD25). There is also a minor population of MHC Class I-restricted $CD8^+$ FOXP3-expressing Treg cells. The presence of Treg cells in the peripheral circulation or spleen may be determined by analysis of $CD4^+/CD25^+$ expression. This may conveniently be achieved using flow cytometry. In addition, Treg cells may be quantified by determining levels of FOXP3 mRNA in peripheral blood- or spleen-derived mononuclear cells by quantitative reverse transcriptase polymerase chain reaction (PCR). In addition, the induction of a Treg response in vivo may be assessed by the measurement of Treg-associated cytokines from peripheral blood- or lymph node-derived mononuclear lymphocytes. Treg cells typically show higher expression levels of the anti-inflammatory cytokines such as IL-10 and TGFβ and the presence of these mediators may be determined by methods known in the art, such as flow cytometry, immunohistochemical staining or ELISA.

The term "T cell stimulatory peptide" or "stimulatory peptide" refers to a peptide or epitope capable of activating a T cell.

The term "activate" or "activating" or "activation" in relation to a T cell refers to the presentation by an MHC molecule on one cell of an epitope to an appropriate T cell receptor on a second (T) cell, together with binding of a co-stimulatory molecule by the T cell, thereby eliciting a "T cell response".

As used herein, "toxic peptide" refers to a peptide that stimulates T cell activation in a subject.

The term "expansion" as used herein refers to the proliferation and amplification of a T cell population following T cell activation.

The term "immunodominant" refers to a subunit of a peptide (epitope) that is most easily recognised by the immune system and thus most influences the specificity of an induced immune response, such as a T cell response "Immunodominant" may be used interchangeably with "dominant" herein.

As used herein, the term "modulating a T cell response" refers to regulating or adjusting a T cell response in a subject sensitive to gluten, such that the T cell response to gluten is reduced or lessened.

As used herein, "modifying cytokine secretion" refers to changing or altering somewhat the secretion of cytokines by a subject sensitive to gluten, such that the effects of gluten sensitivity in the subject are reduced or lessened. The term encompasses both increased secretion of a particular cytokine or combination of cytokines and decreased secretion of a particular cytokine or combination of cytokines.

As used herein, "epitope" refers to that portion of an antigen or a peptide that is recognized by the immune system, for example, a T cell receptor or the major histocompatibility complex (MHC) class I or class II, an antibody, a B cell receptor, which portion is sufficient for high affinity binding. Generally, a linear epitope for recognition will be at least about 3 amino acids in length, and may be 4, 5, 6, 7, 8, 9, 10, 11, 12, 13, 14, 15 amino acids in length, or more.

The term "polyepitope" refers to the presence of two or more epitopes (peptides) linked in a single polypeptide chain.

As used herein, "antigen" and "immunogen" and variations thereof are generally used interchangeably and refer to the epitope-containing structure recognised by the immune system.

The term "gluten" or "gluten protein" encompasses alpha (α), beta (β), gamma (γ) and omega (ω) gliadins, and low and high molecular weight (LMW and HMW) glutenins in wheat, B, C and D hordeins in barley, β, γ and ω secalins in rye, and optionally avenins in oats. "Gluten peptides" are peptides derived from, or encompassed within, one or more of the gluten proteins.

The term "gliadin" refers to the aqueous alcohol-soluble fraction of gluten, particularly, but not exclusively, gluten derived from wheat, for example *Triticum aestivum*.

The term "glutenin" refers to the aqueous alcohol-insoluble fraction of gluten, particularly but not exclusively, gluten derived from wheat, for example *Triticum aestivum*.

As used herein, "hordein" or "barley hordein" refers to gluten derived from barley, *Hordein vulgare*.

As used herein, "secalin" or "rye secalin" refers to gluten derived from rye, *Secale cerale*.

As used herein, "avedin" or "oat avedin" refers to gluten derived from oats, *Avena sativa*. The terms "human leukocyte antigen" and "HLA" are here defined as a genetic fingerprint on human white blood cells and platelets, composed of proteins that play a critical role in activating the body's immune system to respond to foreign organisms. In humans and other animals, the HLA is also referred to as the "major histocompatibility complex" (MHC).

Tissue "transglutaminase" is a crucial factor in celiac disease because it promotes gluten-specific T cell responses. Tissue transglutaminase causes selective deamidation of gluten, which in turn, causes the generation of a series of gluten peptides that bind to HLA-DQ2 or -DQ8 molecules with high affinity. The resulting HLA-DQ2 (DQ8)-gluten peptide interaction triggers the proinflammatory CD4 T cell response. Thus, the term "deamidation" refers to the conversion of glutamine to glutamic acid, or to the conversion of asparagine to aspartic acid. As used herein, deamidation refers particularly to the conversion of glutamine to glutamic acid in gluten, a process that increases the propensity of gluten peptides to activate T cells.

As used herein, the term "agent" refers to a collection of peptides and/or polynucleotides. The peptides and/or polynucleotides may be in the same composition (such as a vaccine), in different compositions or a combination thereof (for example, the first and second peptide defined herein in one composition, and the third in a separate composition). If in different compositions, they will preferably be in close proximity, such as in a kit. Accordingly, the methods of the invention contemplate providing (for example administering to a subject) the individual component peptides and/or polynucleotides of an agent of the invention in a single composition (vaccine), or sequentially in different compositions or a combination thereof.

It must be noted that, as used in the specification and the appended claims, the singular forms "a," "an," and "the" include plural referents unless the context clearly dictates otherwise.

Peptides

The present disclosure relates to the following peptides and modifications thereof. Some embodiments include novel and selective polyepitode-containing peptides that are agents or vaccines for treating and diagnosing celiac disease. In some embodiments, the polyepitode-containing peptides are antigens that modulate a T cell response of a subject who is sensitive to gluten or who has celiac disease. Examples of these polyepitode-containing and celiac active peptides, which are optionally amidated at the C-termini, are provided in Tables 1 and 2.

TABLE 1

IgG Antibody Assay (Set #3)

|  |  | Sensitivity | Specificity |
|---|---|---|---|
| RRGQP FWQPE LT | SEQ ID NO: 1 | 41% | 100% |
| VVDPE QPQQD CT | SEQ ID NO: 2 | 42% | 100% |

TABLE 1-continued

IgG Antibody Assay (Set #3)

| | | Sensitivity | Specificity |
|---|---|---|---|
| GQPFQ PEQPW LT | SEQ ID NO: 3 | 44% | 98% |
| GQPFW LTQPE QP | SEQ ID NO: 4 | 40% | 99% |
| TATVV DPEQP QQ | SEQ ID NO: 5 | 48% | 100% |
| YPEQP EQPGS SE | SEQ ID NO: 6 | 72% | 100% |
| RANHL NQPEQ PF | SEQ ID NO: 7 | 45% | 98% |
| QPFWQ PEQPF LT | SEQ ID NO: 8 | 52% | 100% |
| LHFPE QPEGR NY | SEQ ID NO: 9 | 51% | 98% |
| NQPEQ PFPLP VA | SEQ ID NO: 10 | 56% | 100% |
| RGQPF QPEQP FW | SEQ ID NO: 11 | 52% | 100% |
| TRPDL EQPFP QP | SEQ ID NO: 12 | 56% | 100% |
| HFPEQ PEGRN YE | SEQ ID NO: 13 | 38% | 100% |
| VVRRG QPFWQ PE | SEQ ID NO: 14 | 46% | 100% |
| GQPFW LQPEQ PT | SEQ ID NO: 15 | 55% | 100% |
| RGQPF WQPEL TL | SEQ ID NO: 16 | 72% | 100% |
| RGQPF WLTLQ PE | SEQ ID NO: 17 | 39% | 100% |
| RGQPF WLQPE TL | SEQ ID NO: 18 | 64% | 100% |
| FPEQP EGRNY EA | SEQ ID NO: 19 | 60% | 100% |
| LVVNF PEQPE SD | SEQ ID NO: 20 | 30% | 100% |
| EQPEQ PFSNL IK | SEQ ID NO: 21 | 65% | 98% |
| VRRGQ PFQPE WL | SEQ ID NO: 22 | 64% | 100% |
| GQPFW LTQPE QL | SEQ ID NO: 23 | 57% | 98% |
| RRGQP FWLQP ET | SEQ ID NO: 24 | 71% | 100% |
| FPEQP EDGIL DI | SEQ ID NO: 25 | 51% | 100% |
| VRRGQ PFQPE QP | SEQ ID NO: 26 | 36% | 100% |
| GQPFW LQPEQ PF | SEQ ID NO: 27 | 35% | 100% |
| GQPFW LTLQP EQ | SEQ ID NO: 28 | 69% | 100% |
| ENPEQ PEQPF IK | SEQ ID NO: 29 | 37% | 100% |
| RGQPF WQPEQ LT | SEQ ID NO: 30 | 41% | 98% |
| HKLVV NFPEQ PE | SEQ ID NO: 31 | 30% | 100% |
| RGQPF WLTQP EQ | SEQ ID NO: 32 | 67% | 98% |
| TQPEQ PFVEI PD | SEQ ID NO: 33 | 35% | 100% |
| MNMQP EQPFG SD | SEQ ID NO: 34 | 56% | 100% |
| TYKYP EQPEQ PG | SEQ ID NO: 35 | 34% | 100% |
| WNFGQ FPEQP ED | SEQ ID NO: 36 | 32% | 100% |
| GQPFW LQPET LH | SEQ ID NO: 37 | 39% | 100% |
| LTLHF PEQPE GR | SEQ ID NO: 38 | 39% | 100% |
| NFPEQ PESDK LK | SEQ ID NO: 39 | 32% | 100% |
| VNFPE QPESD KL | SEQ ID NO: 40 | 38% | 100% |

TABLE 1-continued

IgG Antibody Assay (Set #3)

| | | Sensitivity | Specificity |
|---|---|---|---|
| TLHFP EQPEG RN | SEQ ID NO: 41 | 57% | 98% |
| LYLEN PEQPE QP | SEQ ID NO: 42 | 48% | 100% |
| AVEEQ PEQPG DW | SEQ ID NO: 43 | 58% | 98% |
| QFPEQ PEDGI LD | SEQ ID NO: 44 | 58% | 100% |
| QPFWL QPEQP TL | SEQ ID NO: 45 | 37% | 98% |
| FPEQP ESDKL KA | SEQ ID NO: 46 | 75% | 100% |
| GQPFQ PEQPF WL | SEQ ID NO: 47 | 66% | 100% |
| KARFP QPEQL RD | SEQ ID NO: 48 | 60% | 100% |
| PEQPE QPIKI RI | SEQ ID NO: 49 | 71% | 100% |
| ALDPT PQPEQ PF | SEQ ID NO: 50 | 66% | 100% |
| LVVRR GQPFQ PE | SEQ ID NO: 51 | 36% | 100% |
| FAAVA QPEQP FC | SEQ ID NO: 52 | 51% | 100% |
| GQPFW LQPEQ TL | SEQ ID NO: 53 | 39% | 98% |
| YVLTP EQPFP QQ | SEQ ID NO: 54 | 67% | 98% |
| KARFP QPEQP FL | SEQ ID NO: 55 | 63% | 99% |
| QPFWL TLHFQ PE | SEQ ID NO: 56 | 75% | 100% |
| EQPFP QPFWL TL | SEQ ID NO: 57 | 32% | 100% |
| RRGQP FWQPE QP | SEQ ID NO: 58 | 45% | 100% |
| RGQPF QPEWL TL | SEQ ID NO: 59 | 39% | 100% |
| QEQPE QPAGT KA | SEQ ID NO: 60 | 74% | 100% |
| SQPEQ PFGMV NC | SEQ ID NO: 61 | 62% | 100% |
| VRRGP EQPFP QP | SEQ ID NO: 62 | 41% | 99% |
| GQPFW QPELT LH | SEQ ID NO: 63 | 62% | 100% |
| LEQPE QPFSE KS | SEQ ID NO: 64 | 42% | 100% |
| VRRGQ PFWLQ PE | SEQ ID NO: 65 | 45% | 100% |
| QPFQP EQPWL TL | SEQ ID NO: 66 | 66% | 100% |
| FGQFP EQPED GI | SEQ ID NO: 67 | 62% | 100% |
| VRRGQ PFWQP EL | SEQ ID NO: 68 | 47% | 100% |
| RDLYL EQPEQ PF | SEQ ID NO: 69 | 60% | 100% |
| QPFQP EQWLT LH | SEQ ID NO: 70 | 40% | 99% |
| NPEQP EQPIK IR | SEQ ID NO: 71 | 45% | 100% |

TABLE 2

IgA antibody assay (Set #4)

| | | Sensitivity | Specificity |
|---|---|---|---|
| LEQPE QPFSE KS | SEQ ID NO: 64 | 38% | 100% |
| RGQPF WLQPE TL | SEQ ID NO: 18 | 60% | 100% |

TABLE 2-continued

IgA antibody assay (Set #4)

| Sequence | SEQ ID NO | Sensitivity | Specificity |
|---|---|---|---|
| RGQPF QPEWL TL | SEQ ID NO: 59 | 59% | 100% |
| VRRGQ PFQPE QW | SEQ ID NO: 72 | 73% | 100% |
| EQPEQ PFSNL IK | SEQ ID NO: 21 | 73% | 100% |
| YKYPE QPEQP FG | SEQ ID NO: 73 | 59% | 100% |
| GPEQP FPQPF WL | SEQ ID NO: 74 | 51% | 100% |
| QPFWL QPEQT LH | SEQ ID NO: 75 | 31% | 100% |
| TATVV DPEQP QQ | SEQ ID NO: 5 | 69% | 100% |
| HKLVV NFPEQ PE | SEQ ID NO: 31 | 38% | 100% |
| VVDWI QPEQP QQ | SEQ ID NO: 76 | 71% | 100% |
| KARFP QPEQL RD | SEQ ID NO: 48 | 31% | 100% |
| PEQPF PQQDD GS | SEQ ID NO: 77 | 45% | 100% |
| RRGQP FQPEQ WL | SEQ ID NO: 78 | 68% | 100% |
| QPFQP EQWLT LH | SEQ ID NO: 70 | 51% | 100% |
| NGILG PEQPE QC | SEQ ID NO: 79 | 70% | 100% |
| PEQPE QPIKI RI | SEQ ID NO: 49 | 39% | 100% |
| VVNFP EQPES DK | SEQ ID NO: 80 | 63% | 100% |
| RANHL NQPEQ PF | SEQ ID NO: 7 | 48% | 100% |
| GQPFQ PEWLT LH | SEQ ID NO: 81 | 62% | 100% |
| VVDPE QPQQD CT | SEQ ID NO: 2 | 60% | 100% |
| QPEQP FVDQQ DC | SEQ ID NO: 82 | 62% | 100% |
| TRPDL EQPFP QP | SEQ ID NO: 12 | 40% | 100% |
| FPEQP EDGIL DI | SEQ ID NO: 25 | 42% | 100% |
| HTYKY PEQPE QP | SEQ ID NO: 83 | 62% | 100% |
| RRGQP FQPEW LT | SEQ ID NO: 84 | 41% | 100% |
| GQPFW LTQPE LH | SEQ ID NO: 85 | 32% | 100% |
| RGQPF WQPEQ LT | SEQ ID NO: 30 | 75% | 100% |
| YPEQP EQPGS SE | SEQ ID NO: 6 | 60% | 100% |
| ENPEQ PEQIK IR | SEQ ID NO: 86 | 38% | 100% |
| KARFP QPEQP FL | SEQ ID NO: 55 | 40% | 100% |
| GQPFW QPEQP LT | SEQ ID NO: 87 | 36% | 100% |
| GQPFW LTLQP EH | SEQ ID NO: 88 | 70% | 100% |
| WLTLH FPEQP EG | SEQ ID NO: 89 | 68% | 100% |
| WNFGQ FPEQP ED | SEQ ID NO: 36 | 58% | 100% |
| GQPFW LQPEQ PT | SEQ ID NO: 15 | 30% | 100% |
| RGQPF WQPEL TL | SEQ ID NO: 16 | 67% | 100% |
| RGQPF WLTLQ PE | SEQ ID NO: 17 | 33% | 100% |
| SQPEQ PFGMV NC | SEQ ID NO: 61 | 61% | 100% |
| QPFWL TLHQP EQ | SEQ ID NO: 90 | 59% | 100% |
| GQPFW QPELT LH | SEQ ID NO: 63 | 63% | 100% |
| RGQPF WQPEQ PF | SEQ ID NO: 91 | 35% | 100% |
| QPEQP QQDCT LS | SEQ ID NO: 92 | 58% | 100% |
| RRGEQ PFPQP FW | SEQ ID NO: 93 | 65% | 100% |
| QPFWL QPEQP TL | SEQ ID NO: 45 | 43% | 100% |
| VLTQP EQPQQ GF | SEQ ID NO: 94 | 51% | 100% |
| RRGQP FWQPE LT | SEQ ID NO: 1 | 53% | 100% |
| YVLTP EQPFP QQ | SEQ ID NO: 54 | 44% | 100% |
| QPFWL QPEQP FT | SEQ ID NO: 95 | 31% | 100% |
| QPFWQ PELTL HF | SEQ ID NO: 96 | 65% | 100% |
| FWLTL HFPEQ PE | SEQ ID NO: 97 | 69% | 100% |
| RRGQP FWLTQ PE | SEQ ID NO: 98 | 51% | 100% |
| FPEQP ESDKL KA | SEQ ID NO: 46 | 40% | 100% |
| TYKYP EQPEQ GS | SEQ ID NO: 99 | 62% | 100% |
| GILGP EQPEQ PF | SEQ ID NO: 100 | 65% | 100% |
| DLEQP FPQPG YE | SEQ ID NO: 101 | 41% | 100% |
| RDLYL EQPEQ PF | SEQ ID NO: 69 | 36% | 100% |
| QPFWL TLHFQ PE | SEQ ID NO: 56 | 67% | 100% |
| GQPFW QPEQP FL | SEQ ID NO: 102 | 42% | 100% |
| VRRGQ PFQPE QP | SEQ ID NO: 26 | 43% | 100% |
| LHFPE QPEGR NY | SEQ ID NO: 9 | 37% | 100% |
| VVRRG QPFWQ PE | SEQ ID NO: 14 | 46% | 100% |
| GQPFQ PEQPF WL | SEQ ID NO: 47 | 30% | 100% |
| GQPFW LQPET LH | SEQ ID NO: 37 | 54% | 100% |
| GQFPE QPEDG IL | SEQ ID NO: 103 | 51% | 100% |
| RGQPF WLPQE QT | SEQ ID NO: 104 | 34% | 100% |
| RGQPF QPEQP FW | SEQ ID NO: 11 | 57% | 100% |
| DWIPE QPFPQ QD | SEQ ID NO: 105 | 44% | 100% |
| RGQPF WLQPE QP | SEQ ID NO: 106 | 54% | 100% |
| QPFQP EQPWL TL | SEQ ID NO: 66 | 44% | 100% |
| GQPFW LTQPE QP | SEQ ID NO: 4 | 63% | 100% |
| KLVVN FPEQP ES | SEQ ID NO: 107 | 53% | 100% |
| NFGQF PEQPE DG | SEQ ID NO: 108 | 75% | 100% |
| RFPQP EQPLR DA | SEQ ID NO: 109 | 69% | 100% |
| YKYPE QPEQG SS | SEQ ID NO: 110 | 56% | 100% |
| GQPFQ PEQPW LT | SEQ ID NO: 3 | 46% | 100% |
| LNLEQ PEQPF PF | SEQ ID NO: 111 | 49% | 100% |
| LGPEQ PEQPF CG | SEQ ID NO: 112 | 48% | 100% |

TABLE 2-continued

IgA antibody assay (Set #4)

| | | | Sensitivity | Specificity |
|---|---|---|---|---|
| AGTKA RFPQP EQ | SEQ ID NO: | 113 | 48% | 100% |
| YKYPE QPEQP GS | SEQ ID NO: | 114 | 55% | 100% |
| KRQPE QPFKL VA | SEQ ID NO: | 115 | 41% | 100% |
| FPEQP EGRNY EA | SEQ ID NO: | 19 | 41% | 100% |
| QFPEQ PEDGI LD | SEQ ID NO: | 44 | 74% | 100% |
| RRGPE QPFPQ PF | SEQ ID NO: | 116 | 50% | 100% |
| RRGQP FWQPE QP | SEQ ID NO: | 58 | 71% | 100% |
| QPFWQ PEQPF LT | SEQ ID NO: | 8 | 50% | 100% |
| TYKYP EQPEQ PG | SEQ ID NO: | 35 | 60% | 100% |
| GSSEE REQPE QP | SEQ ID NO: | 117 | 66% | 100% |
| VRRGQ PFWQP EL | SEQ ID NO: | 68 | 50% | 100% |
| QPFQP EQPFW LT | SEQ ID NO: | 118 | 50% | 100% |
| PEQPE QPGSS EE | SEQ ID NO: | 119 | 45% | 100% |
| VDWIQ PEQPQ QD | SEQ ID NO: | 120 | 34% | 100% |
| FGQFP EQPED GI | SEQ ID NO: | 67 | 63% | 100% |
| EQPFP QPFWL TL | SEQ ID NO: | 57 | 30% | 100% |
| VNFPE QPESD KL | SEQ ID NO: | 40 | 62% | 100% |
| VRRGQ PFWLQ PE | SEQ ID NO: | 65 | 69% | 100% |
| LENPE QPEQI KI | SEQ ID NO: | 121 | 30% | 100% |
| GTKAR FPQPE QL | SEQ ID NO: | 122 | 44% | 100% |
| RGQPF WLTQP EQ | SEQ ID NO: | 32 | 56% | 100% |
| NPEQP EQPFI KI | SEQ ID NO: | 123 | 56% | 100% |
| QPFWQ PEQLT LH | SEQ ID NO: | 124 | 74% | 100% |
| RGQPF WLTQP EL | SEQ ID NO: | 125 | 68% | 100% |
| EQPEQ PEVKV RM | SEQ ID NO: | 126 | 33% | 100% |
| VRRGE QPFPQ PF | SEQ ID NO: | 127 | 60% | 100% |

Disclosed herein are methods of identifying novel bioactive sequences and the use of those bioactive sequences. Uses of the arrays or formulations comprising novel bioactive sequences disclosed herein can include research applications, therapeutic purposes, medical diagnostics, and/or stratifying one or more patients or subjects.

Biologically active variants include peptides which vary by one or more amino acids from the defined peptide, which are also known in the art as homologues. For example, a variant can comprise one or more amino acid substitutions in any one or more of the peptides. As used herein, "substituted" or "substitution" includes substitution, replacement, addition, insertion, omission and/or deletion (as such variants may also be fragments) of an amino acid residue(s). In particular, this refers to peptides having conservative substitution without losing, or significantly diminishing, their use in the methods of the invention. Preferably, biologically active variants are capable of generating a substantially equal or greater T cell response in a subject sensitive to gluten as the peptide from which it is derived. In another embodiment, biologically active variants are capable of generating at least 50%, more preferably at least 75% of the T cell response in a subject sensitive to gluten as the peptide from which it is derived.

Biologically active variants of the peptides may be identified by modifying the sequence of each peptide and then assaying the resulting peptide for the ability to stimulate an immune response, for example, production of T cells.

In an embodiment, no more than 5, more preferably no more than 4, more preferably no more than 3, more preferably no more than 2, and even more preferably only 1 amino acid in a defined peptide is varied (by substitution, deletion or addition), when compared to a peptide sequence defined herein.

In an alternate embodiment, the percentage identity between a particular sequence (variant) and a reference sequence (peptide defined herein) is at least about 60% or at least about 70% or at least about 80% or at least about 90% or at least about 95% or above such as at least about 96%, 97%, 98%, 99% or greater. Percentage identity can be determined using readily available software packages, such as BLAST (www.ncbi.nlm.nih.gov/) and GAP. Natural amino acids include alanine (A), arginine (R), asparagine (N), aspartic acid (D), cysteine (C), glutamine (Q), glutamic acid (E), glycine (G), histidine (H), isoleucine (I), leucine (L), lysine (K), methionine (M), phenylalanine (F), proline (P), serine (S), threonine (T), tryptophan (W), tyrosine (Y), valine (V), hydroxyproline (O and/or Hyp), isodityrosine (IDT), and di-isodityrosine (di-IDT). Hydroxyproline, isodityrosine, and di-isodityrosine are formed post-translationally. Use of natural amino acids, in particular the 20 genetically encoded amino acids, is particularly contemplated.

Substitutions may be conservative amino acid substitutions, in which the substituted amino acid has similar structural or chemical properties with the corresponding amino acid in the reference sequence. Alternatively, the substitutions may be non-conservative amino acid substitutions as long as the desired activity is maintained.

By way of example, conservative amino acid substitutions involve substitution of one aliphatic or hydrophobic amino acids, for example, alanine, valine, leucine and isoleucine, with another; substitution of one hydroxyl-containing amino acid, for example, serine and threonine, with another; substitution of one acidic residue, for example, glutamic acid or aspartic acid, with another; replacement of one amide-containing residue, for example, asparagine and glutamine, with another; replacement of one aromatic residue, for example, phenylalanine and tyrosine, with another; replacement of one basic residue, for example, lysine, arginine and histidine, with another; and replacement of one small amino acid, for example, alanine, serine, threonine, methionine, and glycine, with another.

Peptide variants may be produced by mutagenesis or other chemical methods. Alanine scanning is a useful technique for identifying important amino acids. In this technique, an amino acid residue is replaced by Ala and its effect on the peptide's activity is determined. For example, cysteine residues may be substituted to minimise dimerisation via disulfide linkages. Each of the amino acid residues of the peptide is analysed in this manner to determine the important regions of the peptide. Means for preparing such peptides are well understood in the art.

In addition to naturally occurring amino acids, non-naturally occurring amino acids, or modified amino acids, are also contemplated and within the scope of the invention.

In fact, as used herein, "amino acid" refers to naturally occurring amino acids, non-naturally occurring amino acids, and amino acid analogues, and to the D or L stereoisomers of each.

The phrases "protecting group" and "blocking group" as used herein, refers to modifications to the peptide which protect it from undesirable chemical reactions, particularly in vivo. Examples of such protecting groups include esters of carboxylic acids and boronic acids, ethers of alcohols and acetals, and ketals of aldehydes and ketones. Examples of suitable groups include acyl protecting groups such as, for example, furoyl, formyl, adipyl, azelayl, suberyl, dansyl, acetyl, theyl, benzoyl, trifluoroacetyl, succinyl and methoxysuccinyl; aromatic urethane protecting groups such as, for example, benzyloxycarbonyl (Cbz); aliphatic urethane protecting groups such as, for example, t-butoxycarbonyl (Boc) or 9-fluorenylmethoxy-carbonyl (FMOC); pyroglutamate and amidation. Many other modifications providing increased potency, prolonged activity, ease of purification, and/or increased half-life will be known to the person skilled in the art.

In one embodiment, one of more glutamate residues of one or more of the peptides may be generated by tTG activity upon a peptide. In alternate embodiment, this reaction occurs in vivo following administration.

The peptides may comprise one or more modifications, which may be natural post-translation modifications or artificial modifications. The modification may provide a chemical moiety (typically by substitution of a hydrogen, for example, of a C—H bond), such as an amino, acetyl, acyl, carboxy, hydroxy or halogen (for example, fluorine) group, or a carbohydrate group. Typically, the modification is present on the N- or C-terminal. Furthermore, one or more of the peptides may be PEGylated, where the PEG (polyethyleneoxy group) provides for enhanced lifetime in the blood stream. One or more of the peptides may also be combined as a fusion or chimeric protein with other proteins, or with specific binding agents that allow targeting to specific moieties on a target cell.

Peptide variants may be obtained in which the peptide has been chemically modified at the level of amino acid side chains, of amino acid chirality, and/or of the peptide backbone Certain peptides described herein may exist in particular geometric or stereoisomeric forms. The present invention contemplates all such forms, including cis-(Z) and trans-(E) isomers, R- and S-enantiomers, diastereomers, (D)-isomers, (L)-isomers, the racemic mixtures thereof, and other mixtures thereof, as, falling within the scope of the invention. Additional asymmetric carbon atoms may be present in a substituent, such as an alkyl group. All such isomers, as well as mixtures thereof, are intended to be included in this invention.

In another example, to prevent cleavage by peptidases, any one or more of the peptides may include a non cleavable peptide bond in place of a particularly sensitive peptide bond to provide a more stable peptide. Such non cleavable peptide bonds may include beta amino acids.

In certain embodiments, any one or more of the peptides may include a functional group, for example, in place of the scissile peptide bond, which facilitates inhibition of a serine-, cysteine- or aspartate-type protease, as appropriate. For example, the invention includes a peptidyl diketone or a peptidyl keto ester, a peptide haloalkylketone, a peptide sulfonyl fluoride, a peptidyl boronate, a peptide epoxide, a peptidyl diazomethane, a peptidyl phosphonate, isocoumarins, benzoxazin-4-ones, carbamates, isocyantes, isatoic anhydrides or the like. Such functional groups have been provided in other peptide molecules, and general routes for their synthesis are known.

A variant may be a mimetic. The term "mimetic" is intended to refer to a substance which has some chemical similarity to the molecule it mimics and retains a particular activity of interest (for example, inducing tolerance). The underlying rationale behind the use of peptide mimetics, is that the peptide backbone of proteins exists chiefly to orient amino acid side chains in such a way as to facilitate molecular interactions, such as those of T cell and MHC-peptide, antibody and antigen, enzyme and substrate or scaffolding proteins. A peptide mimetic is designed to permit molecular interactions similar to the natural molecule. Mimetics include olefins, phosphonates, aza-amino acid analogues and the like. Persons skilled in the art would readily appreciate methods for designing mimetics of peptides and would be able to utilise them to design mimetics of the peptides defined herein.

The peptides may be analysed by hydrophilicity analysis, which can be used to identify the hydrophobic and hydrophilic regions of the peptide, thus aiding in the design of peptides for experimental manipulation, such as in binding experiments, antibody synthesis, etc. Secondary structural analysis may also be performed to identify regions of a peptide that adopt specific structural motifs. Manipulation, translation, secondary structure prediction, hydrophilicity and hydrophobicity profiles, open reading frame prediction and plotting, and determination of sequence homologies, can be accomplished using computer software programs available in the art. Other methods of structural analysis including, but not limited to, X-ray crystallography, mass spectrometry and gas chromatography, computer modelling, optical rotary dispersion (ORD), or circular dichroism (CD) may also be used.

The peptides, fragments or variants may be in a salt form, preferably, a pharmaceutically acceptable salt form. "A pharmaceutically acceptable salt form" includes the conventional non-toxic salts or quaternary ammonium salts of a peptide, for example, from non-toxic organic or inorganic acids. Conventional non-toxic salts include, for example, those derived from inorganic acids such as hydrochloride, hydrobromic, sulphuric, sulfonic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

The peptides can be provided in the agent or vaccine as separate peptides or linked, for example, in a polyepitope structure. In one embodiment, the peptides may be presented in a single polypeptide chain (polyepitope string), i.e., in a linear or circular arrangement. In another embodiment, the peptides can be presented in a multiple antigen presentation system, particularly based on a dendrimer backbone such as polylysine. A polylysine backbone provides a non-linear, branched arrangement of epitopes. This system provides the advantage over a polyepitope string that the peptides do not interfere with each other or be liable to cleavage into cryptic epitopes and thus are able to induce a full T cell response.

Conjugates

One or more of the peptides may be conjugated to a compound using standard methods. Examples of compounds to which the peptides can be conjugated include but are not limited to a radioisotope, a fluorescent label, a chemiluminescent compound, an enzyme label, a free radical, an avidin-biotin label, a bacteriophage label, a compound that increases the half life of the peptide in a subject, an adjuvant, an MHC molecule or fragment thereof.

The compound may facilitate detection and/or isolation or increase immunogenicity of the conjugated peptide.

"Conjugated" as used herein means coupled via covalent or non-covalent bonds. While covalent bonds are preferred, the compound may also be linked to the peptide via complexation without covalent linkage, for example, via hydrogen bonds or electrostatic, hydrophobic, etc., interaction.

Typical radioactive isotopes include $^3$H, $^{125}$I, $^{131}$I $^{32}$P, $^{35}$S, $^{14}$C, $^{51}$Cr, $^{36}$Cl, $^{57}$Co, $^{58}$Co, $^{59}$Fe, $^{75}$Se, and $^{152}$Eu.

Typical fluorescent labels include fluorescein isothiocyanate, rhodamine, phycoerythrin, phycocyanin, allophycocyanin, o-phthaldehyde, and fluorescamine.

Typical chemiluminescent compounds include luminol, isoluminol, aromatic acridinium esters, imidazoles, acridinium salts, and the oxalate esters. Typical bioluminescent compounds include luciferin, luciferase, and aequorin.

Typical enzyme labels include alkaline phosphatase, beta-galactosidase, glucose-6-phosphate dehydrogenase, maleate dehydrogenase, glucose oxidase, and peroxidase.

In one embodiment, a non-specific linker is included between the compound and the peptide to which it is conjugated. Such a linker is not involved in peptide activity. Rather the linker may serve as a spacer between the peptide and a functional moiety. Uses for a linker include immobilization of the peptide, such as to aid purification or detection. Alternatively, a linker may allow attachment of a compound to the peptide that enables specific delivery of the peptide to a particular target, such as a cell or tissue, spatially or temporally. When used as a vaccine, one or more of the peptides may be coupled to a linker that serves as a spacer between the peptide and an immunogenic carrier, or permits improved coupling between the peptide and the immunogenic carrier and prevents the formation of cryptic epitopes.

In one embodiment, one or more of the peptides are covalently coupled to an adjuvant (immunogenic carrier protein), such as diphtheria toxoid (DT), keyhole limpet hemocyanin (KLH), tetanus toxoid (TT) or the nuclear protein of influenza virus (NP), to increase their immunogenicity, using any of several conjugation chemistries known in the art. A non-specific linker can be present between the peptide and the immunogenic carrier and is preferably joined to the peptide or co-synthesised to facilitate coupling to the immunogenic carrier and/or to serve as a spacer between the peptide and the immunogenic carrier.

When used as a diagnostic agent, one or more of the peptides are preferably conjugated to an immunogenic carrier that was not previously used for vaccination. When monitoring the success of vaccination, this prevents the diagnostic agent from reacting to antibodies that were formed against the carrier fraction of the vaccine.

In one embodiment, the compound is an MHC class II molecule or peptide binding fragment thereof. The MHC class II molecule may be purified from a biological sample. Alternatively, the MHC class II molecule may be recombinantly produced. A peptide binding fragment of the MHC class II molecule can be obtained, for example, by enzymatic cleavage of the purified or recombinant intact molecule. Alternatively, the peptide binding fragment may be recombinantly produced. In a preferred embodiment, the compound is a recombinant two domain MHC class II molecule.

In their most basic form, the two domain MHC class II molecule comprises the αl and β1 domain of a mammalian MHC class II molecule wherein the amino terminus of the αl domain is covalently linked to the carboxy terminus of the β1 domain and wherein the polypeptide does not include the α2 or β2 domains. The two domain MHC class II molecule is associated by covalent or non-covalent interaction with a peptide defined herein. In certain embodiments, the peptide is covalently linked to the amino terminus of the β1 domain of the class II molecule. The two domain MHC class II molecule may also comprise a detectable label, such as a fluorescent label, or a toxin. Where the detectable label or toxin is to be covalently linked to the MHC molecule in a directed manner (i.e., rather than being randomly attached) it will generally be linked to the carboxy terminus of the molecule so as to minimise interference with the peptide antigen linked at the amino terminus.

In vitro, the two domain MHC class II molecule may be used to detect and quantify T-cells, and regulate T-cell function. Thus, such molecules loaded with a selected peptide may be used to detect, monitor and quantify the population of T cells that are specific for that peptide. The two domain MHC class II molecule/peptide conjugate may also be used to induce anergy of gluten-specific T-cells, alleviating symptoms associated with celiac disease. Alternatively, such molecules may be conjugated with a toxin to more directly kill the disease-causing T cells. Suitable toxins include protein toxins (for example, ricin, diphtheria, and *Pseudomonas* toxin), chemotherapeutic agents (for example, doxorubicin, daunorubicin, methotrexate, cytotoxin, and antisense RNA), antibodies to a cytotoxic T-cell surface molecule, lipases, and radioisotopes emitting "hard", for example, beta radiation.

Antigen Presenting Cells

The agent and/or peptides defined herein may be delivered by loading APCs with, for example, the first, second and third peptides, a biologically active fragment or variant of one or more thereof, and/or a polynucleotide encoding one or more thereof.

Preferably, the APCs are selected from the group consisting of dendritic cells, macrophages, B-lymphocytes and liver sinusoidal endothelial cells that express MHC class II molecules shared with the MHC phenotype of the subject. For example, the APCs may express HLA-DQ2 (for example, HLA DQA1*05 and HLA DQB1*02) and/or HLA DQ8. The APCs employed for this purpose may be isolated from the subject to whom they are to be delivered after loading, or they may be obtained from an allo-matched subject.

By "loading" an APC it is meant that the APC is incubated or transfected with the peptides, a biologically active fragment or variant of one or more thereof, or a polynucleotide encoding one or more thereof. Loading an APC can be achieved by using conventional nucleic acid transfection methods, such as lipid-mediated transfection, electroporation, and calcium phosphate transfection.

Peptide Production

The peptides can be prepared in any suitable manner. For example, the peptides can be recombinantly and/or synthetically produced.

The peptides may be synthesised by standard chemistry techniques, including synthesis by automated procedure using a commercially available peptide synthesiser. In general, peptide analogues are prepared by solid-phase peptide synthesis methodology which may involve coupling each protected amino acid residue to a resin support, preferably a 4-methylbenzhydrylamine resin, by activation with dicyclohexylcarbodiimide to yield a peptide with a C-terminal amide. Alternatively, a chloromethyl resin (Merrifield resin) may be used to yield a peptide with a free carboxylic acid at the C-terminal. After the last residue has been attached, the protected peptide-resin is treated with hydrogen fluoride to cleave the peptide from the resin, as well as deprotect the side chain functional groups. Crude product can be further purified by gel filtration, high pressure liquid chromatography (HPLC), partition chromatography, or ion-exchange chromatography.

If desired, and as outlined above, various groups may be introduced into the peptide of the agent during synthesis or during expression, which allow for linking to other molecules or to a surface. For example, cysteines can be used to make thioethers, histidines for linking to a metal ion complex, carboxyl groups for forming amides or esters, amino groups for forming amides, and the like.

The peptides may also be produced using cell-free translation systems. Standard translation systems, such as reticulocyte lysates and wheat germ extracts, use RNA as a template; whereas "coupled" and "linked" systems start with DNA templates, which are transcribed into RNA then translated.

Alternatively, the peptides may be produced by transfecting host cells with expression vectors that comprise a polynucleotide(s) that encodes one or more peptides.

For recombinant production, a recombinant construct comprising a sequence which encodes one or more of the peptides is introduced into host cells by conventional methods such as calcium phosphate transfection, DEAE-dextran mediated transfection, microinjection, cationic lipid-mediated transfection, electroporation, transduction, scrape lading, ballistic introduction or infection.

One or more of the peptides may be expressed in suitable host cells, such as, for example, mammalian cells (for example, COS, CHO, BHK, 293 HEK, VERO, HeLa, HepG2, MDCK, W138, or NIH 3T3 cells), yeast (for example, *Saccharomyces* or *Pichia*), bacteria (for example, *E. coli, P. pastoris*, or *B. subtilis*), insect cells (for example, baculovirus in Sf9 cells) or other cells under the control of appropriate promoters using conventional techniques. Following transformation of the suitable host strain and growth of the host strain to an appropriate cell density, the cells are harvested by centrifugation, disrupted by physical or chemical means, and the resulting crude extract retained for further purification of the peptide or variant thereof.

Suitable expression vectors include, for example, chromosomal, non-chromosomal and synthetic polynucleotides, for example, derivatives of SV40, bacterial plasmids, phage DNAs, yeast plasmids, vectors derived from combinations of plasmids and phage DNAs, viral DNA such as vaccinia viruses, adenovirus, adeno-associated virus, lentivirus, canary pox virus, fowl pox virus, pseudorabies, baculovirus, herpes virus and retrovirus. The polynucleotide may be introduced into the expression vector by conventional procedures known in the art.

The polynucleotide which encodes one or more peptides may be operatively linked to an expression control sequence, i.e., a promoter, which directs mRNA synthesis. Representative examples of such promoters include the LTR or SV40 promoter, the *E. coli* lac or trp, the phage lambda PL promoter and other promoters known to control expression of genes in prokaryotic or eukaryotic cells or in viruses. The expression vector may also contain a ribosome binding site for translation initiation and a transcription terminator.

The expression vectors may also include an origin of replication and a selectable marker, such as the ampicillin resistance gene of *E. coli* to permit selection of transformed cells, i.e., cells that are expressing the heterologous polynucleotide. The nucleic acid molecule encoding one or more of the peptides may be incorporated into the vector in frame with translation initiation and termination sequences.

One or more of the peptides can be recovered and purified from recombinant cell cultures (i.e., from the cells or culture medium) by well known methods including ammonium sulphate or ethanol precipitation, acid extraction, anion or cation exchange chromatography, phosphocellulose chromatography, hydrophobic interaction chromatography, affinity chromatography, hydroxyapatite chromatography, lectin chromatography, and HPLC. Well known techniques for refolding proteins may be employed to regenerate active conformation when the peptide is denatured during isolation and or purification.

To produce a glycosylated peptide, it is preferred that recombinant techniques be used. To produce a glycosylated peptide, it is preferred that mammalian cells such as, COS-7 and Hep-G2 cells be employed in the recombinant techniques.

The peptides can also be prepared by cleavage of longer peptides, especially from food extracts.

Pharmaceutically acceptable salts of the peptides can be synthesised from the peptides which contain a basic or acid moiety by conventional chemical methods. Generally, the salts are prepared by reacting the free base or acid with stoichiometric amounts or with an excess of the desired salt-forming inorganic or organic acid or base in a suitable solvent.

Methods of Identifying Bioactive Sequences

Disclosed herein are novel epitope sequences generated by novel methods of epitope discovery and generation disclosed herein. In one embodiment, a method of generating novel epitope sequences involves discovery of continuous epitope sequences on a polypeptide capable of binding to antibodies or illiciting an immune response in an individual. Once epitope sequences are discovered, they are recombined with random sequences or other discovered epitope sequences to generate new synthetic polypeptide sequences with greater sensitivity and specificity for binding to antibodies associated with an autoimmune disorder than the native epitopes alone. In preferred embodiments, the process of generating and screening sequences is performed on a peptide array that is configured to contact a sample.

Figure 2:
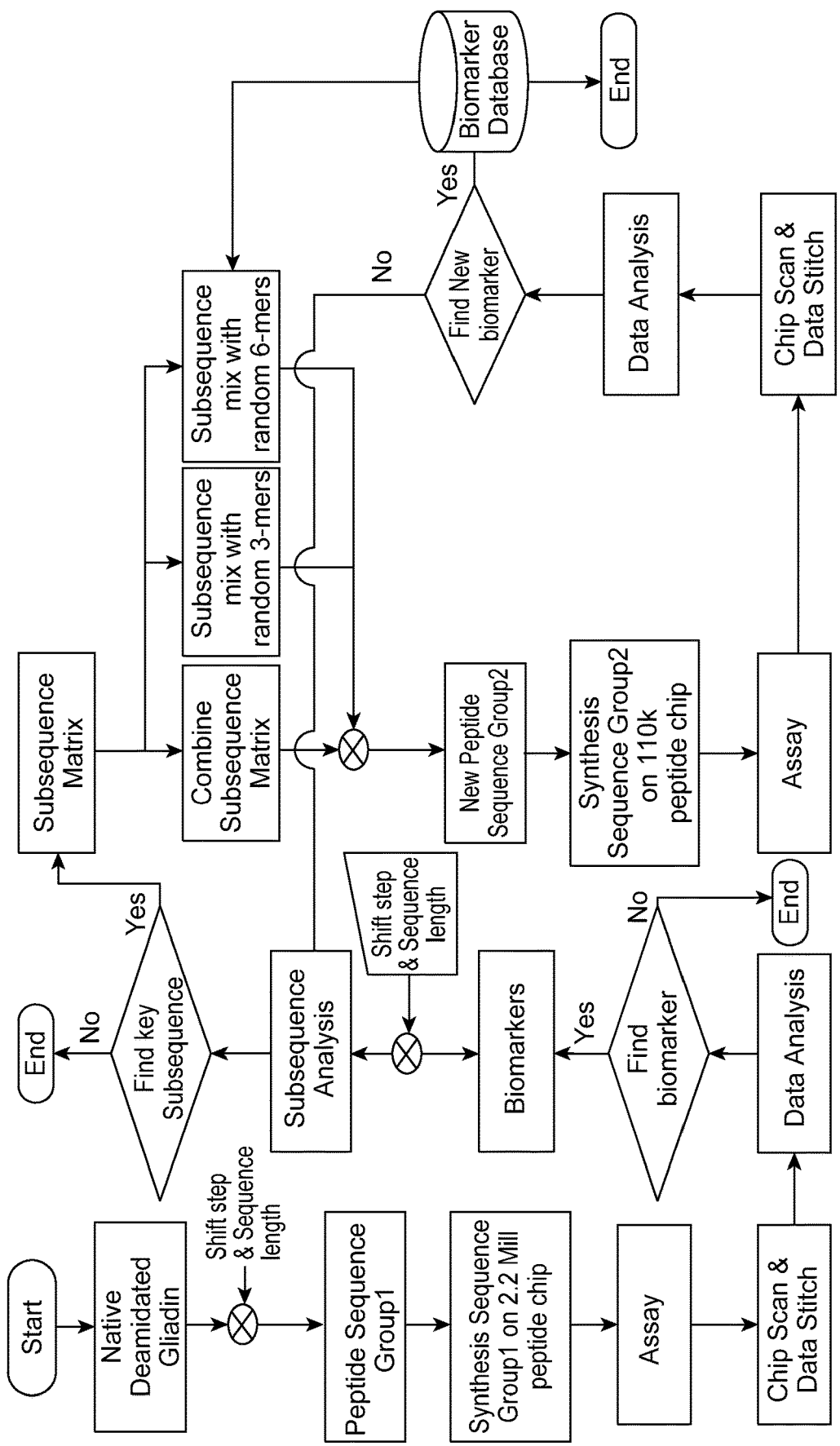
FIG. 2 shows a flow chart for biomarker selection, training and validation set analysis, according to an embodiment. Deamidated sequences of alpha, beta, gamma, or omega gliadins were synthesized on a 2.2M peptide microarray. A set of samples were run to determine key biomarkers with high significance to differentiate positives from negatives. Key subsequences were identified and a matrix formed to in-silico combine the best combination of 3-mers with random 3-mers and 6-mers. These sequences were then synthesized on a 110 k peptide microarray with an improved sensitivity and specificity and was validated using a blind set.

In some embodiments, as illustrated in FIG. 2, the method of identifying novel epitopes comprises the steps of: 1) generating a first plurality of overlapping polypeptide fragments each comprising portion of a native active protein or polypeptide that shows biological activity; 2) determining specificity and sensitivity of antibodies correlated with an autoimmune disorder to each polypeptide fragment by contacting an array comprising the polypeptide fragments with a sample from a subject having the autoimmune disorder; 3) selecting polypeptide fragments that exceed a pre-defined threshold value for sensitivity and/or specificity of binding, or have the greatest values of sensitivity and/or specificity of the collection of polypeptide fragments; 4) identifying from the polypeptide fragments identified in Step 3 the occurrence of epitope sequences within the polypeptide fragments; 5) generating a second plurality of synthetic polypeptides each comprising at least two of the epitope sequences in step 4, and optionally containing at least one random polypeptide sequence; 6) determining the specificity and sensitivity for each of the synthetic polypeptides generated in step 5 by contacting an array comprising the synthetic polypeptide fragments with a sample from a subject having the immune disorder; and 7) selecting synthetic polypeptides from step 6 exceeding a specificity and sensitivity threshold to use as biomarkers for the autoimmune disorder. Optionally, steps 5 through 7 may be repeated to further refine the sensitivity and/or specificity of the synthetic polypeptides to binding of an antibody associated with an autoimmune disorder. This method results in the generation of a plurality of novel bioactive polypeptides useful for diagnosis and treatment of an autoimmune disorder (e.g., celiac disease).

In one embodiment, the autoimmune disorder is celiac disease. In one embodiment, the protein having biological activity is a gliadin. In one embodiment, the gliadin is an α-gliadin, β-gliadin, γ-gliadin, or ω-gliadin.

Identification of Epitopes in on an Antigen

As disclosed herein, methods of identifying epitopes on a bioactive protein, such as gliadin, are provided and used for generation of novel bioactive polypeptide sequences for use in diagnosis and treatment of an autoimmune disease. In one embodiment, a full length bioactive polypeptide sequence is divided into overlapping polypeptide fragments of a discrete length. In one embodiment, each polypeptide fragment is from 6 to 15 amino acids in length. In one embodiment, each polypeptide fragment is 6, 7, 8, 9, 10, 11, 12, 13, 14, or 15 amino acids in length. In a preferred embodiment, each polypeptide fragment is 12 amino acids in length. The amount of overlap between polypeptide fragments of the full length bioactive polypeptide can be determined by step size between the polypeptide fragments, indicating the distance between each N-terminal or C-terminal amino acid of each polypeptide fragment as determined by the full length bioactive polypeptide. A diagram of an embodiment with a step size of 2 amino acids is shown in FIG. 1 with a polypeptide fragment length of 12 amino acids. This results in an overlap of 10 amino acids between neighboring polypeptide fragments. The overlap allows more precise determination of active epitope sequences on the bioactive polypeptide sequence. In some embodiments, the step size may vary, e.g., the step size may be 1, 2, 3, 4, 5, 6, 7, 8, 9, 10, 11, or 12 amino acids. In a preferred embodiment, the step size is 2 amino acids. One amino acid step size may also be used to improve precision at the cost of requiring generation of more fragment polypeptides.

Based upon the scheme of generation of polypeptide fragments discussed above, fragment polypeptides are synthesized on an array for screening against a sample with antibodies correlated with an autoimmune disorder. Binding of antibodies to fragment polypeptides on the array is detected via secondary antibody, although other methods of detection known to one of skill in the art will also suffice. Information about the binding of each polypeptide fragment to an antibody in a samples from a subject identified as having or not having the autoimmune disorder are compared to determine sensitivity and specificity of each peptide. Overlapping regions allow identification of epitope sequences. In one embodiment, the identified epitopes are from 3 to 11 amino acids in length. In one embodiment, each identified epitope is 3, 4, 5, 6, 7, 8, 9, 10, or 11 amino acids in length. In one preferred embodiment, each epitope is limited to 3 amino acids in length. In some embodiments, epitope pairs are identified in polypeptide fragments above a threshold of specificity and/or sensitivity of binding to autoimmune-positive samples. These epitope pairs are then used to generate synthetic sequences as described below.

Generation of Novel Bioactive Sequences

Using the epitopes identified from the native bioactive polypeptides described above, novel synthetic bioactive polypeptide sequences are generated and synthesized on an array for further screening. In one embodiment, each novel synthetic bioactive polypeptide comprises at least one epitope identified by the methods disclosed herein. In another embodiment, each novel synthetic bioactive polypeptide comprises at least two epitopes identified by the methods disclosed herein. In some embodiments, each novel synthetic bioactive polypeptide comprise two, three, four, or five epitopes identified by the method described herein. In some embodiments, each novel synthetic bioactive polypeptide comprises a randomly generated polypeptide sequence in addition to at least one or at least two epitope sequences. In some embodiments, the randomly generated sequence is 3, 6, 9, or 12 amino acids in length. IN a preferred embodiment, each novel synthetic bioactive polypeptide sequence comprise two 3 amino acid epitope sequences identified by the method disclosed herein, and at least one randomly generated polypeptide sequence to generate a 12 amino acid novel synthetic bioactive polypeptide sequence. In one embodiment, the novel synthetic bioactive polypeptide sequence is selected from SEQ ID NO: 1-127. In one embodiment, a plurality of novel synthetic bioactive polypeptide sequences is synthesized on an array for contact with a sample to determine sensitivity and specificity of each novel synthetic bioactive polypeptide sequence for detection of a sample with an autoimmune disorder. In one embodiment, novel synthetic bioactive polypeptides with a high sensitivity and/or specificity for detection of an autoimmune disorder are selected for further modification of random polypeptide sequence around the epitopes contained therein for screening on another polypeptide array. The methods described herein result in the generation of bioactive polypeptide sequences that act as epitopes for binding to an antibody associated with an autoimmune disease having a high sensitivity and/or specificity.

In one embodiment, a polypeptide array is generated with a plurality of synthetic bioactive polypeptide sequence provided herein. In one embodiment, the array has at least 4, 5, 6, 7, 8, 9, 10, 20, 30, 40, 50, 60, 70, 80, 90, or 100 novel synthetic bioactive polypeptide sequences generated by the methods disclosed herein. In one embodiment, the array has at least 4, 5, 6, 7, 8, 9, 10, 20, 30, 40, 50, 60, 70, 80, 90, or 100 polypeptides with a sequence selected from the group consisting of SEQ ID NO: 1-127. In one embodiment, the polypeptide array has a sensitivity of detection of an autoimmune disorder in a subject suspected of having the autoimmune disorder of greater than 90%, 91%, 92%, 93%, 94%, 95%, 96%, 97%, 98%, or 99%. In one embodiment, the polypeptide array has a specificity of detection of an autoimmune disorder in a subject suspected of having the autoimmune disorder of greater than 90%, 91%, 92%, 93%, 94%, 95%, 96%, 97%, 98%, or 99%.

Bioactive Sequences and Methods of Use for Treatment

Vaccines and Administration

The invention also provides a vaccine comprising the first, second and third peptides, a biologically active fragment or variant of one or more thereof, and/or a polynucleotide encoding one or more thereof. Also provided is a vaccine comprising a peptide of the invention and/or a polynucleotide of the invention.

As used herein, the term "vaccine" refers to a composition comprising or encoding peptides that can be administered to a subject sensitive to gluten to modulate the subject's response to gluten. The vaccine may reduce the immunological reactivity of a subject towards gluten. Preferably, the vaccine induces tolerance to gluten.

Administration of the vaccine to a subject may induce tolerance by clonal deletion of gluten-specific effector T cell populations, for example, gluten-specific $CD4^+$ T cells, or by inactivation (anergy) of said T cells such that they become less responsive, preferably, unresponsive to subsequent exposure to gluten (or peptides thereof).

Alternatively, or in addition, administration of the vaccine may modify the cytokine secretion profile of the subject (for example, result in decreased IL-4, IL-2, TNFα and/or IFN-γ, and/or increased IL-10). The vaccine may induce suppressor T cell subpopulations, for example Treg cells, to produce IL-10 and/or TGFβ and thereby suppress gluten-specific effector T cells.

The vaccine of the invention can be used for prophylactic treatment of a subject capable of developing sensitivity to gluten, for example, diagnosed as carrying the HLA-DQ2 and/or HLA-DQ8 gene and/or ongoing treatment of a subject who is sensitive to gluten, for example, a subject who has celiac disease. There is considerable animal data to support the prophylactic activity of immunodominant peptides for various autoimmune and model immune conditions, for example, experimental allergic encephalitis.

As used herein, the term "treatment" includes abrogating, inhibiting, slowing, or reversing the progression of a disease or condition, or ameliorating or preventing a clinical symptom of the disease (for example, celiac disease) or condition.

The amount of vaccine (or agent, peptide, polynucleotide and/or APC) to be administered is referred to as the "effective amount". The term "effective amount" means the amount sufficient to provide the desired therapeutic or physiological effect when administered under appropriate or sufficient conditions. Single or multiple doses may be administered. Undesirable effects, for example, side effects, are sometimes manifested along with the desired therapeutic effect; hence, a practitioner balances the potential benefits against the potential risks in determining an appropriate "effective amount". The exact amount required will vary from subject to subject, depending on the species, age, size and general condition of the subject, mode of administration and the like. Thus, it may not be possible to specify an exact "effective amount". However, an appropriate "effective amount" in any individual case may be determined by one of ordinary skill in the art using only routine experimentation.

The vaccine (or agent, peptide, polynucleotide and/or APC) modifies the T cell response to wheat, barley and rye in the subject, and preferably wheat, barley, rye and oats, as represented by gliadin, secalin, *hordein*, glutenin and optionally avedin proteins. Thus, a subject treated according to the invention preferably is able to eat at least wheat, rye, barley and optionally oats without a significant T cell response which would normally lead to symptoms of celiac disease.

The individual components of an agent of the invention may be administered in the same composition or in different compositions or a combination thereof (for example, the first and second peptide defined herein in one composition, and the third peptide in a separate composition). If in different compositions, they may be administered simultaneously or sequentially.

The agent or vaccine may include a pharmaceutically acceptable carrier. The term "pharmaceutically acceptable carrier" refers to molecular entities and compositions that do not produce an allergic, toxic or otherwise adverse reaction when administered to a subject, particularly a mammal, and more particularly a human. The pharmaceutically acceptable carrier may be solid or liquid. Useful examples of pharmaceutically acceptable carriers include, but are not limited to, diluents, excipients, solvents, surfactants, suspending agents, buffering agents, lubricating agents, adjuvants, vehicles, emulsifiers, absorbants, dispersion media, coatings, stabilizers, protective colloids, adhesives, thickeners, thixotropic agents, penetration agents, sequestering agents, isotonic and absorption delaying agents that do not affect the activity of the active agents of the invention.

The carrier can be any of those conventionally used and is limited only by chemico-physical considerations, such as solubility and lack of reactivity with the active agent, and by the route of administration. Suitable carriers for this invention include those conventionally used, for example, water, saline, aqueous dextrose, lactose, Ringer's solution, a buffered solution, hyaluronan, glycols, starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like. Liposomes may also be used as carriers.

Techniques for preparing pharmaceutical compositions are generally known in the art as exemplified by Remington's Pharmaceutical Sciences, 16th Ed. Mack Publishing Company, 1980.

The term "adjuvant" generally refers to an immunostimulatory substance designed to enhance the immunogenicity of one or more peptides defined herein. Preferably, the adjuvant does not produce a Th1 response and further, promotes immune tolerance and/or reduces inflammation. Suitable adjuvants include 1) an aluminium-based mineral salt adjuvant, for instance an $Al(OH)_3$ gel or aluminium phosphate, but may also be a salt of calcium, iron or zinc; and 2) dexamethasone (Kang et al., 2008).

Administered may be orally, topically (percutaneous), parenterally, by inhalation spray or rectally in dosage unit formulations containing conventional non-toxic pharmaceutically acceptable carriers. The term "parenteral", as used herein includes intravenous, intraarterial, intraperitoneal, intramuscular, subcutaneous, subconjunctival, intracavity, transdermal and subcutaneous injection, aerosol for administration to lungs or nasal cavity, or administration by infusion by, for example, osmotic pump.

The active compounds of the invention may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to methods known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations.

Tablets

Tablets containing the active ingredient in admixture with pharmaceutically acceptable excipients may also be manufactured by known methods. The excipients used may be for example, (1) inert diluents such as calcium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous Suspensions

Aqueous suspensions normally contain the active materials in admixture with excipients suitable for the manufacture of aqueous suspensions. Such excipients may include: (1) suspending agents such as sodium carboxymethylcellulose, methylcellulose, hydroxypropylmethylcellulose, sodium alginate, polyvinylpyrrolidone, gum tragacanth and gum acacia; or (2) dispersing or wetting agents such as PEG esters of $C_2$-$C_{18}$ fatty acids, Tween 80 or polyethylene oxide sorbitan monooleate, Brij or polyoxyethylene alcohol, Triton-X or Polyethylene glycol p-isooctylphenyl ether, Triton-N, and Triton A-20 or 4-(1,1,3,3-Tetramethylbutyl) phenol, polymer with formaldehyde and oxirane, DECON, Tris or 2-amino-2-hydroxymethyl-1,3-propanediol and Cremophor EL.

The aqueous suspensions may also contain one or more preservatives, for example, ethyl or n-propyl p-hydroxybenzoate; one or more colouring agents; one or more flavouring agents; and one or more sweetening agents such as sucrose, aspartame or saccharin.

Oily Suspensions

Oily suspension may be formulated by suspending the active ingredient in a vegetable oil, for example *arachis* oil, olive oil, sesame oil or coconut oil, a fish oil which contains omega 3 fatty acid, or in a mineral oil such as liquid paraffin. The oily suspensions may contain a thickening agent, for example beeswax, hard paraffin or cetyl alcohol. Sweetening agents and flavouring agents may be added to provide a palatable oral preparation. These compositions may be preserved by the addition of an antioxidant such as ascorbic acid.

Dispersible Powders and Granules

Dispersible powders and granules are suitable for the preparation of an aqueous suspension. They provide the active ingredient in a mixture with a dispersing or wetting agent, a suspending agent and one or more preservatives. Suitable dispersing or wetting agents and suspending agents are exemplified by those already mentioned above. Additional excipients, for example, those sweetening, flavouring and colouring agents described above may also be present.

Emulsion

The pharmaceutical composition(s) may also be in the form of oil-in-water emulsions. The oily phase may be a vegetable oil such as olive oil or *arachis* oils, or a mineral oil such as liquid paraffin or a mixture thereof. Suitable emulsifying agents include gum acacia, gum tragacanth, soy bean, lecithin, polyoxyethylene oxide sorbitan monooleate (Tween 80). The emulsions may also contain sweetening and flavouring agents.

Syrups and Elixirs

Syrups and elixirs may be formulated with sweetening agents, for example, glycerol, propylene glycol, sorbitol, aspartame or sucrose. Such formulations may also contain a demulcent, preservative, flavouring and colouring agents.

Injectables

The pharmaceutical composition(s) may be in the form of a sterile injectable aqueous or oleagenous suspension. This suspension may be formulated according to known methods using those suitable dispersing or wetting agents and suspending agents which have been mentioned above. The sterile injectable preparation may be a suspension in a non-toxic parenterally-acceptable diluent or solvent, for example as a solution in 1,3-butanediol. Among the acceptable carriers that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. In addition, fatty acids such as oleic acid find use in the preparation of injectables.

Compositions suitable for parenteral administration include, but are not limited to, aqueous and non-aqueous sterile injection solutions. Examples of appropriate delivery mechanisms for subcutaneous administration include, but are not limited to, implants, depots, needles, capsules, and osmotic pumps.

Sustained Release Compositions

Sustained-release compositions may be prepared. Suitable examples of sustained-release preparations include semipermeable matrices of solid hydrophobic polymers which matrices are in the form of shaped articles, for example, films, or microcapsules. Examples of sustained-release matrices include polyesters, hydrogels (for example, poly(2-hydroxyethyl-methacrylate), or poly(vinylalcohol)), polylactides, copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods.

The active agent may be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

Microencapsulation for sustained release has been successfully performed with human growth hormone (rhGH), interferon (rhIFN), interleukin-2, and MN rgp120. The sustained-release formulations of these proteins were developed using PLGA polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition.

Gene Therapy

In a further embodiment, a polynucleotide encoding one or more peptides defined herein is inserted into a recombinant expression vector for the purposes of administration to the subject.

The term "recombinant expression vector" refers to a plasmid, virus or other vehicle known in the art that has been manipulated by insertion or incorporation nucleic acid encoding one or peptides. Such expression vectors contain a promoter sequence which facilitates the efficient transcription in the host of the inserted genetic sequence. The expression vector typically contains an origin of replication, a promoter, as well as specific genes which allow phenotypic selection of the transformed cells.

In one embodiment, the viral vector is derived from adeno-associated virus (AAV) and comprises a constitutive or regulatable promoter capable of driving sufficient levels of expression of the peptides defined herein. Preferably, the viral vector comprises inverted terminal repeat sequences of AAV, such as those described in WO 93/24641. In a preferred embodiment, the viral vector comprises polynucleotide sequences of the pTR-UF5 plasmid. The pTR-UF5 plasmid is a modified version of the pTR.sub.BS-UF/UF1/UF2/UFB series of plasmids (Zolotukiin et al., 1996; Klein et al., 1998).

Promoters useful with the subject invention include, for example, the cytomegalovirus immediate early promoter (CMV), the human elongation factor 1-α promoter (EF1), the small nuclear RNA promoters (U1a and U1b), α-myosin heavy chain promoter, Simian virus 40 promoter (SV40), Rous sarcoma virus promoter (RSV), adenovirus major late promoter, β-actin promoter and hybrid regulatory element comprising a CMV enhancer/β-actin promoter. These promoters have been shown to be active in a wide range of mammalian cells.

The promoters are operably linked with heterologous polynucleotide encoding one or more peptides defined herein. By "operably linked," it is intended that the promoter element is positioned relative to the coding sequence to be capable of effecting expression of the coding sequence.

Also contemplated for use with the vectors of the present invention are inducible and cell type specific promoters, for example, Tet-inducible promoters (Clontech, Palo Alto, Calif.) and VP16-LexA promoters (Nettelbeck et al., 1998).

Transcriptional enhancer elements which can function to increase levels of transcription from a given promoter can also be included in the vector Enhancers can generally be placed in either orientation, 3' or 5', with respect to promoter sequences. In addition to the natural enhancers, synthetic enhancers can be used in the present invention, for example, a synthetic enhancer randomly assembled from Spc5-12-derived elements including muscle-specific elements, serum response factor binding element (SRE), myocyte-specific enhancer factor-1 (MEF-1), myocyte-specific enhancer factor-2 (MEF-2), transcription enhancer factor-1 (TEF-1) and SP-1 (Li et al., 1999; Deshpande et al., 1997; Stewart et al., 1996; Mitchell and Tjian, 1989; Briggs et al., 1986; Pitluk et al., 1991) can be used in the vector.

The gene therapy methods can be performed by ex vivo or in vivo treatment of the patient's cells or tissues. Vectors can be introduced into suitable cells, cell lines or tissue using methods known in the art. The viral particles and vectors can be introduced into cells or tissue in vitro or in vivo. Methods contemplated include transfection, transduction, injection and inhalation, for example, vectors can be introduced into cells using liposomes containing the subject vectors, by direct transfection with vectors alone, electroporation or by particle bombardment.

Dosage

It is especially advantageous to formulate the active in dosage unit form for ease of administration and uniformity of dosage. "Dosage unit form" as used herein refers to physically discrete units suited as unitary dosages for the subject to be treated; each unit containing a predetermined quantity of active agent calculated to produce the desired therapeutic effect in association with the required pharmaceutical carrier. The specification for the dosage unit forms are dictated by and directly dependent on the unique characteristics of the active agent and the particular therapeutic effect to be achieved, and the limitations inherent in the art of compounding such an active agent for the treatment of subjects. Alternatively, the compositions may be presented in multi-dose form.

Examples of dosage units include sealed ampoules and vials and may be stored in a freeze-dried condition requiring only the addition of the sterile liquid carrier immediately prior to use.

The agent or vaccine may also be included in a container, pack, or dispenser together with instructions for administration.

The actual amount administered (or dose or dosage) and the rate and time-course of administration will depend on the nature and severity of the condition being treated. Prescription of treatment, for example, decisions on dosage, timing, frequency, etc., is within the responsibility of general practitioners or specialists (including human medical practitioner, veterinarian or medical scientist) and typically takes account of the disorder to be treated, the condition of the subject, the site of delivery, the method of administration and other factors known to practitioners. Examples of techniques and protocols can be found in Remington's Pharmaceutical Sciences, 18th Ed. (1990), Mack Publishing, Company, Easton, Pa., U.S.A.). The dose, dose frequency, duration, route of administration and need for maintenance therapy could be based upon the criteria for other peptide immunotherapeutics.

Effective amounts may be measured from ng/kg body weight to g/kg body weight per minute, hour, day, week or month.

When in vivo administration of an agent or vaccine of the invention is employed, normal dosage amounts may vary from about 10 ng/kg to up to 100 mg/kg of mammal body weight or more per day, preferably about 1 µg/kg/day to 10 mg/kg/day, depending upon the route of administration. Guidance as to particular dosages and methods of delivery is provided in the literature.

Toxicity and therapeutic efficacy of the agent or vaccine can be determined by standard pharmaceutical procedures in cell cultures or experimental animals by determining the $IC_{50}$ and the maximal tolerated dose. The data obtained from these cell culture assays and animal studies can be used to formulate a range suitable for humans.

Diagnosis and Efficacy of Treatment

The peptides defined herein are also useful as a diagnostic agent.

In one example, gluten tolerance is assessed by measuring IL-10 and/or TGFβ secreted from stimulated cells, for example, Treg cells, exposed to the peptides defined herein. Treg cells are characterised by their capacity to produce large amounts of IL-10 and TGFβ. IL-10 is considered to be one of the main cytokines involved in immunosuppression; a target for suppression seems to be the transcriptional control of IL-2 in effector cells.

In another example, gluten tolerance is assessed by measuring IFNγ secreted from stimulated cells, for example, gluten-specific $CD4^+$ T cells.

The diagnostic test may be performed in vitro using whole blood or cells isolated and/or fractionated therefrom.

In one example, the cells have been previously exposed to one or more of the peptides (either alone, conjugated to an MHC molecule or fragment thereof, or peptide loaded APC).

In another example, the cells are stimulated in vitro by coincubation with the peptides (either alone, conjugated to an MHC molecule or fragment thereof, or peptide loaded APC).

The direct T cell mediated effects of the agent can be monitored by functional assays utilising cells isolated from peripheral blood or tissue (for example, the small intestine). Effects of peptide administration down stream to cognate T cells could be assessed using immune cell types, tissues, biological fluids (for example, plasma, intestinal secretions, urine or stool).

In general the biological effects of peptides recognised by cognate T cells are either pro-inflammatory or tolerogenic, depending on the dose regimen, mode of administration and whether the peptides are modified or co-administered with another compound that has immunological properties, for example, an adjuvant. These and other peptides selected for use in peptide based therapeutic vaccines are generally short (<29 amino acids), aqueous-soluble, without innate immune effects and recognised by a substantial proportion of pathogenic T ells. Based upon observations in animal models of T cell mediated disease and in other human diseases, initial administration would be followed by activation of cognate T cells. However, repeated administration of the agent is expected to induce T cell anergy and/or tolerance. Ongoing regular peptide administration would be expected to maintain tolerance to gluten, suppress inflammation in the small intestine and inhibit pro-inflammatory gluten-specific T cells throughout the body.

Hence, the key marker of therapeutic success would be the absence of inflammation in the small intestine following deliberate gluten ingestion. Surrogate markers of immunity likely to predict normal or inflamed intestinal tissue after gluten ingestion includes a wide range of assays utilizing pure or crude mixtures of immune cells, biological fluids, or tissue samples, to measure soluble or cell-associated proteins or small molecules associated with immune activation, inflammation, or tolerance. These assays are well-known to immunologists, immuno-histologists, and clinicians familiar with immune diseases in rodents, humans, and in particular, celiac disease. Markers, more specifically, that assess the activity of celiac disease and gluten-induced immunity include small bowel histology, serum IgA and IgG specific gliadin (protein or peptide) and for various host proteins including tTG.

Generic and specific markers of immunity in celiac disease that might be adapted for use in monitoring the peptide immunotherapy for celiac disease or for diagnosis of celiac disease include the following:

(a) Direct effects of peptides on the CD4+ T cell isolated from blood or tissue can be monitored ex vivolin vitro by peptide-stimulated cytokine release, T-cell proliferation, or determination of CD4+ T cell markers that may be altered in vivo.

(b) The frequency and phenotype of individual CD4+ T cells specific for the peptides or gluten generally can be assessed by direct enumeration of cells, for example, by FACS analysis. Oral ingestion of gluten in patients with celiac disease normally following a gluten free diet is known to stimulate T cells specific for the peptides and gluten generally. A clinical test such as gluten challenge may be used to assess the T cells induced in blood or other tissues. The phenotype of isolated T cells could then be assessed fresh or following short-term expansion in vitro. Assays of T cells may rely upon MHC-peptide complexes, antigen-stimulated intracellular cytokine, or other cell surface markers induced on antigen-activated T cells. Functional status of CD4+ T cells is correlated with the presence of various cell-surface and intra-cellular markers, for example, activation markers including CD25 and CD69, or of "tolerance" and regulatory T cell function, for example, GITR and FOXP3. Production of cytokines such as IFNγ, IL-4, IL-5 and IL-13, and of IL-17 would be considered pro-inflammatory for classic Th1, Th2 or Th17 pro-inflammatory immune responses. In contrast, secretion of IL-10 and TGFβ are associated with tolerogenic immune responses. It would be expected markers of pro-inflammatory immune responses would decline and/or markers of tolerogenic immune responses would strengthen.

(c) Effects of peptides on CD4+ T cells can also be measured using mixtures of cells, for example, whole blood, PBMC, mononuclear cells isolated from tissue, or using tissue incubated with the peptides. Assays capable of measuring individual or multiple proteins or RNA encoding relevant immunological or disease-associated proteins such as cytokines and chemokines could be assessed after short-term incubation with the peptides. Assays such as IFN-γ ELISpot using PBMC before and or after administration of gluten or peptides themselves to the patient, or multiplex assays of chemokines and cytokines using PBMC are capable of detecting the biological effects of peptide-specific T cells from patients. The therapeutic effect of the peptides would be indicated by a shift from markers associated with pro-inflammatory immune responses to markers associated with immune tolerance (for example, IL-10) and general reduction in pro-inflammatory markers such as IFN-γ.

(d) Effects of peptides on tissue may be practical; functional assays could take the form of direct application of peptide to the skin to assess delayed-type hypersensitivity, as in the Mantoux test for tuberculosis, which involves intra-dermal application of PPD (purified protein derivative) and assessment of the diameter of redness at the injection site 24-72 h later. The peptides may also be applied to other mucosal and skin sites to assess in the same manner. In clinical practice, it is both the peptide and grain derived protein-stimulated immune response that is important in celiac disease. For example, it is predicted that immunotherapy using the selected peptides would not only lead to suppression of the immune response stimulated by T cells specific for the peptides but also "tolerance" would be "infectious" and also lead to suppression of pro-inflammatory immunity to other gluten-derived peptides and gluten itself. Hence, the effects of the peptide therapy could also be monitored using gluten from various grains (wheat, rye, barley) in celiac disease, in place of peptide in the assays described above. Indeed, peptide therapy for cat-sensitive asthma has been monitored by such a skin test utilizing the whole protein antigen from which the therapeutic peptides are derived (Oldfield et al., 2002).

(e) Ultimately, the clinical effects of the peptide immunotherapy would be assessed by histologic examination of tissues exposed to dietary gluten, typically the small bowel, but in experimental settings oral and rectal mucosa have also bee assessed, and in principle other sites such as oesophagus and colon might also be assessed. Tissue from these sites could be collected by direct visualization, typically by endoscopic biopsy. Direct visualization by endoscopy has also been used to diagnose celiac disease according to the appearance of the mucosa-villous atrophy can be assessed by standard as well as magnifying and capsule endoscopy. Hence, the tolerogenic effects of the peptides may be assessed simply by detection of macroscopic tissue damage in the gastrointestinal tract.

(f) Immunoglobulin specific for the peptides or other gluten peptides, or autoantigens relevant to celiac disease would provide markers of gluten immunity relevant to disease activity, and to opsonising activity that may compromise the therapeutic effects of the peptides themselves.

(g) Presence of markers associated with anaphylaxis, such as peptide- or gluten-specific IgE or histamine release by peripheral blood basophils may also be used to predict complications of peptide immunotherapy and need to adjust or cease therapy.

Food Test

The invention also provides a method of determining whether a composition or food is capable of causing celiac disease, the method comprising detecting the presence of the agent of the invention, the peptide of the invention and/or the polynucleotide of the invention in the composition or a food sample. Typically this is performed by using a binding assay in which one or more compounds which bind one or more peptides defined herein in a specific manner is contacted with the composition and the formation of peptide/compound complex(es) is detected and used to ascertain the presence of the peptide(s). In one example, the compound is an antibody. Any suitable format of binding assay can be used. Typically, the assay utilises monoclonal antibodies to gluten peptides in a non-competitive, sandwich type ELISA. Food samples may first be extracted, optionally diluted and then tested in the assay.

The composition or food typically comprises material from a plant that expresses gluten. Such material may be a plant part, such as a harvested product (for example, seed). The material may be processed products of the plant material, such as a flour or food that comprises gluten. The processing of food material and testing in suitable binding assays is routine (see for example, Kricka, 1998). The composition or food material may be treated with tTG prior to being contacted with the compound.

In one embodiment, the composition or food material is contacted with at least 2, 3, 5, 10 or more antibodies which are specific for peptides defined herein in deamidated and/or non-deamidated form. Preferably, the antibodies are directed against sequences that are protease resistant and allow for the detection of α, β, γ and ω gliadins, and LMW and HMW glutenins in wheat, B, C and D hordeins in barley, β, γ and ω secalins in rye, and optionally avenins in oats.

Antibodies directed against the peptides/epitopes defined herein may be provided in kit form for use in an assay for the detection and/or quantification of gluten in foods.

Protease Identification

The present invention also provides a method of identifying a protease that can cleave a peptide as defined herein, the method comprising contacting the peptide with a protease under conditions to effect specific cleavage of the peptide to produce a proteolytic product and detecting the proteolytic product produced. In one example, the proteolytic product is detected, for example, using SDS-PAGE, HPLC, ELIZA, or Western Blot. In a further example, the peptide is fused to a fluorescent donor and a quenching acceptor so as to enable intramolecular resonance energy transfer between the fluorescent donor and the quenching acceptor. Upon cleavage, the donor and acceptor are separated, allowing detection of the donor's fluorescent emission. Typically the peptide separates the fluorescent donor and the quenching acceptor at a distance of less than about 100 angstroms. The fluorescent donor can be attached to the peptide's C-terminus, and the quenching acceptor can be attached to the peptide's N-terminus, or vice versa.

Methods of Use of Arrays with Bioactive Sequences

Any of the arrays described herein can be used as a research tool or in a research application. In one aspect, arrays can be used for high throughput screening assays. For example, enzyme substrates (i.e., peptides on a peptide array described herein) can be tested by subjecting the array to an enzyme and identifying the presence or absence of enzyme substrate(s) on the array, e.g., by detecting at least one change among the features of the array.

Arrays can also be used in screening assays for ligand binding, to determine substrate specificity, or for the identification of peptides that inhibit or activate proteins. Labeling techniques, protease assays, as well as binding assays useful for carrying out these methodologies are generally well-known to one of skill in the art.

In some embodiments, an array can be used to represent a known protein sequence as a sequence of overlapping peptides. For example, the amino acid sequence of a known protein is divided into overlapping sequence segments of any length and of any suitable overlapping frame, and peptides corresponding to the respective sequence segments are in-situ synthesized as disclosed herein. The individual peptide segments so synthesized can be arranged starting from the amino terminus of the known protein.

In some embodiments, an array is used in a method wherein the antigenic representation of the array includes at least one region where the whole antigen sequence of a known protein is spanned via epitope sliding; the immunoactive regions of the antigen are determined by contacting one or more clinical samples on the array or a plurality of different arrays, and the set of peptide sequences required to represent the known protein antigen are reduced.

In some embodiments, a sample is applied to an array having a plurality of random peptides. The random peptides can be screened and BLASTed to determine homologous domains with, e.g., a 90% or more identity to a given antigenic sequence. In some aspect, the whole antigenic sequence can then be synthesized and used to identify potential markers and/or causes of a disease of interest.

In some embodiments, an array is used for high throughput screening of one or more genetic factors. Proteins associated with a gene can be a potential antigen and antibodies against these gene related proteins can be used to estimate the relation between gene and a disease.

In another example, an array can be used to identify one or more biomarkers. Biomarkers can be used for the diagnosis, prognosis, treatment, and management of diseases. Biomarkers may be expressed, or absent, or at a different level in an individual, depending on the disease condition, stage of the disease, and response to disease treatment. Biomarkers can be, e.g., DNA, RNA, proteins (e.g., enzymes such as kinases), sugars, salts, fats, lipids, or ions.

Arrays can also be used for therapeutic purposes, e.g., identifying one or more bioactive agents. A method for identifying a bioactive agent can comprise applying a plurality of test compounds to an array and identifying at least one test compound as a bioactive agent. The test compounds can be small molecules, aptamers, oligonucleotides, chemicals, natural extracts, peptides, proteins, fragment of antibodies, antibody like molecules or antibodies. The bioactive agent can be a therapeutic agent or modifier of therapeutic targets. Therapeutic targets can include phosphatases, proteases, ligases, signal transduction molecules, transcription factors, protein transporters, protein sorters, cell surface receptors, secreted factors, and cytoskeleton proteins.

In another aspect, an array can be used to identify drug candidates for therapeutic use. For example, when one or more epitopes for specific antibodies are determined by an assay (e.g., a binding assay such as an ELISA), the epitopes can be used to develop a drug (e.g., a monoclonal neutralizing antibody) to target antibodies in disease.

In one aspect, also provided are arrays for use in medical diagnostics. An array can be used to determine a response to administration of drugs or vaccines. For example, an individual's response to a vaccine can be determined by detecting the antibody level of the individual by using an array with peptides representing epitopes recognized by the antibodies produced by the induced immune response. Another diagnostic use is to test an individual for the presence of biomarkers, wherein samples are taken from a subject and the sample is tested for the presence of one or more biomarkers.

Arrays can also be used to stratify patient populations based upon the presence or absence of a biomarker that indicates the likelihood a subject will respond to a therapeutic treatment. The arrays can be used to identify known biomarkers to determine the appropriate treatment group. For example, a sample from a subject with a condition can be applied to an array. Binding to the array may indicate the presence of a biomarker for a condition. Previous studies may indicate that the biomarker is associated with a positive outcome following a treatment, whereas absence of the biomarker is associated with a negative or neutral outcome following a treatment. Because the patient has the biomarker, a health care professional may stratify the patient into a group that receives the treatment.

In some embodiments, a method of detecting the presence or absence of a protein of interest in a sample can include obtaining an array disclosed herein and contacted with a sample suspected of comprising the protein of interest; and determining whether the protein of interest is present in the sample by detecting the presence or absence of binding to one or more features of the array.

In some embodiments, a method of identifying a vaccine candidate can include obtaining an array disclosed herein contacted with a sample derived from a subject previously administered the vaccine candidate, wherein the sample comprises a plurality of antibodies; and determining the binding specificity of the plurality of antibodies to one or more features of the array. In some embodiments, the features comprise a plurality of distinct, nested, overlapping peptide chains comprising subsequences derived from a source protein having a known sequence.

In one embodiment, a method of diagnosing and treating an autoimmune disorder is provided. In one embodiment, use of the peptide chip to detecting multiplex antibodies in a serum sample is provided. In some embodiments, this method is performed in a single assay. In some embodiments, this method is performed on a single peptide chip. In one embodiment, this method provides the ability to detect multiple chemokines from an autoimmune disorder. In one embodiment, this method provides the ability to identify the subtype and severity of an autoimmune disorder.

In one embodiment, methods of diagnosing using the peptide chip have a reproducibility of $R^2$ greater than 0.95. In some embodiments, the methods of diagnosing an autoimmune disorder using the peptide chip have a specificity of greater than 0.99 and/or a sensitivity of greater than 0.99.

In one embodiment, the autoimmune disorder is celiac disease. In another embodiment, the autoimmune disorder is lupus erythematosis. In another embodiment, the autoimmune disorder is rheumatoid arthritis.

The peptide array disclosed herein may be used to identify epitopes related to autoimmune diseases. In one embodiment, the epitopes are B cell epitopes, T cell epitopes, or epitopes related to inflammatory response (e.g., TNF). Epitopes related to inflammatory response may be identified by the present invention using a cytokine assay. In one embodiment, the peptide sequences identified by this cytokine assay may be used in immunosuppressive vaccines. In other embodiments, the peptide sequences may be used as part of a peptide array to identify the presence of inflammatory molecules in a subject suspected of having an inflammatory disorder, e.g., an autoimmune disorder. In one embodiment, the peptide array may be used to identify B cell epitopes. In this embodiment, epitopes binding to antibodies from a sample associated with an autoimmune disorder are identified. These peptides are then used on another peptide array useful for diagnosis of an autoimmune disorder. In one embodiment, diagnosis of an autoimmune disorder includes identification of autoimmune disorder subtype. In some embodiments, the identified B cell epitopes are used to measure a patient's response to treatment of an autoimmune disorder. In one embodiment, T cell epitopes may be identified by the present invention using an MHC complex assay (e.g., a human leukocyte antigen assay). Epitopes identified as interacting with the MHC complex in a subject identified as having an autoimmune disorder may be used for treatment of the autoimmune disorder. Such peptides may be useful in a vaccine or other drugs for T cell regulation. A flow chart depicting the identification of epitope sequences and their use, according to several embodiments of the invention, is shown in FIG. 3.

In some embodiments the invention includes bioinformatic analysis of data to, e.g., identify informative subsequences, and subsequent synthesis and testing of synthetic peptide sequences useful for diagnosing a condition. These bioinformatic methods are carried out, in part, using a computer to accomplish one or more of the following steps: 1) generating subsequences from longer sequences; 2) tabulating and ranking the occurrence of subsequences in positive hits from samples bound to arrays of tiled naturally-occurring peptide sequences; 3) analyzing hits to arrays comprising synthetic sequences that include informative subsequences.

Unless specifically stated otherwise as apparent from the following discussion, it is appreciated that throughout the description, discussions utilizing terms such as "processing" or "computing" or "calculating" or "determining" or "displaying" or "analyzing" or "comparing" or "identifying" or the like, refer to the action and processes of a computer system, or similar electronic computing device, that manipulates and transforms data represented as physical (electronic) quantities within the computer system's registers and memories into other data similarly represented as physical (electronic) quantities within the computer system's registers and memories into other data similarly represented as physical quantities within the computer system memories or registers or other such information storage, transmission or display devices.

The present invention also relates to system apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

Various general purpose systems may be used with programs in accordance with the teachings herein, or it may prove convenient to construct more specialized apparatus to perform the required method procedures. The required structure for a variety of these systems will appear from the description below. In addition, the present invention is not described with reference to any particular programming language. It will be appreciated that a variety of programming languages may be used to implement the teachings of the invention as described herein.

Compositions

Formulations

Disclosed herein are formulations such as photoactive formulations (e.g., photoresist formulations), coupling formulations, and linker formulations. These formulations can be useful in the manufacture and/or use of, e.g., substrates and/or peptide arrays disclosed herein. Generally the components of each formulation disclosed herein are soluble in water at room temperature (app. 25° C.).

Photoactive Formulations

Disclosed herein are photoactive formulations. In one aspect, a photoactive formulation can include a chemical amplification resist formulation. In chemical amplification (CA) resists, the primary photochemical event produces a mobile catalyst that, typically during later postexposure baking (PEB), goes on to induce a cascade of material transforming secondary catalytic events within a 5-25 nm radius. Such chemical amplification thus makes possible an overall quantum yield (the number of material reactions divided by number of absorbed photons) of up to several hundred. A CA resist typically contains a small amount (app. 1-5% by weight) of radiation-sensitive catalyst precursor, e.g., a photoacid generator (PAG); a plurality of chemical groups that can react by elimination, addition, or rearrangement in the presence of catalyst; a polymer matrix able to disperse other components in a smooth clear film; and optional additives to improve performance or processability, e.g., surfactants, photosensitizers, and etch resistors.

In one aspect, a photoactive coupling formulation can include a photoactive compound. Photoactive compounds may include photobase or photoacid generators. Exposure of the photoactive compounds to electromagnetic radiation is a primary photochemical event that produces a compound that goes on to induce material transforming secondary reactions within a diffusion-limited radius. A photoactive coupling formulation may comprise a photoactive compound comprising a radiation-sensitive catalyst precursor, e.g., a photoacid generator (PAG); a plurality of chemical groups that can react by elimination, addition, or rearrangement in the presence of catalyst; and optional additives to improve performance or processability, e.g., surfactants, photosensitizers, and etch resistors.

In some embodiments, a photoactive coupling formulation includes a photobase generator and a photo sensitizer in a polymer matrix dispersed in a solvent. In some embodiments, the polymer in the composition of the photoresist is generally inert and non-crosslinking but the photoactive compounds will readily generate sufficient quantities of photobase upon exposure to electromagnetic radiation to bring about a desired reaction to produce a product at acceptable yield.

In some embodiments, a photoactive formulation is not chemically amplified, i.e., all acid generated is consumed in the reaction (e.g., all the tboc is deprotected and acid is consumed in the reaction). A tboc protected amino acid can be added along with a photoresist formulation to verify if chemical amplification occurs. In some embodiments, photosensitizers are optional when 248 nm is used.

In some embodiments, a photoactive formulation includes a water soluble photoacid generator and a water soluble photo sensitizer in a polymer matrix dispersed in water. In some embodiments, the polymer in the composition of the photoresist is generally inert and non-crosslinking but the photo reactive components will readily generate sufficient quantities of photoacid upon exposure in a deep ultra violet radiation tool to bring about a desired reaction to produce a product at acceptable yield.

In some embodiments, a photoactive formulation can include various components such as a water soluble photosensitizer, a water soluble photo active compound, a water soluble polymer, and a solvent. Specific examples of photoactive formulations are shown in Table 1.

Photosensitizers are generally added to a formulation to increase the sensitivity of the photoacid generator and bring the absorption spectrum of the formulation near deep UV (248 nm). In some embodiments, a water soluble photosensitizer can be a thioxanthenone. In some embodiments, a general thioxanthenone structure is shown below:

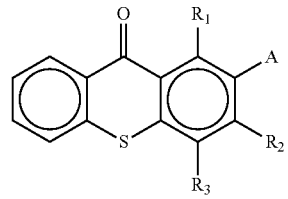

In some embodiments, the A, $R_1$, $R_2$, and $R_3$ groups of the thioxanthenone structure shown above can be:

1.
$R_1 = CH_3, R_2 = H, R_3 = CH_3, A = OCH_2\overset{OH}{\underset{|}{C}HCH_2N^+(CH_3)_3Cl^-}$ 2.
$R_1 = H, R_2 = CH_3, R_3 = CH_3, A = OCH_2\overset{OH}{\underset{|}{C}HCH_2N^+(CH_3)_3Cl^-}$ 3.
$R_1 = CH_3, R_2 = H, R_3 = CH_3, A = OCH_2CH_2CH_2N^+(C_2H_5)_3Br^-$ 4.
$R_1 = H, R_2 = CH_3, R_3 = CH_3, A = OCH_2CH_2CH_2N^+(C_2H_5)_3Br^-$ 5.
$R_1 = CH_3, R_2 = H, R_3 = CH_3, A = OCH_2CH_2CH_2SO_3Na$ 6.
$R_1 = H, R_2 = CH_3, R_3 = CH_3, A = OCH_2CH_2CH_2SO_3Na$ 7.
$R_1 = CH_3, R_2 = H, R_3 = CH_3, A = OCH_2\overset{OH}{\underset{|}{C}HCH_2SO_3Na}$ 8.
$R_1 = H, R_2 = CH_3, R_3 = CH_3, A = OCH_2\overset{OH}{\underset{|}{C}HCH_2SO_3Na}$ In some embodiments, a water soluble photosensitizer can be about 0.5-5% by weight of the total formulation concentration. In some embodiments, a water soluble photosensitizer can be about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

In some embodiments, a water soluble photoactive compound can be a photoacid generator (PAG) or a photobase generator (PBG). Photoacid generators (or PAGs) are cationic photoinitiators. A photoinitiator is a compound especially added to a formulation to convert absorbed light energy, UV or visible light, into chemical energy in the form of initiating species, e.g., free radicals or cations. Cationic photoinitiators are used extensively in optical lithography. The ability of some types of cationic photo initiators to serve as latent photochemical sources of very strong protonic or Lewis acids is generally the basis for their use in photo imaging applications. In some embodiments, a photoacid generator is a water soluble iodonium salt, a water soluble polonium salt, or a water soluble sulfonium salt. In some embodiments, a photoacid generator is (4-Methoxyphenyl) phenyliodonium or trifluoromethanesulfonate. In some embodiments, a photoacid generator is (2,4-dihydroxyphenyl)dimethylsulfonium triflate or (4 methoxyphenyl)dimethylsulfonium triflate, shown below:

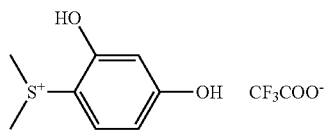

In some embodiments, a photoacid generator is iodonium and sulfonium salts of triflates, phosphates and/or antimonates, 1,3-Bis[(2-nitrobenzyl)oxycarbonyl-4-piperidyl] propane, or 1,3-Bis[(1-(9-fluorenylmethoxycarbonyl)-4-piperidyl]propane. In some embodiments, a photoacid generator is about 0.5-5% by weight of the total formulation concentration. In some embodiments, a photoacid generator is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

In some embodiments, a water soluble polymer is a water soluble non-crosslinking inert polymer. In some embodiments, a water soluble polymer is a polyvinyl pyrrolidone. The general structure of polyvinyl pyrrolidone is as follows, where n is any positive integer greater than 1:

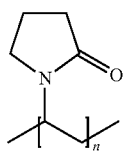

In some embodiments, a water soluble polymer is a polymer of vinyl pyrrolidone. In some embodiments, a water soluble polymer is polyvinyl pyrrolidone. Poly vinyl pyrrolidone is soluble in water and other polar solvents. When dry it is a light flaky powder, which generally readily absorbs up to 40% of its weight in atmospheric water. In solution, it has excellent wetting properties and readily forms films.

In some embodiments, a water soluble polymer is about 0.5-5% by weight of the total formulation concentration. In some embodiments, a water soluble polymer is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

In some embodiments, a solvent is water, ethyl lactate, or a combination thereof. In some embodiments, ethyl lactate can be dissolved in water to more than 50% to form a solvent. In some embodiments, a solvent can be about 10% propylene glycol methyl ether acetate (PGMEA) and about 90% DI water. In some embodiments, a solvent can include up to about 20% PGMEA.

In some embodiments, the solvent is about 80-90% by weight of the total formulation concentration. In some embodiments, the solvent is about less than 70, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or greater than 99% by weight of the total formulation concentration.

The photoactive coupling formulation comprises coupling molecules. The coupling molecules can include amino acids. In some instances all peptides on an array described herein are composed of naturally occurring amino acids. In others, peptides on an array described herein can be composed of a combination of naturally occurring amino acids and non-naturally occurring amino acids. In other cases, peptides on an array can be composed solely from non-naturally occurring amino acids. Non-naturally occurring amino acids include peptidomimetics as well as D-amino acids. The R group can be found on a natural amino acid or a group that is similar in size to a natural amino acid R group. Additionally, unnatural amino acids, such as beta-alanine, phenylglycine, homoarginine, aminobutyric acid, aminohexanoic acid, aminoisobutyric acid, butylglycine, citrulline, cyclohexylalanine, diaminopropionic acid, hydroxyproline, norleucine, norvaline, ornithine, penicillamine, pyroglutamic acid, sarcosine, and thienylalanine can also be incorporated. These and other natural and unnatural amino acids are available from, for example, EMD Biosciences, Inc., San Diego, Calif. In some embodiments, a coupling molecule comprises a naturally occurring or artificial amino acid or polypeptide. Examples of coupling molecules include Boc-Glycine-OH and Boc-Histidine-OH. In some embodiments, the artificial amino acid is a D-amino acid. In some embodiments, a coupling molecule is 1-2% by weight of the total formulation concentration. In some embodiments, a coupling molecule is about 0.5-5% by weight of the total formulation concentration. In some embodiments, a coupling molecule is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration. In some embodiments, a coupling molecule comprises a protected group, e.g., a group protected via t-Boc or F-Moc chemistry. In most instances, increasing the concentration of a coupling molecule provides the best performance.

In some embodiments, a formulation can contain a t-Boc group that helps in chemical amplification of the initial acid generated upon post exposure baking. Thus, the formulation can include a tboc protected amino acid, e.g., in order to enhance the chemical amplification during post-exposure bake. In some embodiments, this t-Boc protected amino acid would make up about 0.5-1% by weight of the formulation. In some embodiments, a protected amino acid is about 0.5-5% by weight of the total formulation concentration. In some embodiments, a protected amino acid is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

In some embodiments, a coupling reagent is carbodiimide or triazole. In some embodiments, a coupling reagent is N-Hydroxysuccinimide (NHS). In some embodiments, a coupling reagent is 2-4% by weight of the total formulation concentration. In some embodiments, a coupling reagent is about 0.5-5% by weight of the total formulation concentration. In some embodiments, a coupling reagent is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

In any of the combinations above, the formulation can be completely water strippable even after photo exposure and bake. Thus, in some embodiments, only water is used to wash away the photoactive formulation after exposure and post bake.

Carboxylic Acid Activating Formulations

Disclosed herein are activating formulations for activating carboxylic acid so that it reacts with a free amino group of a biomolecule, e.g., an amino acid, peptide, or polypeptide. An activating formulation can include components such as a carboxylic acid group activating compound and a solvent. In some embodiments, the carboxylic acid group activating compound is a carbodiimide or a carbodiimide precursor. In some embodiments, the carbodiimide is 1-ethyl-3-(3-dimethylaminopropyl) carbodiimide. In some embodiments, the carboxylic acid group activating compound is N-Hydroxysuccinimide [NHS]. In some embodiments, the carboxylic acid group activating compound is selected from: 1-Ethyl-3-(3-dimethylaminopropyl)carbodiimide [EDC], N-hydroxysuccinimide [NHS], 1,3-Diisopropylcarbodiimide [DIC], hydroxybenzotriazole [HOBt], 1-Hydroxy-7-azabenzotriazole [HOAt], (O-(7-azabenzotriazol-1-yl)-N,N,N',N'-tetramethyluronium hexafluorophosphate) [HATU], benzotriazol-1-yl-oxytripyrrolidinophosphonium hexafluorophosphate [PyBOP], and N,N-Diisopropylethylamine [DIEA]. In some embodiments, the solvent is water. In some embodiments, the solvent is N-methylpyrrolidone [NMP]. In some embodiments, the carboxylic acid group activating compound converts the carboxylic acid to a carbonyl group (i.e., carboxylic acid group activation). In some embodiments, the carboxylic acid group is activated for 5, 10, 15, 20, 30, 45, or 60 minutes after exposure to an activation formulation.

In some embodiments, the activating formulation comprises 4% by weight of 1-ethyl-3-(3-dimethylaminopropyl) carbodiimide and 2% by weight of N-hydroxysuccinimide [NHS]. dissolved in deionized water. In some embodiments, the activating formulation comprises 4% by weight of 1,3-Diisopropylcarbodiimide [DIC] and 2% by weight of hydroxybenzotriazole [HOBt] dissolved in NMP. In some embodiments, the activating formulation comprises 4% by weight of (O-(7-azabenzotriazol-1-yl)-N,N,N',N'-tetramethyluronium hexafluorophosphate) (HATU) and 2% by weight of N,N-Diisopropylethylamine [DIEA] dissolved in NMP. In some embodiments, the activating formulation comprises 4% by weight of Benzotriazol-1-yl-oxytripyrrolidinophosphonium hexafluorophosphate [PyBOP] and 2% by weight of DIEA dissolved in NMP.

In some embodiments, the carboxylic acid group activating compound is a carbodiimide precursor. In one aspect, the carbodiimide precursor is converted to a carbodiimide through exposure to radiation, e.g., ultraviolet radiation. In one embodiment, the carbodiimide precursor is a thione. The carbodiimide precursor can also be referred to as a photoactivated carbodiimide. In one embodiment, photoactivated carbodiimides are used to provide site-specific activation of carboxylic acid groups on an array by spatially controlling exposure of the photoactivated carbodiimide solution to electromagnetic radiation at a preferred activation wavelength. In some embodiments, the preferred activation wavelength is 248 nm.

In some embodiments, the carbodiimide precursor is a thione that is converted to carbodiimide via photoactivation. In one aspect, the thione is converted to a hydroxymethyl phenyl carbodiimide after exposure to electromagnetic radiation. In some embodiments, the thione is 4,5-dihydro-4-(hydroxymethyl)-1-phenyl-1H-tetrazole-5-thione, 1-(3-(dimethylamino)propyl)-4-ethyl-1,4-dihydro-5H-tetrazole-5-thione, 1,4-Bis(2,2-dimethyl-1,3-dioxolan-4-ylmethyl)-1,4-dihydro-5H-tetrazole-5-thione, 4-cyclohexyl-1H-tetrazole-5(4H)-thione, or 1-phenyl-4-(piperidinomethyl)tetrazole-5(4H)-thione, and the like.

In some embodiments, the activating solution comprises a carbodiimide precursor, a solvent, and a polymer. In one embodiment, the carbodiimide precursor is 4,5-dihydro-4-(hydroxymethyl)-1-phenyl-1H-tetrazole-5-thione, 1-(3-(dimethylamino)propyl)-4-ethyl-1,4-dihydro-5H-tetrazole-5-thione, or 1,4-Bis(2,2-dimethyl-1,3-dioxolan-4-ylmethyl)-1,4-dihydro-5H-tetrazole-5-thione. In some embodiments, the carbodiimide precursor is present in the activation solution at a concentration of 2.5% by weight. In some embodiments the carbodiimide precursor is present in the activation solution at a concentration of 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or 5.0% by weight of the total formulation concentration.

In some embodiments, the solvent is water. In some embodiments, the solvent is about 80-90% by weight of the total formulation concentration. In some embodiments, the solvent is about less than 70, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or greater than 99% by weight of the total formulation concentration.

In some embodiments, a polymer is a polyvinyl pyrrolidone and/or a polyvinyl alcohol. In some embodiments, a polymer is about 0.5-5% by weight of the total formulation concentration. In some embodiments, a polymer is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

In some embodiments, a coupling reagent is a carbodiimide. In some embodiments, a coupling reagent is a triazole. In some embodiments, a coupling reagent is 1-ethyl-3-(3-dimethylaminopropyl) carbodiimide. In some embodiments, a coupling reagent is about 0.5-5% by weight of the total formulation concentration. In some embodiments, a coupling reagent is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

Linker Formulations

Also disclosed herein is a linker formulation. A linker formulation can include components such as a solvent, a water soluble polymer, a water soluble linker molecule, and a water soluble coupling reagent. In some embodiments, the polymer is 1% by weight polyvinyl alcohol and 2.5% by weight poly vinyl pyrrollidone, the linker molecule is 1.25% by weight polyethylene oxide, the coupling reagent is 1% by weight 1-ethyl-3-(3-dimethylaminopropyl) carbodiimide, and the solvent includes water. In some embodiments, the polymer is 0.5-5% by weight polyvinyl alcohol and 0.5-5% by weight poly vinyl pyrrollidone, the linker molecule is 0.5-5% by weight polyethylene oxide, the coupling reagent is 0.5-5% by weight 1-ethyl-3-(3-dimethylaminopropyl) carbodiimide, and the solvent includes water.

In some embodiments, the solvent is water, an organic solvent, or a combination thereof. In some embodiments, the organic solvent is N-methyl pyrrolidone, dimethyl formamide, dichloromethane, dimethyl sulfoxide, or a combination thereof. In some embodiments, the solvent is about 80-90% by weight of the total formulation concentration. In some embodiments, the solvent is about less than 70, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or greater than 99% by weight of the total formulation concentration.

In some embodiments, a water soluble polymer is a polyvinyl pyrrolidone and/or a polyvinyl alcohol. The general structure of polyvinyl alcohol is as follows, where n is any positive integer greater than 1:

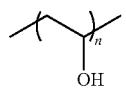

In some embodiments, a water soluble polymer is about 0.5-5% by weight of the total formulation concentration. In some embodiments, a water soluble polymer is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

In some embodiments, a coupling reagent is a water soluble carbodimide. In some embodiments, a coupling reagent is a water soluble triazole. In some embodiments, a coupling reagent is 1-ethyl-3-(3-dimethylaminopropyl) carbodiimide. In some embodiments, a coupling reagent is about 0.5-5% by weight of the total formulation concentration. In some embodiments, a coupling reagent is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

A linker molecule can be a molecule inserted between a surface disclosed herein and peptide that is being synthesized via a coupling molecule. A linker molecule does not necessarily convey functionality to the resulting peptide, such as molecular recognition functionality, but can instead elongate the distance between the surface and the peptide to enhance the exposure of the peptide's functionality region(s) on the surface. In some embodiments, a linker can be about 4 to about 40 atoms long to provide exposure. The linker molecules can be, for example, aryl acetylene, ethylene glycol oligomers containing 2-10 monomer units, i.e. polyethylene glycols [PEGs], diamines, diacids, amino acids, and combinations thereof. Examples of diamines include ethylene diamine and diamino propane. Alternatively, linkers can be the same molecule type as that being synthesized (e.g., nascent polymers or various coupling molecules), such as polypeptides and polymers of amino acid derivatives such as for example, amino hexanoic acids. In some embodiments, a linker molecule is a molecule having a carboxylic group at a first end of the molecule and a protecting group at a second end of the molecule. In some embodiments, the protecting group is a t-Boc protecting group or an F-Moc protecting group. In some embodiments, a linker molecule is or includes an aryl acetylene, a polyethyleneglycol, a nascent polypeptide, a diamine, a diacid, a peptide, or combinations thereof. In some embodiments, a linker molecule is about 0.5-5% by weight of the total formulation concentration. In some embodiments, a linker molecule is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

The unbound portion of a linker molecule, or free end of the linker molecule, can have a reactive functional group which is blocked, protected, or otherwise made unavailable for reaction by a removable protective group, e.g., t-Boc or F-Moc as noted above. The protecting group can be bound to a monomer, a polymer, or a linker molecule to protect a reactive functionality on the monomer, polymer, or linker molecule. Protective groups that can be used include all acid and base labile protecting groups. For example, peptide amine groups can be protected by t-butoxycarbonyl [t-BOC or BOC] or benzyloxycarbonyl [CBZ], both of which are acid labile, or by 9-fluorenylmethoxycarbonyl [FMOC], which is base labile.

Additional protecting groups that can be used include acid labile groups for protecting amino moieties: tert-amyloxycarbonyl, adamantyloxycarbonyl, 1-methylcyclobutyloxycarbonyl, 2-(p-biphenyl)propyl(2)oxycarbonyl, 2-(p-phenylazophenylyl)propyl(2)oxycarbonyl, alpha,alpha-dimethyl-3,5-dimethyloxybenzyloxy-carbonyl, 2-phenylpropyl(2)oxycarbonyl, 4-methyloxybenzyloxycarbonyl, furfuryloxycarbonyl, triphenylmethyl (trityl), p-toluenesulfenylaminocarbonyl, dimethylphosphinothioyl, diphenylphosphinothioyl, 2-benzoyl-1-methylvinyl, o-nitrophenylsulfenyl, and 1-naphthylidene; as base labile groups for protecting amino moieties: 9 fluorenylmethyloxycarbonyl, methylsulfonylethyloxycarbonyl, and 5-benzisoazolylmethyleneoxycarbonyl; as groups for protecting amino moieties that are labile when reduced: dithiasuccinoyl, p-toluene sulfonyl, and piperidino-oxycarbonyl; as groups for protecting amino moieties that are labile when oxidized: (ethylthio) carbonyl; as groups for protecting amino moieties that are labile to miscellaneous reagents, the appropriate agent is listed in parenthesis after the group: phthaloyl (hydrazine), trifluoroacetyl (piperidine), and chloroacetyl (2-aminothiophenol); acid labile groups for protecting carboxylic acids: tert-butyl ester; acid labile groups for protecting hydroxyl groups: dimethyltrityl. (See also, Greene, T. W., Protective Groups in Organic Synthesis, Wiley-Interscience, NY, (1981)).

Coupling Formulations

Also disclosed are coupling formulations. In some embodiments, a coupling formulation can include components such as a solvent, a water soluble polymer, a water soluble coupling molecule, a water soluble neutralization reagent, and a water soluble coupling reagent.

In some embodiments, a solvent is water, an organic solvent, or combination thereof. In some embodiments, the organic solvent is N-methyl pyrrolidone, dimethyl formamide or combinations thereof.

In some embodiments, a polymer is a water soluble vinyl pyrrolidone or a water soluble vinyl alcohol. In some embodiments, a polymer is 2.5-5% by weight of the total formulation concentration. In some embodiments, a polymer is about 0.5-5% by weight of the total formulation concentration. In some embodiments, a polymer is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

In some embodiments, a neutralization reagent can include Hunig's base. The structure of Hunig's base is:

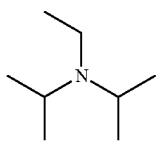

In some embodiments, a neutralization reagent is 1-2% by weight of the total formulation concentration. In some embodiments, a neutralization reagent is about 0.5-5% by weight of the total formulation concentration. In some embodiments, a neutralization reagent is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

The coupling molecules can include amino acids. In some embodiments, all peptides on an array described herein are composed of naturally occurring amino acids. In others, peptides on an array described herein can be composed of a combination of naturally occurring amino acids and non-naturally occurring amino acids. In other cases, peptides on an array can be composed solely from non-naturally occurring amino acids. Non-naturally occurring amino acids include peptidomimetics as well as D-amino acids. The R group can be found on a natural amino acid or a group that is similar in size to a natural amino acid R group. Additionally, unnatural amino acids, such as beta-alanine, phenylglycine, homoarginine, aminobutyric acid, aminohexanoic acid, aminoisobutyric acid, butylglycine, citrulline, cyclohexylalanine, diaminopropionic acid, hydroxyproline, norleucine, norvaline, ornithine, penicillamine, pyroglutamic acid, sarcosine, and thienylalanine can also be incorporated. These and other natural and unnatural amino acids are available from, for example, EMD Biosciences, Inc., San Diego, Calif. In some embodiments, a coupling molecule comprises a naturally occurring or artificial amino acid or polypeptide. Examples of coupling molecules include Boc-Glycine-OH and Boc-Histine-OH. In some embodiments, the artificial amino acid is a D-amino acid. In some embodiments, a coupling molecule is 1-2% by weight of the total formulation concentration. In some embodiments, a coupling molecule is about 0.5-5% by weight of the total formulation concentration. In some embodiments, a coupling molecule is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration. In some embodiments, a coupling molecule comprises a protected side group, e.g., a side group protected via t-Boc or F-Moc chemistry. In most instances, increasing the concentration of a coupling molecule provides the best performance.

In some embodiments, a coupling reagent is water soluble carbodimide or water soluble triazole. In some embodiments, a coupling reagent is 2-4% by weight of the total formulation concentration. In some embodiments, a coupling reagent is about 0.5-5% by weight of the total formulation concentration. In some embodiments, a coupling reagent is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

In any of the combinations above, the formulation can be completely water strippable.

Substrates

Also disclosed herein are substrates. In some embodiments a substrate surface is planar (i.e., 2-dimensional). In some embodiments a substrate surface is functionalized with free carboxylic acid groups. In some embodiments, a substrate surface is functionalized with free amine groups. A surface that is functionalized with free amine groups can be converted to free carboxylic acid groups by reacting with activating the carboxylic acid groups of a molecule comprising at least two free carboxylic acid groups (e.g., converting the carboxylic acid group to a carbonyl group using carbodiimide) and reacting the molecule with the free amine groups attached to the surface of the substrate. In some embodiments, the molecule comprising multiple carboxylic acid groups is succinic anhydride, polyethylene glycol diacid, benzene-1,3,5-tricarboxylic acid, benzenehexacarboxylic acid, or carboxymethyl dextran.

In some embodiments, a substrate can include a porous layer (i.e., a 3-dimensional layer) comprising functional groups for binding a first monomer building block. In some embodiments, a substrate surface comprises pillars for peptide attachment or synthesis. In some embodiments, a porous layer is added to the top of the pillars.

Pillar Substrates

Figure 3A:
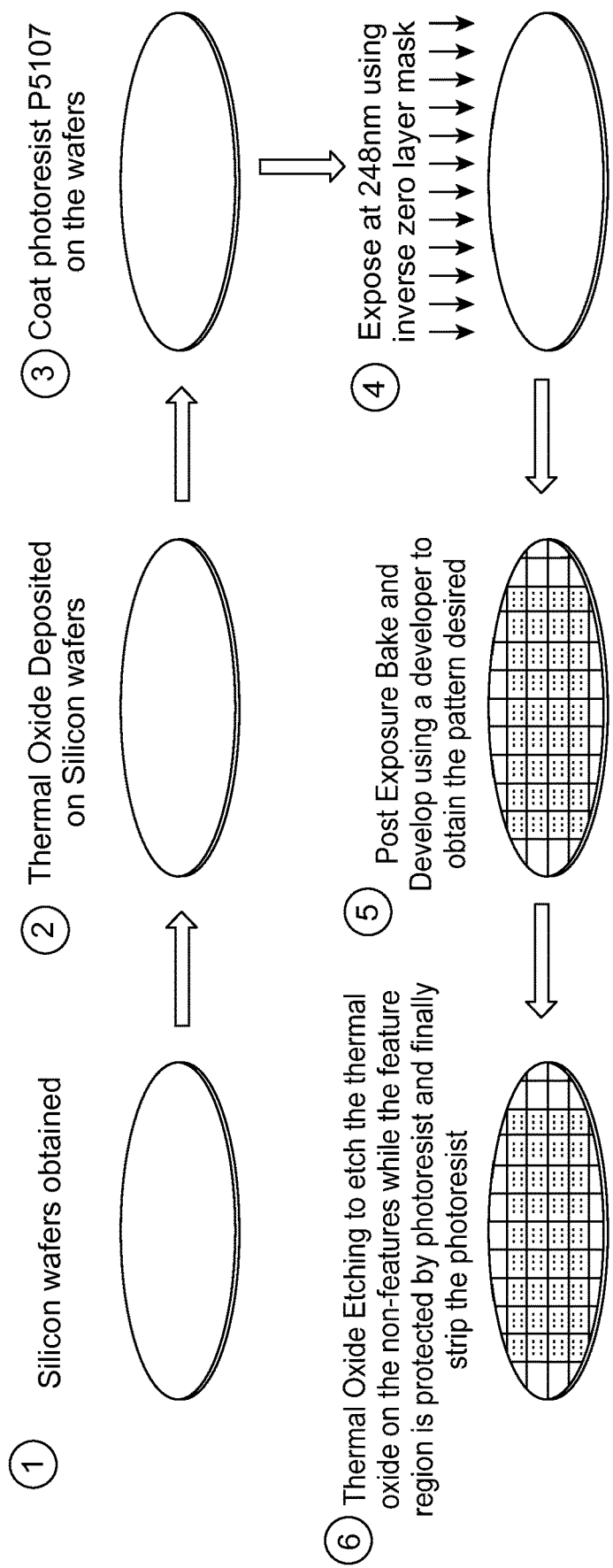
FIG. 3 shows (A) wafer substrate preparation, (B) pillar substrate, and (C) AFM-measured roughness and calculated density of substrate, according to an embodiment.
Figure 3B:
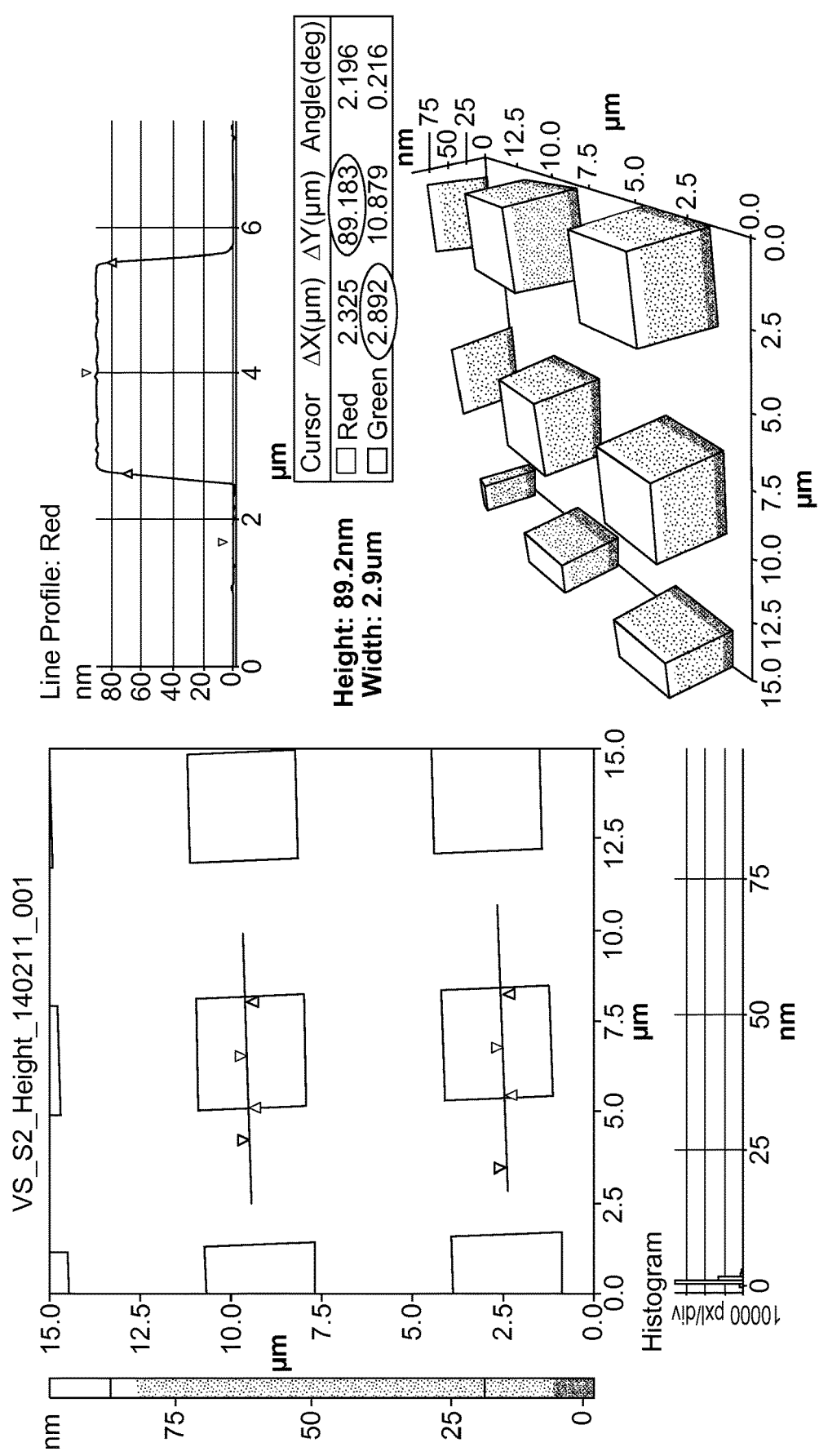
Figure 3C:
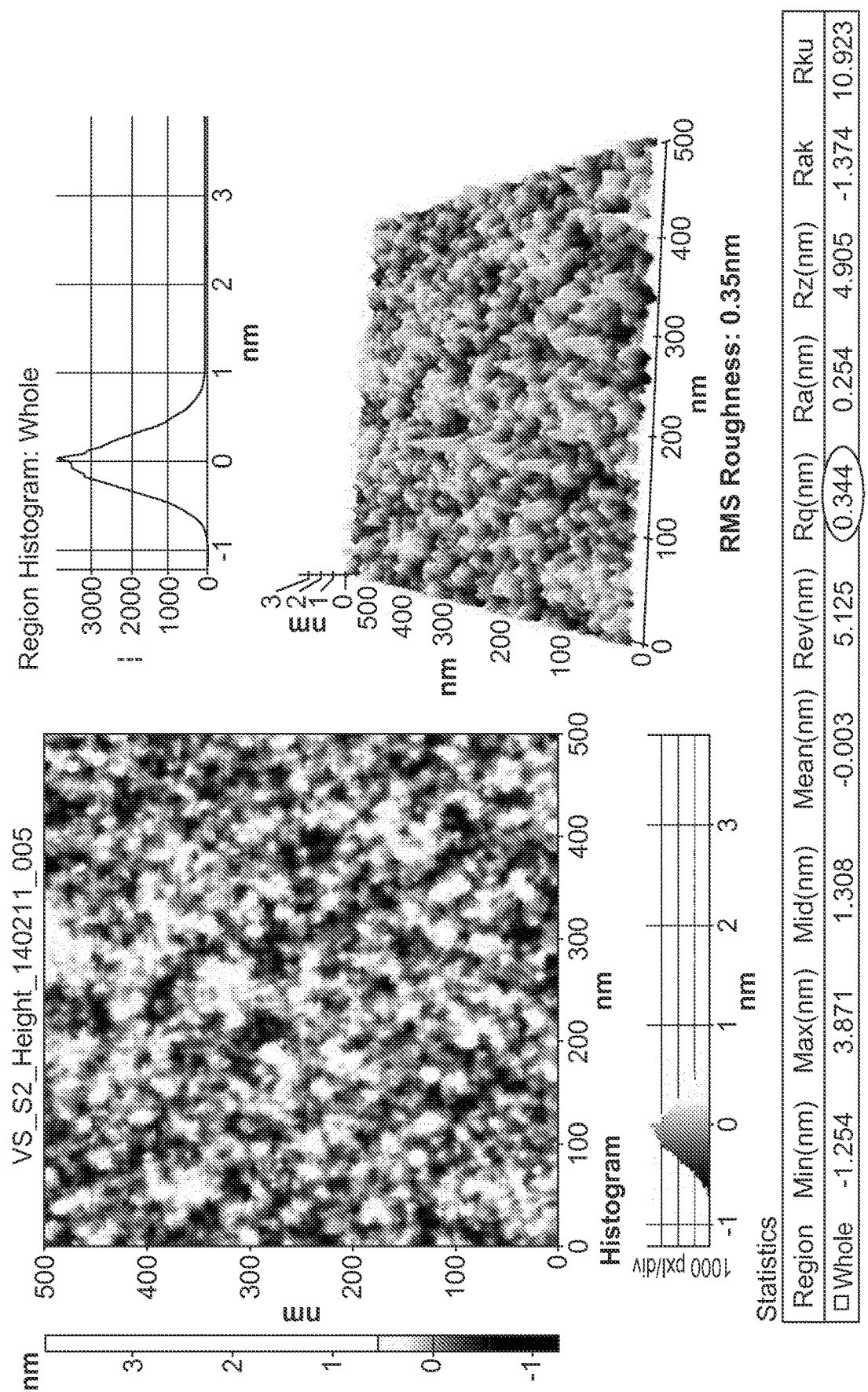

In some embodiments, a substrate can include a planar layer having an upper surface and a lower surface; and a plurality of pillars operatively coupled to the layer in positionally-defined locations, wherein each pillar has a planar surface extended from the layer, wherein the distance between the surface of each pillar and the upper surface of the layer is between about 1,000-5,000 angstroms, and wherein the plurality of pillars are present at a density of greater than about 10,000/cm². An example of a substrate is shown in FIGS. 3B and 3C.

In some embodiments, the distance between the surface of each pillar and the upper surface of the later can be between about less than 1,000, 2,000, 3,000, 3,500, 4,500, 5,000, or greater than 5,000 angstroms (or any integer in between).

In some embodiments, the surface of each pillar is parallel to the upper surface of the layer. In some embodiments, the surface of each pillar is substantially parallel to the upper surface of the layer.

In some embodiments, the plurality of pillars are present at a density of greater than 500, 1,000, 2,000, 3,000, 4,000, 5,000, 6,000, 7,000, 8,000, 9,000, 10,000, 11,000, or 12,000/cm² (or any integer in between). In some embodiments, the plurality of pillars are present at a density of greater than 10,000/cm². In some embodiments, the plurality of pillars are present at a density of about 10,000/cm$^2$ to about 2.5 million/cm$^2$ (or any integer in between). In some embodiments, the plurality of pillars are present at a density of greater than 2.5 million/cm$^2$.

In some embodiments, the surface area of each pillar surface is at least 1 µm$^2$. In some embodiments, the surface area of each pillar surface can be at least 0.1, 0.5, 12, 3, 4, 5, 6, 7, 8, 9, 10, 15, 20, 25, 30, 35, 40, 45, or 50 µm$^2$ (or any integer in between). In some embodiments, the surface area of each pillar surface has a total area of less than 10,000 µm$^2$. In some embodiments, the surface area of each pillar surface has a total area of less than 500, 1,000, 2,000, 3,000, 4,000, 5,000, 6,000, 7,000, 8,000, 9,000, 10,000, 11,000, or 12,000 µm$^2$ (or any integer in between).

In some embodiments, the distance between the surface of each pillar and the lower surface of the layer is 2,000-7,000 angstroms. In some embodiments, the distance between the surface of each pillar and the lower surface of the layer is about less than 500, 1,000, 2,000, 3,000, 4,000, 5,000, 6,000, 7,000, 8,000, 9,000, 10,000, 11,000, 12,000, or greater than 12,000 angstroms (or any integer in between). In some embodiments, the distance between the surface of each pillar and the lower surface of the layer is 7,000, 3,000, 4,000, 5,000, 6,000, or 7,000 angstroms (or any integer in between).

In some embodiments, the layer is 1,000-2,000 angstroms thick. In some embodiments, the layer is about less than 500, 1,000, 2,000, 3,000, 4,000, 5,000, 6,000, 7,000, 8,000, 9,000, 10,000, 11,000, 12,000, or greater than 12,000 angstroms thick (or any integer in between).

In some embodiments, the center of each pillar is at least 2,000 angstroms from the center of any other pillar. In some embodiments, the center of each pillar is at least about 500, 1,000, 2,000, 3,000, or 4,000 angstroms (or any integer in between) from the center of any other pillar. In some embodiments, the center of each pillar is at least about 2 µm to 200 µm from the center of any other pillar.

In some embodiments, the planar layer comprises metal. In some embodiments, the metal is chromium. In some embodiments, the metal is chromium, titanium, aluminum, tungsten, gold, silver, tin, lead, thallium, indium, or a combination thereof. In some embodiments, the layer is at least 98.5-99% metal. In some embodiments, the layer is 100% metal. In some embodiments, the layer is at least about greater than 90, 91, 92, 93, 94, 95, 96, 97, 98, 98.5, or 99% metal. In some embodiments, the layer is a homogenous layer of metal.

In some embodiments, the planar layer comprises silicon, silicon dioxide, silicon nitride or the like. In some embodiments, at least one or each pillar comprises silicon. In some embodiments, at least one or each pillar comprises silicon dioxide or silicon nitride. In some embodiments, at least one or each pillar is at least 90, 91, 92, 93, 94, 95, 96, 97, 98, 98.5, or 99% silicon dioxide.

In some embodiments, a substrate can include a linker molecule having a free amino terminus attached to the surface of each pillar. In some embodiments, a substrate can include a linker molecule having a free amino terminus attached to the surface of at least one pillar. In some embodiments, a substrate can include a linker molecule having a protecting group attached to the surface of each pillar. In some embodiments, a substrate can include a linker molecule having a protecting group attached to the surface of at least one pillar. In some embodiments, a substrate can include a coupling molecule attached to the surface of at least one pillar. In some embodiments, a substrate can include a coupling molecule attached to the surface of each pillar. In some embodiments, a substrate can include a water soluble polymer in contact with the surface of at least one of said pillars. In some embodiments, a substrate can include a water soluble polymer in contact with the surface of each pillar. In some embodiments, a substrate can include a gelatinous form of a water soluble polymer in contact with the surface of at least one of said pillars. In some embodiments, a substrate can include a solid form of a water soluble polymer in contact with the surface of at least one of said pillars.

In some embodiments, the surface of at least one of said pillars of the substrate is derivatized. In some embodiments, a substrate can include a polymer chain attached to the surface of at least one of said pillars. In some embodiments, the polymer chain comprises a peptide chain. In some embodiments, the attachment to the surface of said at least one pillar is via a covalent bond.

In some embodiments, the surface of each pillar is square or rectangular in shape. In some embodiments, the substrate can be coupled to a silicon dioxide layer. The silicon dioxide layer can be about 0.5 µm to 3 µm thick. In some embodiments, the substrate can be coupled to a wafer, e.g., a silicon wafer. The silicon dioxide layer can be about 700 µm to 750 µm thick.

In some embodiments, a substrate can include a porous layer comprising functional groups for binding a first monomer building block.

Porous Layer Substrates

Porous layers which can be used are permeable, polymeric materials of porous structure which can have a functional group (which is native to the constituent polymer or which is introduced to the porous layer) for attachment of the first peptide building block. The functional group can comprise a free carboxylic acid group or a free amino group. For example, a porous layer can be comprised of porous silicon with functional groups for attachment of a polymer building block attached to the surface of the porous silicon. In another example, a porous layer may comprise a crosslinked polymeric material. In some embodiments, the porous layer may employ polystyrenes, saccharose, dextrans, polyacryloylmorpholine, polyacrylates, polymethylacrylates, polyacrylamides, polyacrylolpyrrolidone, polyvinylacetates, polyethyleneglycol, agaroses, sepharose, other conventional chromatography type materials and derivatives and mixtures thereof. In some embodiments, the porous layer building material is selected from: poly(vinyl alcohol), dextran, sodium alginate, poly(aspartic acid), poly(ethylene glycol), poly(ethylene oxide), poly(vinyl pyrrolidone), poly(acrylic acid), poly(acrylic acid)-sodium salt, poly(acrylamide), poly(N-isopropyl acrylamide), poly(hydroxyethyl acrylate), poly(acrylic acid), poly(sodium styrene sulfonate), poly(2-acrylamido-2-methyl-1-propanesulfonic acid), polysaccharides, and cellulose derivatives. Preferably the porous layer has a porosity of 10-80%. In one embodiment, the thickness of the porous layer ranges from 0.01 µm to about 1,000 µm. Pore sizes included in the porous layer may range from 2 nm to about 100 µm.

According to another aspect of the present invention there is provided a substrate comprising a porous polymeric material having a porosity from 10-80%, wherein reactive groups are chemically bound to the pore surfaces and are adapted in use to interact, e.g. by binding chemically, with a reactive species, e.g., deprotected monomeric building blocks or polymeric chains. In one embodiment the reactive group is a carboxylic acid group. The carboxylic acid group is free to bind, for example, an unprotected amine group of a peptide or polypeptide. In another embodiment, the reactive group is an amino group that is free to bind to, for example, an unprotected carboxylic acid group of a peptide or polypeptide.

In an embodiment, the porous layer is in contact with a support layer. The support layer comprises, for example, metal, plastic, silicon, silicon oxide, or silicon nitride. In another embodiment, the porous layer may be in contact with a patterned surface, such as on top of pillar substrates described above.

Arrays

Also disclosed herein are arrays. In some embodiments, an array can be a two-dimensional array. In some embodiments, a two-dimensional array can include features attached to a surface at positionally-defined locations, said features each comprising: a collection of peptide chains of determinable sequence and intended length, wherein within an individual feature, the fraction of peptide chains within said collection having the intended length is characterized by an average coupling efficiency for each coupling step of about 98%.

In some embodiments, the surface of the array is functionalized with free carboxylic acids. In some embodiments, the free carboxylic acids are activated to bind to amine groups, e.g., during polypeptide synthesis on the surface of the array. In some embodiments, the surface density of free carboxylic acid groups on the array is greater than $10/cm^2$, $100/cm^2$, $1,000/cm^2$, $10,000/cm^2$, $1,00,000/cm^2$, $1,000,000/cm^2$, or $10,000,000/cm^2$.

In some embodiments, an array can be a three-dimensional array, e.g., a porous array comprising features attached to the surface of the porous array. In some embodiments, the surface of a porous array includes external surfaces and surfaces defining pore volume within the porous array. In some embodiments, a three-dimensional array can include features attached to a surface at positionally-defined locations, said features each comprising: a collection of peptide chains of determinable sequence and intended length. In one embodiment, within an individual feature, the fraction of peptide chains within said collection having the intended length is characterized by an average coupling efficiency for each coupling step of greater than 98%.

In some embodiments, the average coupling efficiency for each coupling step is at least 98.5%. In some embodiments, the average coupling efficiency for each coupling step is at least 99%. In some embodiments, the average coupling efficiency for each coupling step is at least 90, 91, 92, 93, 94, 95, 96, 97, 98, 98.5, 98.6, 98.7, 98.8, 98.9, 99.0, 99.1, 99.2, 99.3, 99.4, 99.5, 99.6, 99.7, 99.8, 99.9, or 100%. In some embodiments, the coupling efficiency is substantially constant over each coupling cycle, and exceeds 98%. In some embodiments, the average coupling efficiency exceeds 98% for each coupling step used to synthesize a 4-mer, or a 5-mer, or a 6-mer, or a 7-mer or longer polypeptide. In some embodiments, the coupling efficiency is substantially constant and exceeds 98% for each coupling step used to synthesize a 4-mer, or a 5-mer, or a 6-mer, or a 7-mer or longer polypeptide.

In some embodiments, a surface includes a substrate disclosed herein. In some embodiments, a surface is a material or group of materials having rigidity or semi-rigidity. In some embodiments, a surface can be substantially flat, although in some embodiments it can be desirable to physically separate synthesis regions for different molecules or features with, for example, wells, raised regions, pins, pillars, etched trenches, or the like. In certain embodiments, a surface may be porous. Surface materials can include, for example, silicon, bio-compatible polymers such as, for example poly(methyl methacrylate) [PMMA] and polydimethylsiloxane [PDMS], glass, $SiO_2$ (such as, for example, a thermal oxide silicon wafer such as that used by the semiconductor industry), quartz, silicon nitride, functionalized glass, gold, platinum, and aluminum. Functionalized surfaces include for example, amino-functionalized glass, carboxy functionalized glass, and hydroxy functionalized glass. Additionally, a surface may optionally be coated with one or more layers to provide a second surface for molecular attachment or functionalization, increased or decreased reactivity, binding detection, or other specialized application. Surface materials and or layer(s) can be porous or non-porous. For example, a surface can be comprised of porous silicon. Additionally, the surface can be a silicon wafer or chip such as those used in the semiconductor device fabrication industry. In the case of a wafer or chip, a plurality of arrays can be synthesized on the wafer.

In some embodiments, each peptide chain is from 5 to 60 amino acids in length. In some embodiments, each peptide chain is at least 5 amino acids in length. In some embodiments, each peptide chain is at least 5, 10, 15, 20, 25, 30, 35, 40, 45, 50, 55, or 60 amino acids in length. In some embodiments, each peptide chain is less than 5, at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or greater than 60 amino acids in length. In some embodiments, each peptide chain comprises one or more L amino acids. In some embodiments, each peptide chain comprises one or more D amino acids. In some embodiments, each peptide chain comprises one or more naturally occurring amino acids. In some embodiments, each peptide chain comprises one or more synthetic amino acids.

In some embodiments, an array can include at least 1,000 different peptide chains attached to the surface. In some embodiments, an array can include at least 10,000 different peptide chains attached to the surface. In some embodiments, an array can include at least 100, 500, 1000, 2000, 3000, 4000, 5000, 6000, 7000, 8000, 9000, 10,000, or greater than 10,000 different peptide chains attached to the surface (or any integer in between).

In some embodiments, an array can include at least peptide density of at least 1,000 peptide chains attached to the surface per $cm^2$. In some embodiments, an array can include at least 10,000 peptide chains/$cm^2$. In some embodiments, an array can include at least 100, 500, 1000, 2000, 3000, 4000, 5000, 6000, 7000, 8000, 9000, 10,000, or greater than 10,000 peptide chains/$cm^2$ (or any integer in between).

In some embodiments, each of the positionally-defined locations is at a different, known location that is physically separated from each of the other positionally-defined locations. In some embodiments, each of the positionally-defined locations is a positionally-distinguishable location. In some embodiments, each determinable sequence is a known sequence. In some embodiments, each determinable sequence is a distinct sequence.

In some embodiments, the features are covalently attached to the surface. In some embodiments, said peptide chains are attached to the surface through a linker molecule or a coupling molecule.

In some embodiments, the features comprise a plurality of distinct, nested, overlapping peptide chains comprising subsequences derived from a source protein having a known sequence. In some embodiments, each peptide chain in the plurality is substantially the same length. In some embodiments, each peptide chain in the plurality is the same length. In some embodiments, each peptide chain in the plurality is at least 5 amino acids in length. In some embodiments, each peptide chain in the plurality is at least 5, 10, 15, 20, 25, 30, 35, 40, 45, 50, 55, or 60 amino acids in length. In some embodiments, each peptide chain in the plurality is less than 5, at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or greater than 60 amino acids in length. In some embodiments, at least one peptide chain in the plurality is at least 5 amino acids in length. In some embodiments, at least one peptide chain in the plurality is at least 5, 10, 15, 20, 25, 30, 35, 40, 45, 50, 55, or 60 amino acids in length. In some embodiments, at least one peptide chain in the plurality is less than 5, at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or greater than 60 amino acids in length. In some embodiments, each polypeptide in a feature is substantially the same length. In some embodiments, each polypeptide in a feature is the same length. In some embodiments, the features comprise a plurality of peptide chains each having a random, determinable sequence of amino acids.

Methods of Manufacturing Arrays

Also disclosed herein are methods for manufacturing arrays. In some embodiments, the arrays disclosed herein can be synthesized in situ on a surface, e.g., a substrate disclosed herein. In some instances, the arrays are made using photolithography. For example, masks can be used to control radiation or light exposure to specific locations on a surface provided with linker molecules having protecting groups. In the exposed locations, the protecting groups are removed, resulting in one or more newly exposed reactive moieties on the linker. The surface is then contacted with a solution containing a coupling molecule. The coupling molecule can have at least one site that is reactive with the newly exposed reactive moiety on the linker and at least a second reactive site protected by one or more protecting groups. The desired coupling molecule is then coupled to the unprotected linker molecules. The process can be repeated to synthesize a large number of features in specific or positionally-defined locations on a surface (see, for example, U.S. Pat. No. 5,143,854 to Pirrung et al., U.S. Patent Application Publication Nos. 2007/0154946 (filed on Dec. 29, 2005), 2007/0122841 (filed on Nov. 30, 2005), 2007/0122842 (filed on Mar. 30, 2006), 2008/0108149 (filed on Oct. 23, 2006), and 2010/0093554 (filed on Jun. 2, 2008), each of which is herein incorporated by reference).

In some embodiments, a method of producing a two-dimensional array of features, can include obtaining a surface; and attaching the features to the surface, said features each comprising a collection of peptide chains of determinable sequence and intended length, wherein within an individual feature, the fraction of peptide chains within said collection having the intended length is characterized by an average coupling efficiency for each coupling step of at least about 98%. In some embodiments, the features are attached to the surface using a coupling formulation, comprising a solvent, a water soluble polymer, a water soluble coupling molecule, a water soluble neutralization reagent, and a water soluble coupling reagent. In some embodiments, the features are attached to the surface using a coupling formulation disclosed herein. In some embodiments, the coupling formulation is stripped away using water.

In some embodiments, a method of producing a two-dimensional array of features, can include obtaining a substrate comprising a planar layer comprising a metal and having an upper surface and a lower surface; and a plurality of pillars operatively coupled to the layer in positionally-defined locations, wherein each pillar has a planar surface extended from the layer, wherein the distance between the surface of each pillar and the upper surface of the layer is between about 1,000-5,000 angstroms, and wherein the plurality of pillars are present at a density of greater than about 10,000/cm$^2$; and coupling through a series of coupling reactions the features to the plurality of pillars, said features each comprising a collection of peptide chains of determinable sequence and intended length, wherein within an individual feature, the fraction of peptide chains within said collection having the intended length is characterized by an average coupling efficiency for each coupling step of at least about 98% or about 98.5%. In some embodiments, the coupling efficiency is substantially constant over each coupling cycle, and exceeds 98% or exceeds 98.5%. In some embodiments the average coupling efficiency exceeds 98% or exceeds 98.5% for each coupling step used to synthesize a 4-mer, or a 5-mer, or a 6-mer, or a 7-mer or longer polypeptide. In some embodiments the coupling efficiency is substantially constant and exceeds 98% or exceeds 98.5% for each coupling step used to synthesize a 4-mer, or a 5-mer, or a 6-mer, or a 7-mer or longer polypeptide. Coupling steps used to synthesize. In some embodiments, the features are coupled to the pillars using a coupling formulation, comprising a solvent, a water soluble polymer, a water soluble coupling molecule, a water soluble neutralization reagent, and a water soluble coupling reagent. In some embodiments, the features are coupled using a coupling formulation disclosed herein. In some embodiments, the coupling formulation is stripped away using water. In some embodiments, the surface of each pillar is parallel to the upper surface of the layer. In some embodiments, the surface of each pillar is substantially parallel to the upper surface of the layer.

In some embodiments, a method of preparing a substrate for attachment of features, can include obtaining a substrate comprising a planar layer having an upper surface and a lower surface; and a plurality of pillars operatively coupled to the layer in positionally-defined locations, wherein each pillar has a planar surface extended from the layer, wherein the distance between the surface of each pillar and the upper surface of the layer is between about 1,000-5,000 angstroms, and wherein the plurality of pillars are present at a density of greater than about 10,000/cm$^2$; and attaching one or more linker molecules to the plurality of pillars. In some embodiments, the linker molecule is attached using a linker formulation, comprising a solvent, a water soluble polymer, a water soluble linker molecule, and a water soluble coupling reagent. In some embodiments, the linker molecule is attached using a linker formulation disclosed herein. In some embodiments, linker molecule comprises a protecting group. In some embodiments, the surface of each pillar is parallel to the upper surface of the layer. In some embodiments, the surface of each pillar is substantially parallel to the upper surface of the layer.

In some embodiments, a method of preparing a surface for attachment of features, can include obtaining a surface and attaching a linker molecule to the surface using a linker formulation, comprising a solvent, a water soluble polymer, a water soluble linker molecule, and a water soluble coupling reagent. In some embodiments, linker molecule comprises a protecting group.

In some embodiments, a method of attaching a coupling reagent to a substrate, can include obtaining a substrate comprising a planar layer having an upper surface and a lower surface; and a plurality of pillars operatively coupled to the layer in positionally-defined locations, wherein each pillar has a planar surface extended from the layer, wherein the distance between the surface of each pillar and the upper surface of the layer is between 1,000-5,000 angstroms, wherein a linker molecule is attached to the surface of each pillar, and wherein the plurality of pillars are present at a density of greater than 10,000/cm$^2$; and attaching the coupling reagent to one or more linker molecules. In some embodiments, the coupling reagent is attached to the one or more linker molecules using a coupling formulation, comprising: a solvent, a water soluble polymer, a water soluble coupling molecule, a water soluble neutralization reagent, and a water soluble coupling reagent. In some embodiments, the coupling reagent is attached to the one or more linker molecules using a coupling formulation disclosed herein. In some embodiments, at least one the linker molecule is a deprotected linker molecule. In some embodiments, the coupling reagent is an amino acid. In some embodiments, the coupling reagent comprises a protecting molecule. In some embodiments, the coupling formulation is stripped away using water. In some embodiments, the surface of each pillar is parallel to the upper surface of the layer. In some embodiments, the surface of each pillar is substantially parallel to the upper surface of the layer.

In some embodiments, a method of attaching a coupling reagent to a surface can include obtaining a surface having a linker molecule attached to the surface and attaching the coupling reagent to the linker molecule using a coupling formulation, comprising a solvent, a water soluble polymer, a water soluble coupling molecule, a water soluble neutralization reagent, and a water soluble coupling reagent. In some embodiments, the linker molecule is a deprotected linker molecule. In some embodiments, the coupling reagent is an amino acid. In some embodiments, the coupling reagent comprises a protecting molecule. In some embodiments, the coupling formulation is stripped away using water.

In some embodiments, a method of producing a three-dimensional (e.g., porous) array of features, can include obtaining a porous layer attached to a surface; and attaching the features to the porous layer, said features each comprising a collection of peptide chains of determinable sequence and intended length, wherein within an individual feature, the fraction of peptide chains within said collection having the intended length is characterized by an average coupling efficiency for each coupling step of at least about 98.5%. In some embodiments, the features are attached to the surface using a photoactive coupling formulation, comprising a photoactive compound, a coupling molecule, a coupling reagent, a polymer, and a solvent. In some embodiments, the features are attached to the surface using a photoactive coupling formulation disclosed herein. In some embodiments, the photoactive coupling formulation is stripped away using water.

In some embodiments, described herein is a process of manufacturing an array. A surface comprising attached carboxylic acid groups is provided. The surface is contacted with a photoactive coupling solution comprising a photoactive compound, a coupling molecule, a coupling reagent, a polymer, and a solvent. The surface is exposed to ultraviolet light in a deep ultra violet scanner tool according to a pattern defined by a photomask, wherein the locations exposed to ultraviolet light undergo photo base generation due to the presence of a photobase generator in the photoactive coupling solution. The expose energy can be from 1 mJ/cm$^2$ to 100 mJ/cm$^2$ in order to produce enough photobase.

The surface is post baked upon exposure in a post exposure bake module. Post exposure bake acts as a chemical amplification step. The baking step amplifies the initially generated photobase and also enhances the rate of diffusion to the substrate. The post bake temperature can vary between 75° Celsius to 115° Celsius, depending on the thickness of the porous surface, for at least 60 seconds and not usually exceeding 120 seconds. The free carboxylic acid group is coupled to the deprotected amine group of a free peptide or polypeptide, resulting in coupling of the free peptide or polypeptide to the carboxylic acid group attached to the surface. This surface may be a porous surface. The synthesis of peptides coupled to a carboxylic acid group attached to the surface occurs in an N→C synthesis orientation, with the amine group of free peptides attaching to carboxylic acid groups bound to the surface of the substrate. Alternatively, a diamine linker may be attached to a free carboxylic acid group to orient synthesis in a C→N direction, with the carboxylic acid group of free peptides attaching to amine groups bound to the surface of the substrate.

The photoactive coupling solution can now be stripped away. In some embodiments, provided herein is a method of stripping the photoresist completely with deionized (DI) water. This process is accomplished in a developer module. The wafer is spun on a vacuum chuck for, e.g., 60 seconds to 90 seconds and deionized water is dispensed through a nozzle for about 30 seconds.

The photoactive coupling formulation can be applied to the surface in a coupling spin module. A coupling spin module can typically have 20 nozzles or more to feed the photoactive coupling formulation. These nozzles can be made to dispense the photoactive coupling formulation by means of pressurizing the cylinders that hold these solutions or by a pump that dispenses the required amount. In some embodiments, the pump is employed to dispense 5-8 cc of the photoactive coupling formulation onto the substrate. The substrate is spun on a vacuum chuck for 15-30 seconds and the photoactive coupling formulation is dispensed. The spin speed can be set to 2000 to 2500 rpm.

Optionally, a cap film solution coat is applied on the surface to prevent the unreacted amino groups on the substrate from reacting with the next coupling molecule. The cap film coat solution can be prepared as follows: a solvent, a polymer, and a coupling molecule. The solvent that can be used can be an organic solvent like N methyl pyrrolidone, dimethyl formamide, or combinations thereof. The capping molecule is typically acetic anhydride and the polymer can be polyvinyl pyrrolidone, polyvinyl alcohol, polymethyl methacrylate, poly (methyl iso propenyl) ketone, or poly (2 methyl pentene 1 sulfone). In some embodiments, the capping molecule is ethanolamine.

This process is done in a capping spin module. A capping spin module can include one nozzle that can be made to dispense the cap film coat solution onto the substrate. This solution can be dispensed through pressurizing the cylinder that stores the cap film coat solution or through a pump that precisely dispenses the required amount. In some embodiments, a pump is used to dispense around 5-8 cc of the cap coat solution onto the substrate. The substrate is spun on a vacuum chuck for 15-30 seconds and the coupling formulation is dispensed. The spin speed can be set to 2000 to 2500 rpm.

The substrates with the capping solution are baked in a cap bake module. A capping bake module is a hot plate set up specifically to receive wafers just after the capping film coat is applied. In some embodiments, provided herein is a method of baking the spin coated capping coat solution in a hot plate to accelerate the capping reaction significantly. Hot plate baking generally reduces the capping time for amino acids to less than two minutes.

The byproducts of the capping reaction are stripped in a stripper module. A stripper module can include several nozzles, typically up to 10, set up to dispense organic solvents such as acetone, iso propyl alcohol, N methyl pyrrolidone, dimethyl formamide, DI water, etc. In some embodiments, the nozzles can be designated for acetone followed by isopropyl alcohol to be dispensed onto the spinning wafer. The spin speed is set to be 2000 to 2500 rpm for around 20 seconds.

This entire cycle can be repeated as desired with different coupling molecules each time to obtain a desired sequence.

In some embodiments, an array comprising a surface of free carboxylic acids is used to synthesize polypeptides in an N→C orientation. In one embodiment, the carboxylic acids on the surface of the substrate are activated (e.g., converted to a carbonyl) to allow them to bind to free amine groups on an amino acid. In one embodiment, activation of carboxylic acids on the group of the surface can be done by addition of a solution comprising a carbodiimide or succinimide to the surface of the array. In some embodiments, carboxylic acids can be activated by addition of a solution comprising 1-ethyl-3-(3-dimethylaminopropyl)carbodiimide [EDC], N-hydroxysuccinimide [NHS], 1,3-diisopropylcarbodiimide [DIC], hydroxybenzotriazole [HOBt], 1-Hydroxy-7-azabenzotriazole [HOAt], (O-(7-azabenzotriazol-1-yl)-N,N,N',N'-tetramethyluronium hexafluorophosphate) [HATU], benzotriazol-1-yl-oxytripyrrolidinophosphonium hexafluorophosphate [PyBOP], or N,N-diisopropylethylamine [DIEA] to the surface of the array. The activation solution is washed away and the surface of the array is prepared for addition of an amino acid layer (i.e., one amino acid at each activated carboxylic acid group). Carboxylic acid groups remain activated for up to 2, 3, 4, 5, 6, 7, 8, 9, or 10 hours.

Addition of a solution comprising an amino acid with a free amine group to the activated carboxylic acid surface of the array results in binding of a single amino acid to each carboxylic acid group. In some embodiments, the amino acid comprises an amino acid with protected amine groups. Using a photosensitive chemical reaction, the protecting group can be removed from the amine group of selected amino acids at site-specific locations using a reticle. For example, Fmoc-protected amino acids are mixed in a solution comprising a photobase generator. Upon exposure of the solution on the array to a specific frequency of light at site-specific locations, the photobase generator will release a base which will deprotect the amino acid, resulting in coupling of the amino acid to the activated carboxylic acid group on the surface of the array. Another method involves using a protected base that is then unprotected by a photoacid released by a photoacid generator upon light exposure. In some embodiments, the protected base is N-Boc-piperidine or 1,4-bis(N-Boc)-piperazine.

After a completed layer of amino acids is coupled, remaining uncoupled activated carboxylic acids are capped to prevent nonspecific binding of amino acids on subsequent synthesis steps. The steps of activation, addition of an amino acid layer, and capping are repeated as necessary to synthesize the desired polypeptides at specific locations on the array.

In some embodiments, peptides synthesized in the N→C terminus direction can be capped with a diamine molecule to enhance binding properties of selected polypeptide sequences to a biological molecule, e.g., an antibody. In other embodiments, peptides synthesized in the C→N direction can be capped with a dicarboxylic acid molecule to enhance binding properties of selected sequences to a biological molecule.

While synthesizing polypeptides in parallel on the surface of an array, the method described herein ensures complete activation of carboxylic acid on the surface of the array. Due to stability of the activated ester for an extended period of time, 2, 3, 4, 5, 6, 7, 8, 9, 10, 11, 12, 13, 14, 15, 16, 17, 18, 19, 20, 21, 22, 23, 24, 25 or more coupling cycles may be completed after a single activation step (e.g., to couple an entire layer of 2-25 or more different amino acids at different locations on the array). As the coupling occurs during hard bake (heating in a hot plate at 85-90° Celsius for 90 seconds immediately after coating) and due to the presence of excess amino acid in the solution, complete 100% deprotection of Fmoc-protected amino acid may not be required for significantly high coupling yields. After addition of all amino acids and capping, all free activated carboxylic acids are either coupled or capped, thus resulting in high efficiency and accuracy of polypeptide synthesis.

Methods of Use of Arrays

Also disclosed herein are methods of using substrates, formulations, and/or arrays. Uses of the arrays disclosed herein can include research applications, therapeutic purposes, medical diagnostics, and/or stratifying one or more patients.

Any of the arrays described herein can be used as a research tool or in a research application. In one aspect, arrays can be used for high throughput screening assays. For example, enzyme substrates (i.e., peptides on a peptide array described herein) can be tested by subjecting the array to an enzyme and identifying the presence or absence of enzyme substrate(s) on the array, e.g., by detecting at least one change among the features of the array.

Arrays can also be used in screening assays for ligand binding, to determine substrate specificity, or for the identification of peptides that inhibit or activate proteins. Labeling techniques, protease assays, as well as binding assays useful for carrying out these methodologies are generally well-known to one of skill in the art.

In some embodiments, an array can be used to represent a known protein sequence as a sequence of overlapping peptides. For example, the amino acid sequence of a known protein is divided into overlapping sequence segments of any length and of any suitable overlapping frame, and peptides corresponding to the respective sequence segments are in-situ synthesized as disclosed herein. The individual peptide segments so synthesized can be arranged starting from the amino terminus of the known protein.

In some embodiments, an array is used in a method wherein the antigenic representation of the array includes at least one region where the whole antigen sequence of a known protein is spanned via epitope sliding; the immunoactive regions of the antigen are determined by contacting one or more clinical samples on the array or a plurality of different arrays, and the set of peptide sequences required to represent the known protein antigen are reduced.

In some embodiments, a sample is applied to an array having a plurality of random peptides. The random peptides can be screened and BLASTed to determine homologous domains with, e.g., a 90% or more identity to a given antigenic sequence. In some aspect, the whole antigenic sequence can then be synthesized and used to identify potential markers and/or causes of a disease of interest.

In some embodiments, an array is used for high throughput screening of one or more genetic factors. Proteins associated with a gene can be a potential antigen and antibodies against these proteins can be used to estimate the relation between gene and a disease.

In another example, an array can be used to identify one or more biomarkers. Biomarkers can be used for the diagnosis, prognosis, treatment, and management of diseases. Biomarkers may be expressed, or absent, or at a different level in an individual, depending on the disease condition, stage of the disease, and response to disease treatment. Biomarkers can be, e.g., DNA, RNA, proteins (e.g., enzymes such as kinases), sugars, salts, fats, lipids, or ions.

Arrays can also be used for therapeutic purposes, e.g., identifying one or more bioactive agents. A method for identifying a bioactive agent can comprise applying a plurality of test compounds to an array and identifying at least one test compound as a bioactive agent. The test compounds can be small molecules, aptamers, oligonucleotides, chemicals, natural extracts, peptides, proteins, fragment of antibodies, antibody like molecules or antibodies. The bioactive agent can be a therapeutic agent or modifier of therapeutic targets. Therapeutic targets can include phosphatases, proteases, ligases, signal transduction molecules, transcription factors, protein transporters, protein sorters, cell surface receptors, secreted factors, and cytoskeleton proteins.

In another aspect, an array can be used to identify drug candidates for therapeutic use. For example, when one or more epitopes for specific antibodies are determined by an assay (e.g., a binding assay such as an ELISA), the epitopes can be used to develop a drug (e.g., a monoclonal neutralizing antibody) to target antibodies in disease.

In one aspect, also provided are arrays for use in medical diagnostics. An array can be used to determine a response to administration of drugs or vaccines. For example, an individual's response to a vaccine can be determined by detecting the antibody level of the individual by using an array with peptides representing epitopes recognized by the antibodies produced by the induced immune response. Another diagnostic use is to test an individual for the presence of biomarkers, wherein samples are taken from a subject and the sample is tested for the presence of one or more biomarkers.

Arrays can also be used to stratify patient populations based upon the presence or absence of a biomarker that indicates the likelihood a subject will respond to a therapeutic treatment. The arrays can be used to identify known biomarkers to determine the appropriate treatment group. For example, a sample from a subject with a condition can be applied to an array. Binding to the array may indicate the presence of a biomarker for a condition. Previous studies may indicate that the biomarker is associated with a positive outcome following a treatment, whereas absence of the biomarker is associated with a negative or neutral outcome following a treatment. Because the patient has the biomarker, a health care professional may stratify the patient into a group that receives the treatment.

In some embodiments, a method of detecting the presence or absence of a protein of interest (e.g., an antibody) in a sample can include obtaining an array disclosed herein and contacted with a sample suspected of comprising the protein of interest; and determining whether the protein of interest is present in the sample by detecting the presence or absence of binding to one or more features of the array. In some embodiments, the protein of interest can be obtained from a bodily fluid, such as amniotic fluid, aqueous humour, vitreous humour, bile, blood serum, breast milk, cerebrospinal fluid, cerumen, chyle, endolymph, perilymph, feces, female ejaculate, gastric acid, gastric juice, lymph, mucus, peritoneal fluid, pleural fluid, pus, saliva, sebum, semen, sweat, synovial fluid, tears, vaginal secretion, vomit, or urine.

In some embodiments, a method of identifying a vaccine candidate can include obtaining an array disclosed herein contacted with a sample derived from a subject previously administered the vaccine candidate, wherein the sample comprises a plurality of antibodies; and determining the binding specificity of the plurality of antibodies to one or more features of the array. In some embodiments, the features comprise a plurality of distinct, nested, overlapping peptide chains comprising subsequences derived from a source protein having a known sequence.

EXAMPLES

Figure 1B:
Figure 1B:
Figure 1B:

The following examples illustrates a method of identifying biomarkers for celiac diseases. The biomarkers include a set of peptides obtained from known antigens in celiac disease, including, but not limited to alpha, beta, gamma, and omega gliadin, tissue transglutaminase (tTG), and the deamidated modification thereof. The method includes synthesizing a peptide library of 12-mer peptides based on these known celiac antigens. In some embodiments, sequences of the 12-mer peptides are identified by shifting through the amino acid sequences of the known celiac antigens by either two or three amino acid at a time. FIG. 1A illustrates identifying 12-mer sequences based on shifting by two amino acids along the alpha/beta gliadin sequence. FIG. 1B illustrates deaminating the 12-mer peptides one or two glutamines at a time to increase the size of the peptide library. The peptide library was then synthesized on a microarray, as described in more detail below, which were found to be significantly better than other conventional peptide synthesis techniques. The coupling yield during synthesis of the peptides on the array was continually monitored for peptide yield, purity and sequence fidelity using fluorescence, mass spectrometry, and monoclonal antibody binding substrate assays. To identify biomarkers based on B cell epitopes of native and deamidated gliadin derived peptides (GPs), peptide microarrays including 2.1 million different peptides from the peptide library of GPs, including triple duplicates of each peptide, were synthesized, picked and placed onto 96 pillar plates.

Example 1: Wafer Substrate Preparation

Prime grade 300 mm silicon wafers, having p-type boron, (1,0,0)-Orientation, 1-5 Ohm/cm and 725 µm thickness, were obtained from Process Specialties. The wafers were deposited with 1000 Å thermal oxide by dry oxidation at 1000° Celsius in a furnace under pure oxygen atmosphere for 2 hours. Commercial photoresist P5107 was spin coated on the wafers at 2000 rpm for 40 seconds using the Sokudo RF3S Coat/Develop Track. The wafers were exposed with an inverse zero layer mask using the Nikon NSR S205 KrF Scanner at a wavelength of 248 nm. This was followed by post exposure bake at 110° Celsius for 90 seconds and then developed using the developer NMD-3 at 2.38% (TOK America). Oxide etching was performed by wet oxide etch of the wafers using buffered hydrofluoric acid which was prepared by mixing 5 parts of 40 weight % of ammonium fluoride (Sigma) with 1 part of 49 weight % of hydrofluoric acid (Sigma) for 1 minute. The wafers were then stripped with Nanostrip (CyanTek) for 24 hours, finally washed with DI Water, and sonicated in DI Water for 10 minutes. This process as illustrated in FIG. 3A resulted in a substrate with a feature area that measured a height of 1000 Å containing thermal oxide while containing silicon in the non-feature area.

A DI 5000 AFM system was used to measure the roughness and calculate the density of the substrate. FIG. 3B shows the pillars and their dimensions formed after the process described above and illustrated in FIG. 3A. FIG. 3C illustrates the root mean square (RMS) roughness of the substrate. The density of the substrate was calculated to be approximately 100-150 pM.

Example 2: Wafer Surface Derivatization

Wafers were copiously washed with DI water for 5 minutes and spin coated with a solution containing 1.25% (v/v) of 3-aminopropyltriethoxysilane [APTES] (Sigma Aldrich) in N-methyl-pyrollidone [NMP] (BDH) and left at room temperature for 15 minutes. Curing of the wafers was done at 120° Celsius for 60 minutes under $N_2$ atmosphere. Wafers were then spin coated with a coupling solution containing 2 weight % of Fmoc-Gly-OH (Anaspec), 2 weight % of HOBt (Anaspec) and 2 weight % of N,N'-diisopropylcarbodiimide [DIC] (Sigma Aldrich) in NMP and baked at 60° Celsius for 5 minutes. This enabled coupling of Fmoc-Glycine to the free amine present in APTES. Wafers were then rinsed with NMP and then capped with 50% (v/v) of Acetic Anhydride mixed with 50% of NMP to cap any remaining free amines which have not been coupled. Wafers were stripped with acetone (BDH) and isopropyl alcohol [IPA] (BDH). Fmoc protection of glycine was removed by spin coating the wafer with 5% (v/v) of piperidine (Sigma Aldrich) in NMP and baking at 80° Celsius for 300 seconds. The linker Fmoc-(PEG)$_4$-COOH (Anaspec) was then coupled to the wafer surface by spin coating a coupling solution containing 2 weight % of the linker, 2 weight % of HOBt (Anaspec) and 2 weight % of N,N'-diisopropylcarbodiimide [DIC] in NMP and baked at 90° Celsius for 120 seconds. Wafers were then rinsed with NMP and subsequently capped with 50% (v/v) of acetic anhydride mixed with 50% of NMP to cap any remaining free amines. Wafers were stripped with acetone and IPA to complete the surface derivatization process.

Example 3: Peptide Array Synthesis

Figure 4:
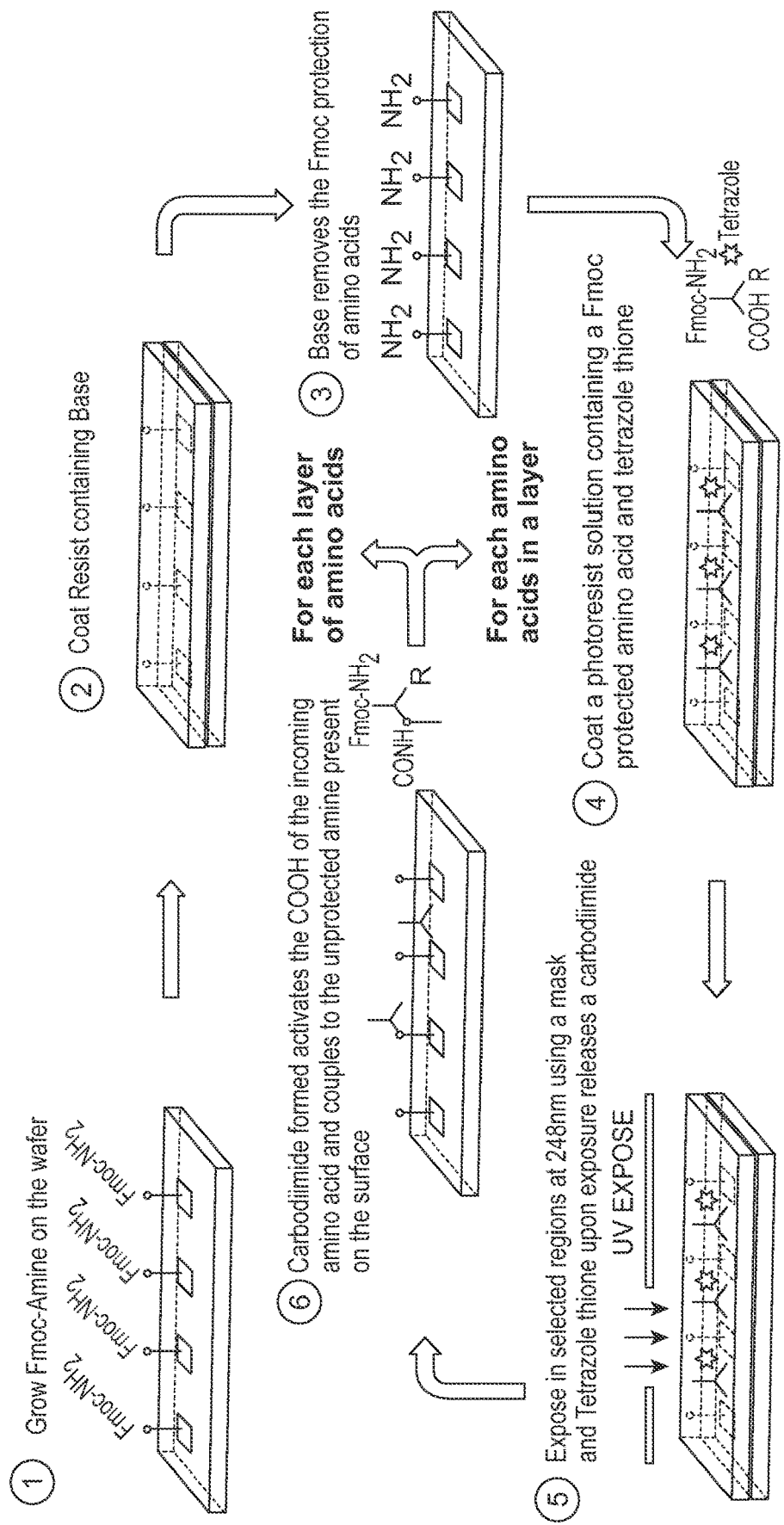
FIG. 4 shows peptide array synthesis, according to an embodiment.

The steps performed for synthesizing the peptides on the array are illustrated in FIG. 4 and described in detail above.

Activation Solution:

An amino acid activation solution was prepared as follows: 1% by weight of poly(methyl methacrylate) [PMMA] (Polysciences) was dissolved in N-methyl pyrollidone by sonication for 10 minutes. 2% by weight of Fmoc-amino acid (Anaspec) was then added to the solution followed by addition of 2% by weight of HOBt (Anaspec). Finally, 1% by weight of tetrazole thione was added to the solution. The solution was then filtered using a 0.05 µm filtration setup.

Carbodiimide Formation Mechanism:

The photo activated carbodiimide coupling was performed as follows:

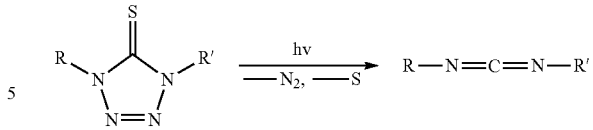

Tetrazole thiones were used that upon exposure at 248 nm undergo a ring opening mechanism and release a carbodiimide that activates the carboxylic acid groups of amino acids being coupled to the wafer. Esters of —OBt or —OAt were formed upon addition of HOBt or HOAt. Thus, tetrazole thiones at 248 nm were used to photoactivate an amino acid to form a stable ester for efficient coupling.

Amino Acid Coupling:

A base resist solution containing 1 weight % of polymer and 3 weight % of piperidine dissolved in NMP was spin coated onto the wafer at 3000 rpm for 30 seconds and soft baked at 65° Celsius for 1 minute in a hot plate. Now the wafer was baked at 80° Celsius for 300 seconds. Fmoc protection was removed in all features leaving the unprotected amine group. The incoming amino acid activation solution was spin coated onto a wafer at 3000 rpm for 30 seconds and soft baked at 65° Celsius for 1 minute in a hot plate. Now the wafer was exposed using a reticle which exposes desired features for which the incoming amino acid needs to be coupled at an exposure dose of 120 mJ/cm$^2$ and then hard baked at 85° Celsius for 90 seconds in a hot plate. As described above, tetrazole thione upon exposure releases a carbodiimide and selective activation of amino acid was achieved in the exposed features. Therefore, the incoming Fmoc-protected amino acid present in the activation solution was activated and coupled to the unprotected amine present on the wafer in the same step completing the coupling of one layer of amino acid. Each coupling layer comprises reticles for each incoming Fmoc amino acid to be coupled, which expose features independent of the other reticles used for the same layer. After coupling all amino acids for a particular layer, the wafer was then spin coated with a solution of 50 weight % of NMP and 50 weight % of acetic anhydride to cap any remaining unprotected amine of the wafer that had no amino acid coupled for this particular layer. The wafer was stripped in acetone and IPA to remove any base resist present on the surface after each step. The whole process was repeated for each individual coupling layer of amino acids designed to be coupled to complete the synthesis of peptide chains attached to the array surface.

Side Chain Protection Removal:

After the completion of peptide synthesis, any remaining side group protections present for any coupled amino acids were removed to enable biological activity of the peptide. A side chain protection removal solution was prepared by mixing 95 weight % trifluoroacetic acid [TFA] (Sigma Aldrich) and 5 weight % DI water. The wafers were reacted with the side chain protection removal solution for 90 mins. This step was followed by washing the wafer successively with TFA (for 5 mins), IPA (for 5 mins), NMP (for 5 mins), neutralize with 5 weight % of DIEA (Alfa Aesar) in NMP (for 5 mins), and followed by washing the wafer successively with NMP (for 5 mins) and IPA (for 5 mins).

Example 4: Purity Analysis of Synthesized Peptides

Mass Spectroscopy Analysis:

Peptide LKWLDSFTEQ (SEQ ID NO: 128 equals 1 in 24598PCT) was synthesized as described in Examples 1-3 and cleaved from the wafer substrate. The peptide was dissolved in 20-70% ceric ammonium nitrate [CAN] for 1.75 mins and loaded at 1.5 ml/min at 35° Celsius in a Phenomenex Luna column. The peptide mass was measured and matched the expected mass as shown in FIG. 5A.

Figure 5C:
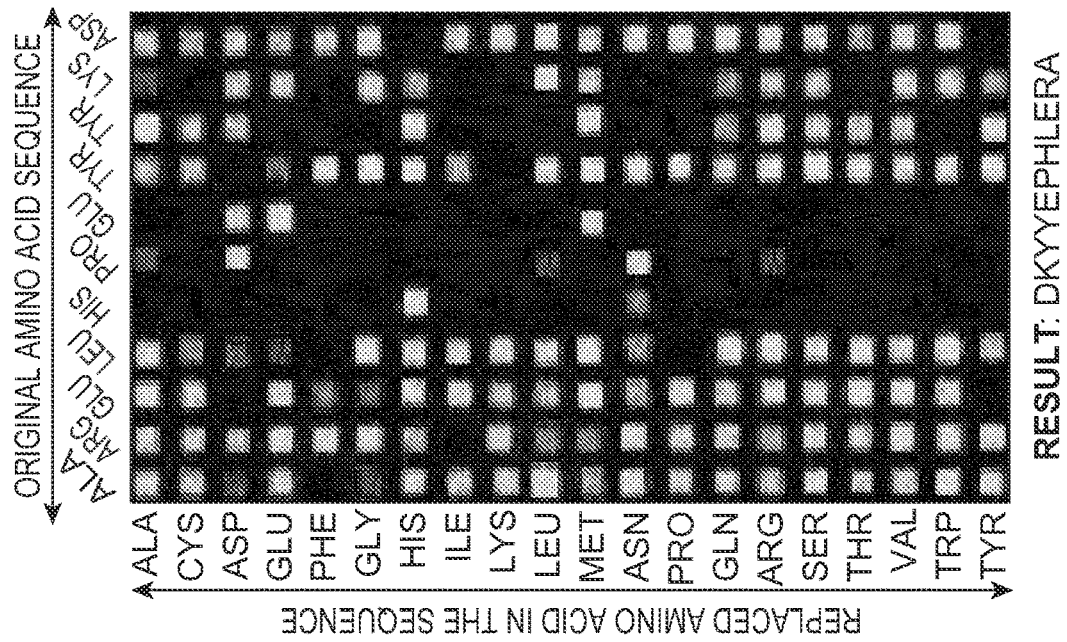
Figure 5B:
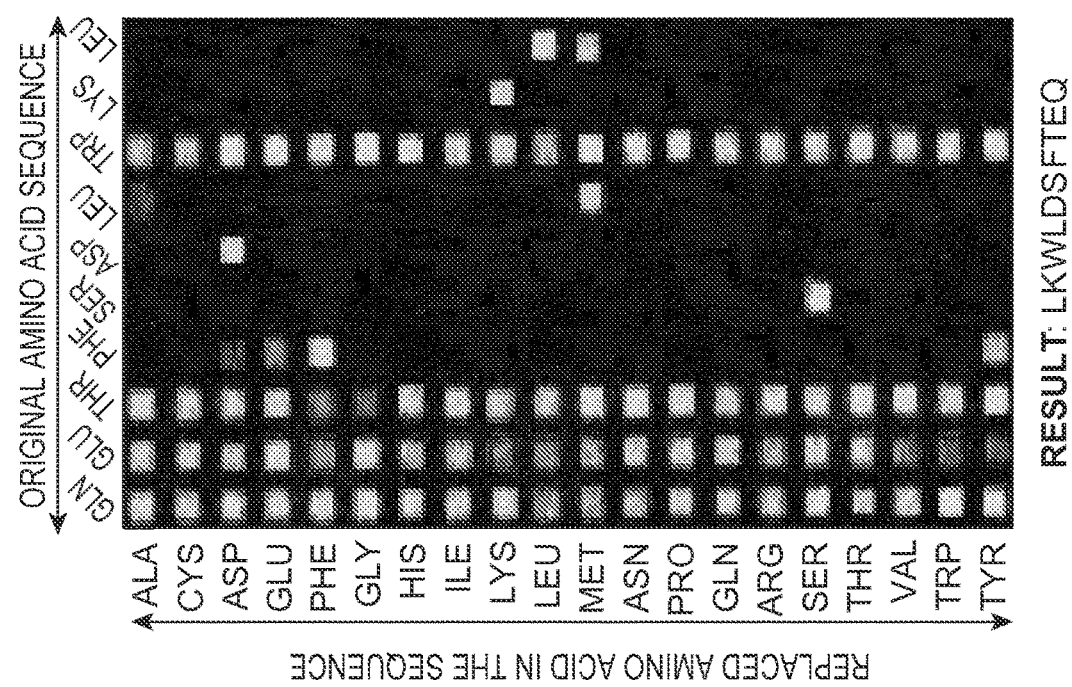

Fluorescein Quality Control:

As a second control of the peptide synthesis process, end-of-line fluorescein quality control was performed. The final amino acid in each peptide sequence was deprotected by base (10% (v/v) of piperidine in NMP) for 20 minutes and coupled in a solution containing 1 weight % 5(6)-FAM (Anaspec), 2 weight % of DIC and 2 weight % of HOBt dissolved in NMP for 30 minutes. This was followed by washing steps successively with NMP (for 5 mins), ethanol (for 5 mins), mixture of 50 weight % EDA (Sigma Aldrich) and 50 weight % of ethanol for 30 mins, ethanol for 15 mins and IPA for 5 mins Based on the fluorescence signal of the probes the individual coupling yield of each amino acid coupling step and total coupling yield as described in more detail in the International Patent Application No. PCT/US2013/062773, the disclosure of which is hereby incorporated by reference in its entirety of all purpose. Examples for peptides LKWLDSFTEQ (SEQ ID NO: 128) and DKYYEPHLERA (SEQ ID NO: 129) are shown in FIGS. 5B and 5C.

Example 5: Celiac Disease Sample Assay

To discover a novel biomarker for the diagnosis of celiac disease (CD), sera was collected from three sources: a cohort collected as part of a previous study at Mayo Clinic[2] (48 CD cases and 50 controls), a cohort from ARUP Labs (42 CD cases and 29 controls), and a commercially obtained cohort (12 rheumatoid arthritis (RA) cases and 7 systemic lupus erythematosus (SLE) cases). Further sera from a validation cohort (306 seropositive CD cases and 1590 controls), which was assembled in the previous study of the seropositivity of CD in a community[19], were used for evaluating the diagnostic utility of identified or newly developed peptide sets from the cohort. Tables 3 and 4 show the demographic characteristics of the study population. All samples were handled by standard procedures and stored at −80° Celsius. All samples were probed using 1:101 Primary Antibody Dilution and 1:2000 Secondary Antibody Dilution and scanned on a Nikon Total Solution Platform consisting of Hamilton fluidics station and Gen 2 Microarray fluorescence scanner.

TABLE 3

Clinical Characteristics of the study population.

| | | AGE | | SEX | |
|---|---|---|---|---|---|
| Group | N | MEAN | RANGE | MALE | FEMALE |
| Celiac disease autoimmunity | 90 | 39.42 | 19.5-60.2 | 43% | 57% |
| Rheumatoid Arthritis | 12 | 40.58 | 20.10-68.79 | 50% | 50% |
| Systemic Lupus Erythematosus | 7 | 34.51 | 25.7-56.98 | 43% | 57% |
| Healthy controls | 79 | 40.22 | 19.67-63.33 | 48% | 52% |

TABLE 4

| | | AGE | | SEX | |
|---|---|---|---|---|---|
| Group | N | MEAN | RANGE | MALE | FEMALE |
| Celiac disease autoimmunity | 306 | 35.18 | 18.11-49.91 | 38% | 62% |
| Rheumatoid Arthritis | 75 | 38.97 | 20.1-56.7 | 50% | 50% |
| Systemic Lupus Erythematosus | 40 | 36.5 | 25.3-45.6 | 37.50% | 62.50% |
| Healthy controls | 1475 | 35.33 | 18.5-69.8 | 33.89% | 66.10% |

First, 188 sera samples from a set of 90 untreated patients with CD and 98 controls were analyzed for IgG and IgA reactivity to the GPs attached to the surface of the microarray for determining 3-mer amino acid subsequences that have the highest occurrences amongst GPs, which are most active for the celiac samples. Two distinct consensus GP sets (gliadin derived peptide sequences) were identified for discriminating CD from controls in the cohort, exhibiting 80% sensitivity and 85% specificity for a peptide set #1 for IgG reactivity, while 86% sensitivity and 89% specificity in peptide set #2 for IgA reactivity, as illustrated in Table 5.

TABLE 5

Identified GP sets for the diagnosis of CD in the training cohort

| Peptide Set | | Celiac Positive* | | | Sensitivity % (95% CI) | Specificity % (95% CI) |
|---|---|---|---|---|---|---|
| | | Positive | Negative | Total | | |
| Peptide Set #1 | Positive | 72 | 15 | 87 | | |
| | Negative | 18 | 83 | 101 | | |
| (IgG) | Total | 90 | 98 | 188 | 80% (71-87) | 85% (76-91) |
| Peptide Set #2 | Positive | 77 | 11 | 88 | | |
| | Negative | 13 | 87 | 100 | | |
| (IgA) | Total | 90 | 98 | 188 | 86% (77-91) | 89% (82-94) |

*Celiac Positive, positive was defined by the current standard diagnosis of CD, composed of CD serology and/or duodenal biopsy.

Example 6: Creation of Novel, Synthetic Biomarkers for CD Diagnosis

Figure 7:
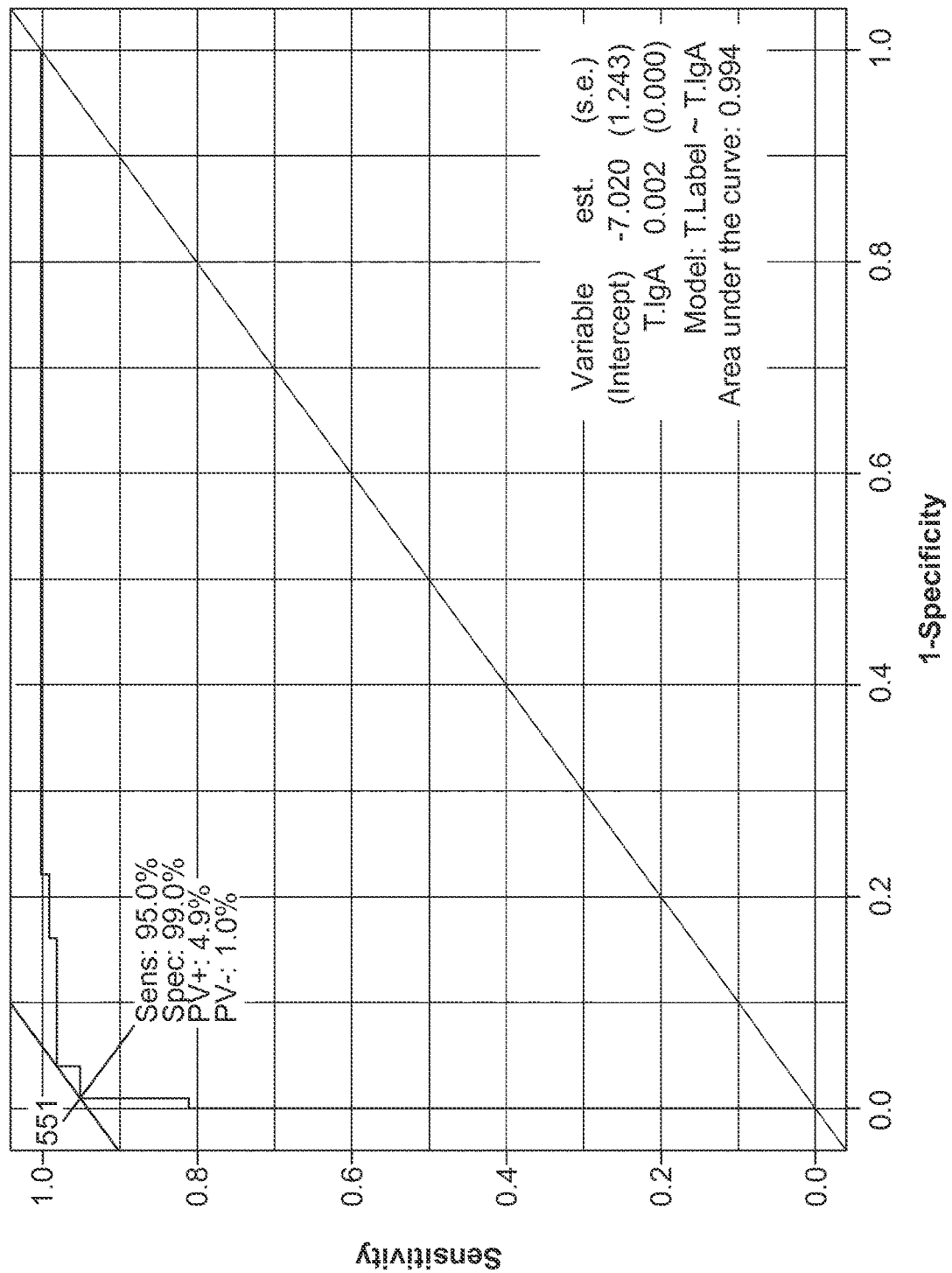
FIG. 7 illustrates a Receiver Operating Curve for deamidated gliadian-derived peptides (DGPs), according to an embodiment. This ROC curve serves as an example for one of the synthetic deamidated gliadin-derived peptides with a high AUC=0.99. The ROC curve is plotted based on 1-specificity and sensitivity under each threshold for each sequence.

A matrix table was generated, as illustrated in FIGS. 6A and 6B, showing the percentage of occurrence of among 3-mer subsequences included in the GPs most active for the celiac samples. To improve diagnostic accuracy for CD, a novel set of sequences was determined by combining 3-mer subsequences having a high occurrence rate included in this matrix table with other high-occurrence 3-mer sequences from the matrix table, random 3-mer or random 6-mer peptides to form 6-mer, 9-mer, 12-mer and 15-mer peptides, respectively. To assess the accuracies of the newly randomized peptide biomarker sequences (6-mers to 15-mers) for the CD diagnosis, random forest (RF),[20] which is a statistical algorithm that creates voting classes of decision-making trees to evaluate the significance of each biomarker and classify samples, was used. The newly identified and RF-validated peptide sequences were then synthesized on a 110 k peptide microarray with triple duplicates. 127 newly randomized and different peptides (SEQ ID NOS: 1-127) of these newly randomized peptide sequences displayed significantly improved sensitivity (IgG=97% or IgA=99%) and specificity (98% or 100%) (p<0.001) for CD diagnosis, when compared to the peptide set #1 and #2 from Example 5 using the current standard CD serology test with ELISA kits (Table 6). Table 1 and 2 lists the 127 peptides (SEQ ID NOS: 1-127) divided into sets #3 and #4 based on the peptides activity in either the IgG or the IgA assay, respectively. The cross-validated area under the curve of a Receiver Operating Characteristic (ROC) curve using these 127 peptide sequences for predicting CD autoimmunity (CDA) with IgA reactivity was 0.99, as illustrated in FIG. 7.

Figure 8:
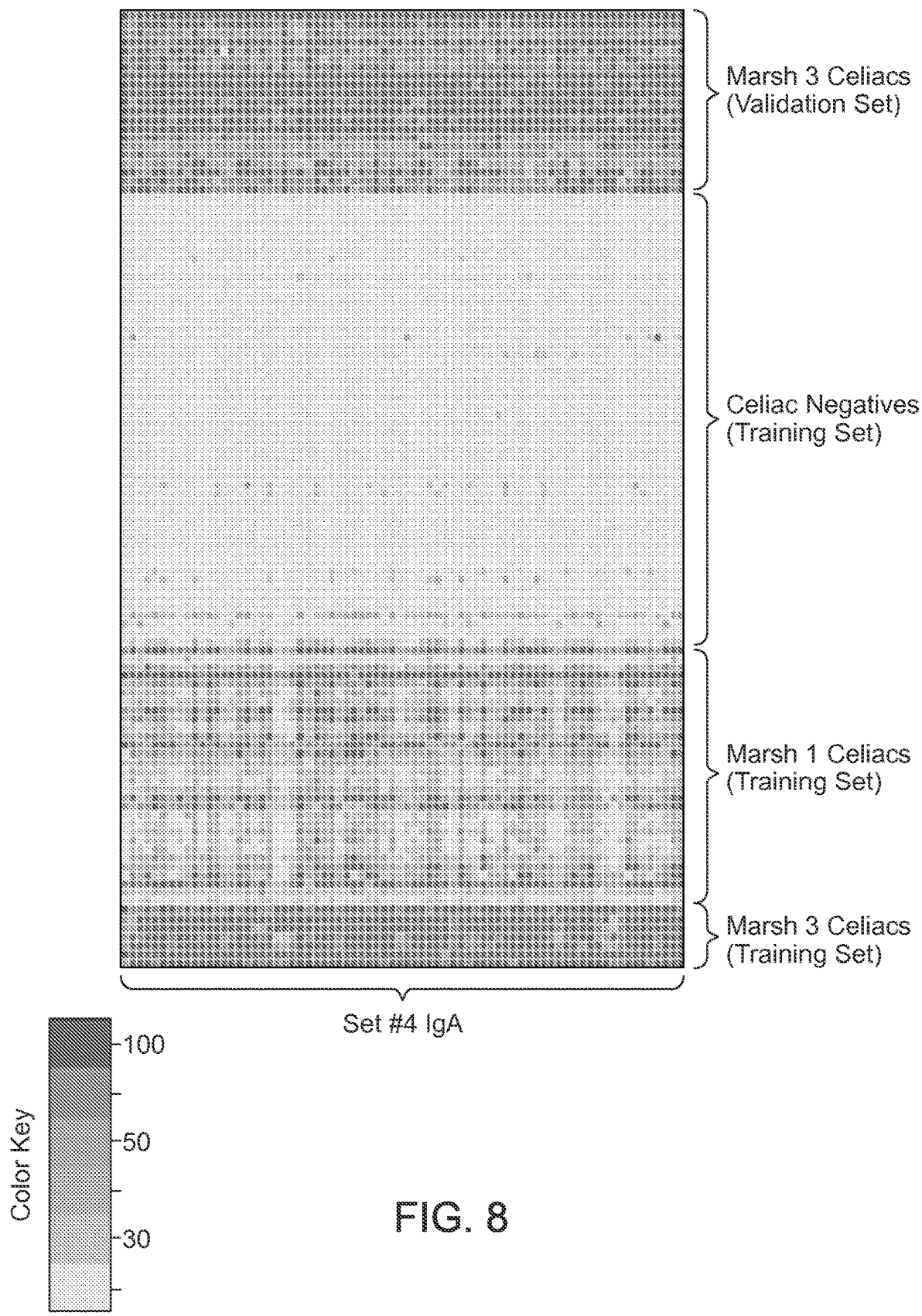
FIG. 8 illustrates a Heat map based on duodenal pathology with Marsh classification, according to an embodiment. The heat map showed two clusters of high or low antibody binding intensity of the identified peptide in the set. Moreover, 33 patients with CD autoimmunity who were subsequently diagnosed with CD after blood drawn in the validation cohort also showed high binding intensity, which was similar to the high intensity group in the training set.
Figure 9:
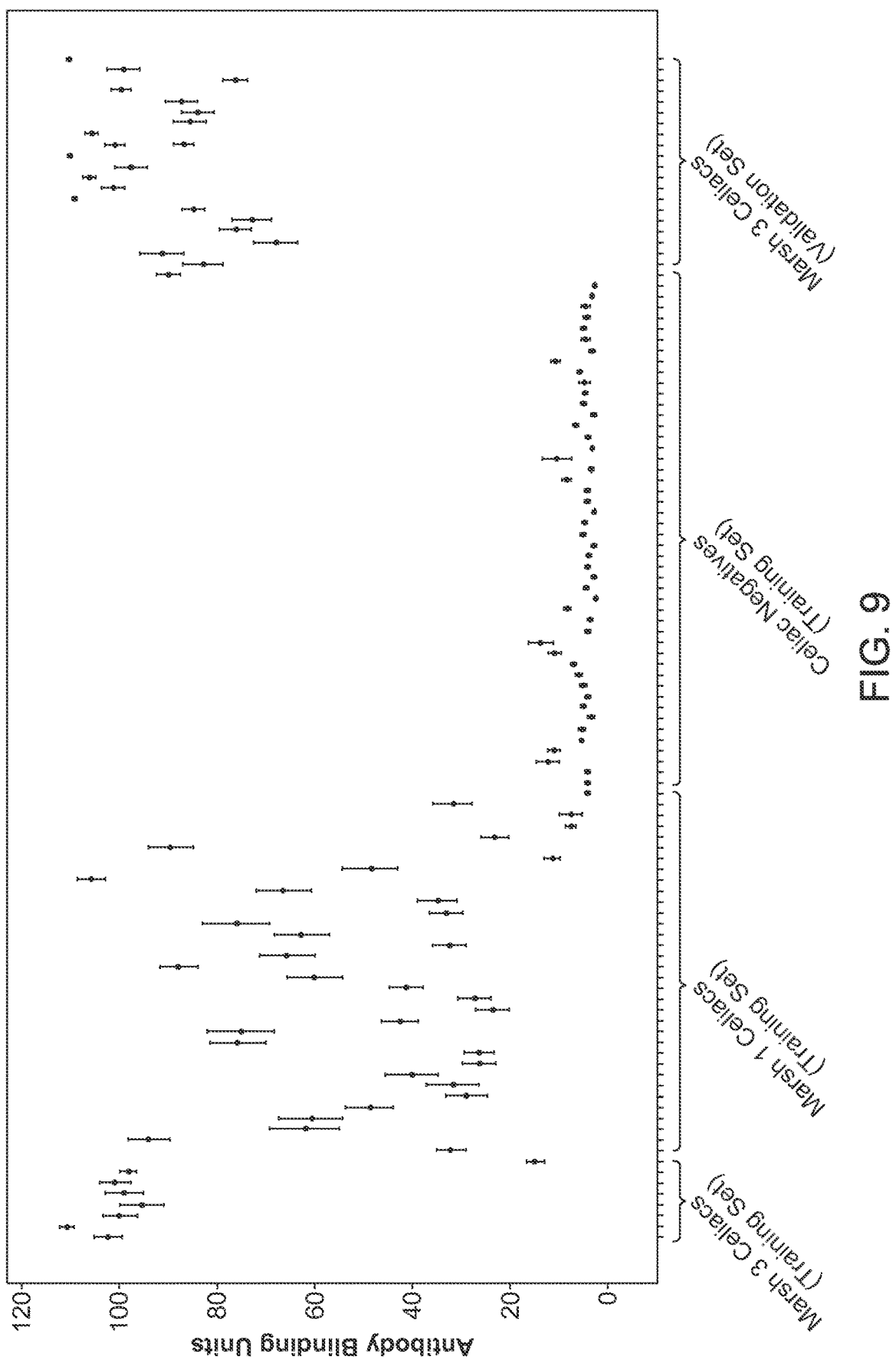
FIG. 9 illustrates error bars based on duodenal pathology with Marsh classification, according to an embodiment. A graphical representation of the data obtained is represented using error bars. Error bars for each sample across the cohort is represented using the mean of the peptide units across the epitope set along with its corresponding 95% Confidence Interval [CI].

Example 7: Relationship of Immune Reactivity of the Novel B Cell Epitopes with CD Severity To evaluate the correlation between duodenal pathology of CD and immune reactivity to the identified peptide sets, sera of 48 clinically proven CD cases were used. While none of the peptides in set #1 and set #2 from Example 5 could categorize sera samples based on the severity of enteropathy, 127 newly randomized peptides (SEQ ID NOS: 1-127) were able to distinguish between severe and less severe CD cases, as determined by the Marsh scoring system for small intestinal pathology, as illustrated in FIGS. 8 and 9.

subjects, who subsequently had clinically detected CD, exhibiting higher intensity than those who have not had CD detected subsequently.

To assess the training and validation set classification accuracies of the selected peptide biomarkers, random forest (RF)[20] was used. Using the newly identified peptide biomarkers (SEQ ID NOS: 1-127) to diagnose the training set (n=188; 90 CD and 98 controls), RF had an overall accuracy of 98.9% [Out-of-Bag (OOB) Error 1.1%, a positive predictive value (PPV) of 100%, and a negative predictive value (NPV) of 98.2%]. When the same set of biomarkers were used to classify validating set sera (n=1896; 306 CDA and 1590 control), which played no part in the biomarker selection process, RF distinguished CDA samples from controls with equal accuracy (prediction error of 1.1%, PPV of 100.0%, and NPV of 98.2%). When these autoantibody biomarkers (SEQ ID NOS: 1-127) were used to classify all CD and control samples simultaneously (n=2084; 396 CD, 1688 control) in RF, they did so with a 99.1% sensitivity and 100% specificity.

In CD, some B-cell epitopes of gliadin have been shown to be linear.[15] It is well recognized that antibodies recognize

TABLE 6

Discriminant power of the novel peptide sets of discontinuous B-cell epitopes for the diagnosis of CD

| Peptide Set | | Celiac Positive* | | | Sensitivity % (95% CI) | Specificity % (95% CI) |
|---|---|---|---|---|---|---|
| | | Positive | Negative | Total | | |
| Peptide Set #3 (IgG) | Positive | 87 | 2 | 89 | | |
| | Negative | 3 | 96 | 99 | | |
| | Total | 90 | 98 | 188 | 97% (91-99) | 98% (93-99) |
| Peptide Set #4 (IgA) | Positive | 89 | 0 | 89 | | |
| | Negative | 1 | 98 | 99 | | |
| | Total | 90 | 98 | 188 | 99% (94-100) | 100% (96-100) |
| tTG IgA, ELISA+ | | | | | 93% (87-97) | 98% (93-99) |
| DGPs IgA, ELISA++ | | | | | 87% (80-94) | 92% (86-96) |

*Celiac Positive, positive was defined by the current standard diagnosis of CD, composed of CD serology and/or duodenal biopsy; +, tTG = Anti tissue transglutaminase-IgA antibodies to tissue transglutaminase with an enzyme-linked immunosorbent assay (ELISA) that uses human recombinant antigen manufactured by Inova Diagnostics, San Diego CA; ++, DGPs = Deamidated gliadin-derived peptides-IgA antibodies to deamidated gliadin peptide with an enzyme-linked immunosorbent assay (ELISA) that uses human recombinant antigen manufactured by Inova Diagnostics, San Diego CA

Example 8: Evaluation of the Novel B Cell Epitopes

Figure 10A:
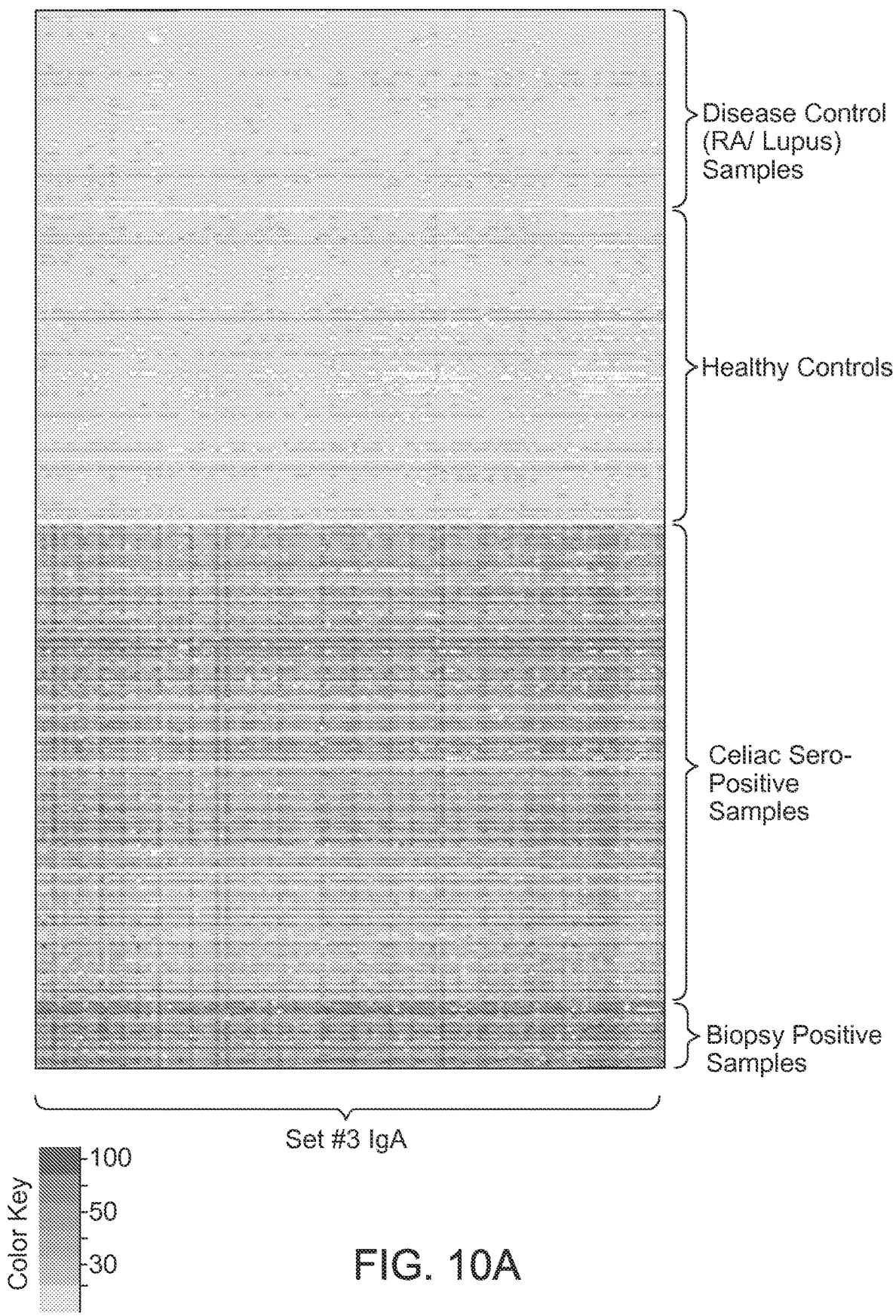
FIGS. 10A, 10B and 10C illustrate heat maps of antibody binding intensity in Validation set samples, according to an embodiment. (A) and (B) Heat-map shows antibody binding data for a novel peptide set with high significance values to differentiate celiac positives from controls and disease controls. Fluorescent binding intensities are converted to antibody binding units after normalizing using the threshold values for each peptide. (C) This shows the natural subgrouping of CD positives and negatives based on a clustering algorithm from a Vibrant Analyzer in a validation cohort.
Figure 10B:
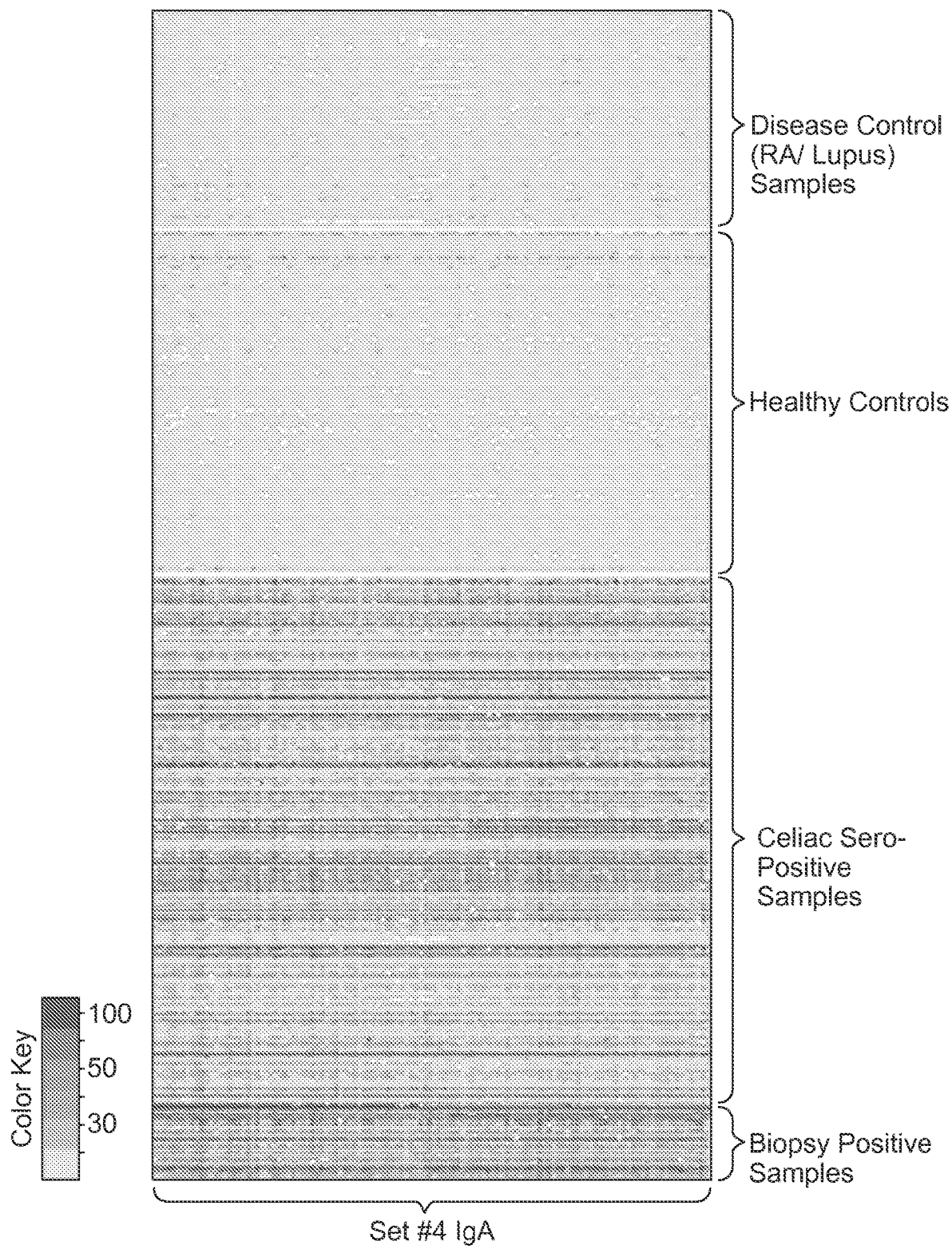
Figure 10C:
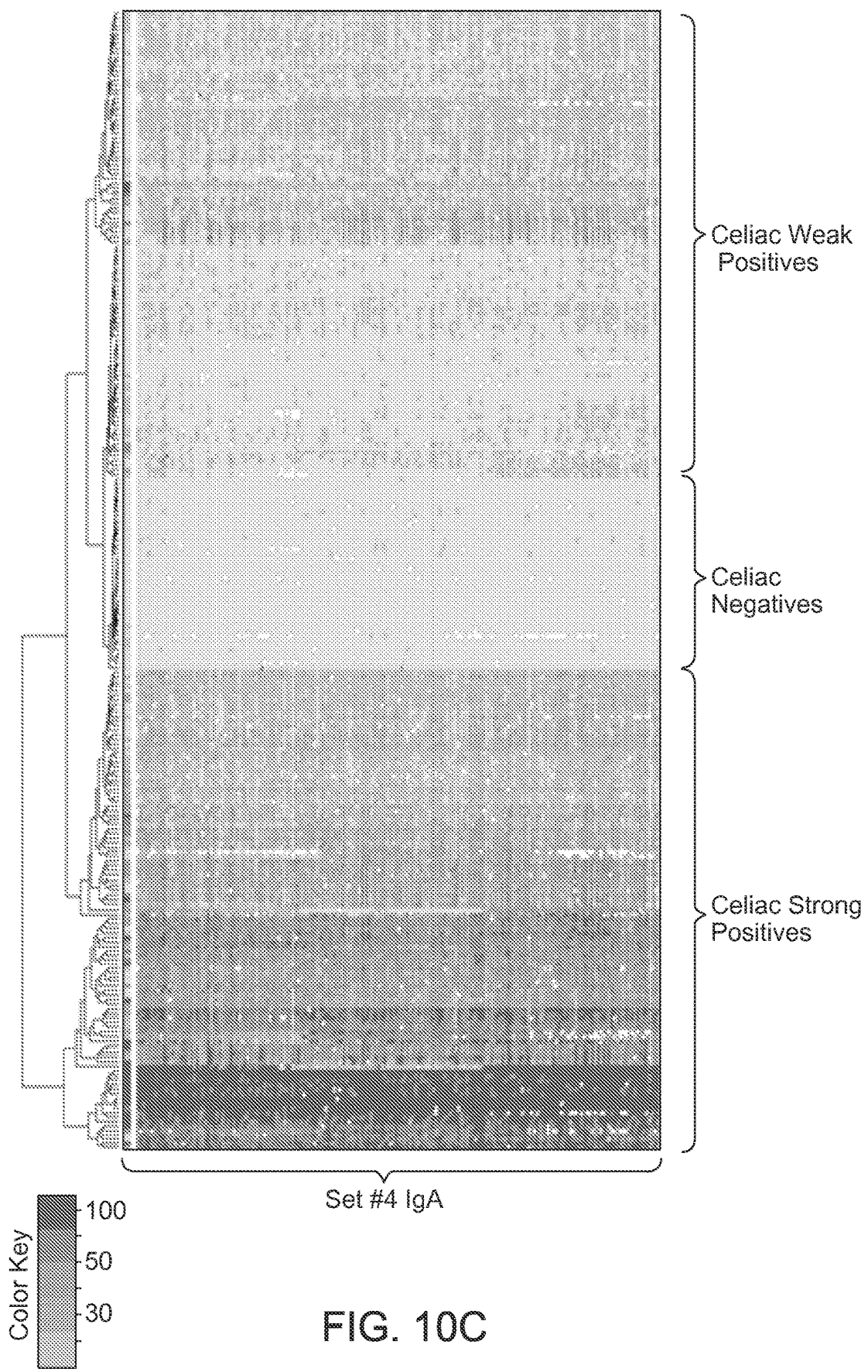

To validate the discriminative power of the novel peptides (SEQ ID NOS: 1-127) from the training cohort, sera from a population cohort of 1896 subjects were assayed in a blinded test. This cohort composed of 306 subjects with CDA and 1590 controls, who were tested with the current standard CD serology testing. CDA was defined with positivity to both tissue transglutaminase (tTG) IgA and endomysial antibodies (EMA), with a high predictive value for biopsy proven celiac disease. Of these 306 subjects (CDA), 33 individuals were subsequently diagnosed with CD during their follow up. The two novel synthetic peptides sets #3 and #4 comprising discontinuous gliadin sequences showed a high accuracy for distinguishing CDA cases from controls, achieving 99% sensitivity and 100% specificity (Table 6). In addition, CDA cases could be separated to a lower or a higher reactivity group based on antibody binding intensity, as illustrated in FIGS. 10A-10C, and the sera of all 33

3-dimensional structures that would not have affinity for the T-cell receptor when presented by antigen-presenting cells (APCs). Since immune response typifying CD may require proteins from wheat and like grains, the discovery power of this novel ultra through put platform was used to systematically search both linear continuous as well as discontinuous peptides derived from all known proteins. A set of novel epitopes was identified with a novel method with the set composed of discontinuous peptide sequences derived of the deamidated gliadin, that were recognized by the circulating antibodies found in the sera of patients with CD, showing high sensitivity and specificity for discriminating CD from controls. These 9-mer to 15-mer sequences, which are different from the known 33-mer gliadin sequence[21], represent novel and heretofore unidentified B cell epitopes of gliadin. The identified peptides were subjected to a rigorous test of significance and predictive values by running a validation cohort from a community based samples that played no part in their selection with certain seropositive and other biopsy positive samples. Validation showed high accuracy of disease diagnosis and severity detection. For example, two sero-negative samples from the training cohort and six sero-negative samples were captured from the validation cohort increasing the sensitivity and specificity to 99% and 100% respectively. Furthermore, specific sequences were identified that allowed successful subgrouping according to severity, which is not possible by conventional antibodies.

The biomarker discovery via the platform of highly efficient mass manufacturing of ultra high density peptide microarrays presented here provides an efficient method to determine novel epitopes through mapping of antigens and combining the immunopotent sequences with random peptides. Peptide miroarrays based on 2.1 million of 9-mer to 15-mer peptides, each overlapping with three or six amino acids, were used to cover the immunogenic proteins with very high density maximizing the ability to identify informative peptides, and showed the effectiveness and utility of this technology on identification of unknown but novel epitopes that are recognized by patients with autoimmune disease. An advantage of this method includes the development of more precise diagnostic tests that can be incorporated into panels of testing for autoimmune diseases, including celiac disease. Moreover, the contribution of the individual amino acids of the antigen were evaluated for antibody binding, by designing microarrays of peptides containing lateral shifts of one amino acid, achieving higher mapping resolution for the target antigen.

All previous photolithography based microarray in situ synthesis methods[5,22-24] are based on individually addressable deprotection step and then monomers coupling to those selective deprotected sites. The methods described herein involve generalized de-protection followed by selective activation, providing two advantages: 1) a far higher fidelity of peptide synthesis, and 2) a greatly reduced time requirement for each step. This permits a significantly higher number of steps, as many as 400, in the synthesis of a peptide microarray, leading with a very low yield loss. In some embodiment, the combination of high-fidelity and shorter reaction times result in a much higher yield and the ability to generate a large number of chips. Additional advantages include the cost savings due to high-fidelity that may be required for diagnostic testing. The method described herein utilizes the state of the art 248 nm semiconductor lithography semiconductor tools on a proven 300 mm silicon wafer platform. In some embodiments, a very high microarray density enables not only the molecular diversity needed for biomarker discovery but also to enable large scale biomarker validation. The method is well suited for mass manufacturing for routine diagnostics since the chips size can scale down to $0.5 \times 0.5$ mm$^2$ fit any diagnostics well plate format, like 96, 384, 1396. This enables smaller size samples to be used for routine diagnostics.

The methods disclosed herein represent non-invasive, broadly availabile, low cost, and versatile methods by using the disclosed peptide microarrays, which are well-suited for routine health care diagnostic purposes and for providing a powerful novel tool for biomarker discovery.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

Finally, it should be noted that the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention.

REFERENCES

1. Kijanka G, Murphy D. Protein arrays as tools for serum autoantibody marker discovery in cancer. J Proteomics 2009; 72:936-44.
2. Ballew J T, Murray J A, Collin P, et al. Antibody biomarker discovery through in vitro directed evolution of consensus recognition epitopes. Proc Natl Acad Sci USA 2013; 110:19330-5.
3. Lewis J D. The utility of biomarkers in the diagnosis and therapy of inflammatory bowel disease. Gastroenterology 2011; 140:1817-1826 e2.
4. Solier C, Langen H. Antibody-based proteomics and biomarker research—current status and limitations. Proteomics 2014; 14:774-83.
5. Price J V, Tangsombatvisit S, Xu G, et al. On silico peptide microarrays for high-resolution mapping of antibody epitopes and diverse protein-protein interactions. Nat Med 2012; 18:1434-40.
6. Beyer M, Nesterov A, Block I, et al. Combinatorial synthesis of peptide arrays onto a microchip. Science 2007; 318:1888.
7. Dam C E, Houen G, Hansen P R, et al. Identification and fine mapping of a linear B cell epitope of human vimentin. Scand J Clin Lab Invest 2014.
8. Singh-Gasson S, Green R D, Yue Y, et al. Maskless fabrication of light-directed oligonucleotide microarrays using a digital micromirror array. Nat Biotechnol 1999; 17:974-8.
9. Buus S, Rockberg J, Forsstrom B, et al. High-resolution mapping of linear antibody epitopes using ultrahigh-density peptide microarrays. Mol Cell Proteomics 2012; 11:1790-800.
10. Rubio-Tapia A, Hill I D, Kelly C P, et al. ACG clinical guidelines: diagnosis and management of celiac disease. Am J Gastroenterol 2013; 108:656-76; quiz 677.
11. Norris J M, Barriga K, Hoffenberg E J, et al. Risk of celiac disease autoimmunity and timing of gluten introduction in the diet of infants at increased risk of disease. JAMA 2005; 293:2343-51.
12. Osorio C, Wen N, Gemini R, et al. Targeted modification of wheat grain protein to reduce the content of celiac causing epitopes. Funct Integr Genomics 2012; 12:417-38.
13. Gianfrani C, Troncone R, Mugione P, et al. Celiac disease association with CD8+ T cell responses: identification of a novel gliadin-derived HLA-A2-restricted epitope. J Immunol 2003; 170:2719-26.
14. Zintzaras E, Germenis A E. Performance of antibodies against tissue transglutaminase for the diagnosis of celiac disease: meta-analysis. Clin Vaccine Immunol 2006; 13:187-92.
15. Osman A A, Gunnel T, Dietl A, et al. B cell epitopes of gliadin. Clin Exp Immunol 2000; 121:248-54.
16. ten Dam M, Van De Wal Y, Mearin M L, et al. Anti-alpha-gliadin antibodies (AGA) in the serum of coeliac children and controls recognize an identical collection of linear epitopes of alpha-gliadin. Clin Exp Immunol 1998; 114:189-95.

17. Husby S, Koletzko S, Korponay-Szabo I R, et al. European Society for Pediatric Gastroenterology, Hepatology, and Nutrition guidelines for the diagnosis of coeliac disease. J Pediatr Gastroenterol Nutr 2012; 54:136-60.
18. Kaukinen K, Collin P, Laurila K, et al. Resurrection of gliadin antibodies in coeliac disease. Deamidated gliadin peptide antibody test provides additional diagnostic benefit. Scand J Gastroenterol 2007; 42:1428-33.
19. Rubio-Tapia A, Kyle R A, Kaplan E L, et al. Increased prevalence and mortality in undiagnosed celiac disease. Gastroenterology 2009; 137:88-93.
20. Breiman L Random Forests. Machine Learning 2001; 45:5-32.
21. Aleanzi M, Demonte A M, Esper C, et al. Celiac disease: antibody recognition against native and selectively deamidated gliadin peptides. Clin Chem 2001; 47:2023-8.
22. Fodor S P, Read J L, Pirrung M C, et al. Light-directed, spatially addressable parallel chemical synthesis. Science 1991; 251:767-73.
23. Gao X, Zhou X, Gulari E. Light directed massively parallel on-chip synthesis of peptide arrays with t-Boc chemistry. Proteomics 2003; 3:2135-41.
24. Pawloski A R, McGall G, Kuimelis R G, et al. Photolithographic synthesis of high-density DNA probe arrays: Challenges and opportunities. J Vac Sci Technol 2007; B 25:2537-2546.

What is claimed is:

1. An array of features attached to a surface at positionally-defined locations, said features comprising at least one engineered polypeptide chain comprising at least two discontinuous epitope sequences from a bioactive polypeptide that generates an immune response in subject having celiac disease, wherein each of said at least two discontinuous epitopes consists of 3 amino acids with at least 20% sensitivity for binding to an antibody in a celiac positive sample, wherein said engineered polypeptide chain further comprises at least one randomly generated polypeptide sequence between at least two of the discontinuous epitope sequences, and wherein said engineered polypeptide chain is from 7 to 15 amino acids in length.

2. The array of claim 1, wherein said bioactive polypeptide is selected from the group consisting of: alpha gliadin, beta gliadin, gamma gliadin, omega gliadin, and other wheat-related proteins or peptides.

3. The array of claim 1, wherein said features comprising at least one engineered polypeptide comprise at least 1 sequence selected from the group consisting of SEQ ID NOS: 1-127.

4. The array of claim 1, wherein said features are 12 amino acids in length.

5. The array of claim 1, wherein said features attached to the surface of the array are configured to have at least 90% sensitivity and 90% specificity for detection of celiac disorder after contact of said features with a sample from a subject suspected of having celiac disorder.

6. The array of claim 1 further comprising: at least 10,000 features, each feature is attached to a surface of the array at a different positionally-defined location, the positionally defined location of each feature corresponds to a positionally-defined location of a pillar, wherein the top surface of each pillar is at least 1 µm$^2$ in size.

7. The array of claim 6, wherein each feature comprises a different engineered peptide chain compared to the other features, each feature comprises at least 500 identical full-length peptide chains, and wherein each identical full-length peptide chain has an engineered full-length of at least 7 amino acids in length, and the purity of each feature with regards to the fraction of full-length engineered peptide chains is a fraction F of the full-length engineered peptide chains of each feature having a engineered sequence and a engineered full-length sequence length N being characterized by $F=10^{(N+1) \cdot \log(E/100\%)}$ with an average coupling efficiency E of at least 98.5% for coupling each amino acid of the engineered sequence, and the sequence length N being at least 7 amino acids in length, the fraction of the less than full-length engineered peptide chains equaling (1−F).

8. The array of claim 6, wherein the surface comprises a substrate, the substrate comprising: a planar layer having an upper surface and a lower surface, and a plurality of pillars operatively coupled to the layer in the positionally-defined locations, and wherein each pillar has a planar surface extended from the layer, wherein the distance between the surface of each pillar and the upper surface of the layer is between 1,000-5,000 angstroms, and wherein the plurality of pillars are present at a density of greater than 10,000/cm$^2$.

9. A substantially purified and/or recombinant peptide comprising an amino acid sequence selected from the group consisting of SEQ ID NOS: 1-127.

* * * * *

UNITED STATES PATENT AND TRADEMARK OFFICE
CERTIFICATE OF CORRECTION

PATENT NO. : 10,900,964 B2
APPLICATION NO. : 15/510223
DATED : January 26, 2021
INVENTOR(S) : John J. Rajasekaran et al.

It is certified that error appears in the above-identified patent and that said Letters Patent is hereby corrected as shown below:

In the Claims

In Column 116, Lines 20-21, Claim 7, replace "a engineered sequence and a engineered" with --an engineered sequence and an engineered--.

Signed and Sealed this
Seventeenth Day of January, 2023

Katherine Kelly Vidal
*Director of the United States Patent and Trademark Office*

```
                          SEQUENCE LISTING

<160> NUMBER OF SEQ ID NOS: 129

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1

Arg Arg Gly Gln Pro Phe Trp Gln Pro Glu Leu Thr
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 2

Val Val Asp Pro Glu Gln Pro Gln Gln Asp Cys Thr
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 3

Gly Gln Pro Phe Gln Pro Glu Gln Pro Trp Leu Thr
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4

Gly Gln Pro Phe Trp Leu Thr Gln Pro Glu Gln Pro
1               5                   10
```

```
<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Thr Ala Thr Val Val Asp Pro Glu Gln Pro Gln Gln
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Tyr Pro Glu Gln Pro Glu Gln Pro Gly Ser Ser Glu
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Arg Ala Asn His Leu Asn Gln Pro Glu Gln Pro Phe
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

Gln Pro Phe Trp Gln Pro Glu Gln Pro Phe Leu Thr
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9

Leu His Phe Pro Glu Gln Pro Glu Gly Arg Asn Tyr
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide
```

```
<400> SEQUENCE: 10

Asn Gln Pro Glu Gln Pro Phe Pro Leu Pro Val Ala
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 11

Arg Gly Gln Pro Phe Gln Pro Glu Gln Pro Phe Trp
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 12

Thr Arg Pro Asp Leu Glu Gln Pro Phe Pro Gln Pro
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 13

His Phe Pro Glu Gln Pro Glu Gly Arg Asn Tyr Glu
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 14

Val Val Arg Arg Gly Gln Pro Phe Trp Gln Pro Glu
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 15

Gly Gln Pro Phe Trp Leu Gln Pro Glu Gln Pro Thr
1               5                   10

<210> SEQ ID NO 16
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      Peptide

<400> SEQUENCE: 16

Arg Gly Gln Pro Phe Trp Gln Pro Glu Leu Thr Leu
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 17

Arg Gly Gln Pro Phe Trp Leu Thr Leu Gln Pro Glu
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 18

Arg Gly Gln Pro Phe Trp Leu Gln Pro Glu Thr Leu
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 19

Phe Pro Glu Gln Pro Glu Gly Arg Asn Tyr Glu Ala
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 20

Leu Val Val Asn Phe Pro Glu Gln Pro Glu Ser Asp
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 21

Glu Gln Pro Glu Gln Pro Phe Ser Asn Leu Ile Lys
1               5                   10
```

-continued

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 22

Val Arg Arg Gly Gln Pro Phe Gln Pro Glu Trp Leu
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 23

Gly Gln Pro Phe Trp Leu Thr Gln Pro Glu Gln Leu
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 24

Arg Arg Gly Gln Pro Phe Trp Leu Gln Pro Glu Thr
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 25

Phe Pro Glu Gln Pro Glu Asp Gly Ile Leu Asp Ile
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 26

Val Arg Arg Gly Gln Pro Phe Gln Pro Glu Gln Pro
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide -continued

```
<400> SEQUENCE: 27

Gly Gln Pro Phe Trp Leu Gln Pro Glu Gln Pro Phe
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 28

Gly Gln Pro Phe Trp Leu Thr Leu Gln Pro Glu Gln
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 29

Glu Asn Pro Glu Gln Pro Glu Gln Pro Phe Ile Lys
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 30

Arg Gly Gln Pro Phe Trp Gln Pro Glu Gln Leu Thr
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 31

His Lys Leu Val Val Asn Phe Pro Glu Gln Pro Glu
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 32

Arg Gly Gln Pro Phe Trp Leu Thr Gln Pro Glu Gln
1               5                   10

<210> SEQ ID NO 33
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      Peptide

<400> SEQUENCE: 33

Thr Gln Pro Glu Gln Pro Phe Val Glu Ile Pro Asp
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 34

Met Asn Met Gln Pro Glu Gln Pro Phe Gly Ser Asp
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 35

Thr Tyr Lys Tyr Pro Glu Gln Pro Glu Gln Pro Gly
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 36

Trp Asn Phe Gly Gln Phe Pro Glu Gln Pro Glu Asp
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 37

Gly Gln Pro Phe Trp Leu Gln Pro Glu Thr Leu His
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 38

Leu Thr Leu His Phe Pro Glu Gln Pro Glu Gly Arg
1               5                   10
```

```
<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 39

Asn Phe Pro Glu Gln Pro Glu Ser Asp Lys Leu Lys
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 40

Val Asn Phe Pro Glu Gln Pro Glu Ser Asp Lys Leu
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 41

Thr Leu His Phe Pro Glu Gln Pro Glu Gly Arg Asn
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 42

Leu Tyr Leu Glu Asn Pro Glu Gln Pro Glu Gln Pro
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 43

Ala Val Glu Glu Gln Pro Glu Gln Pro Gly Asp Trp
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide
```

```
<400> SEQUENCE: 44

Gln Phe Pro Glu Gln Pro Glu Asp Gly Ile Leu Asp
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 45

Gln Pro Phe Trp Leu Gln Pro Glu Gln Pro Thr Leu
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 46

Phe Pro Glu Gln Pro Glu Ser Asp Lys Leu Lys Ala
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 47

Gly Gln Pro Phe Gln Pro Glu Gln Pro Phe Trp Leu
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 48

Lys Ala Arg Phe Pro Gln Pro Glu Gln Leu Arg Asp
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 49

Pro Glu Gln Pro Glu Gln Pro Ile Lys Ile Arg Ile
1               5                   10

<210> SEQ ID NO 50
<211> LENGTH: 12
<212> TYPE: PRT
```

<213> ORGANISM: Artificial Sequence
<220> FEATURE:
<223> OTHER INFORMATION: Description of Artificial Sequence: Synthetic
      Peptide

<400> SEQUENCE: 50

Ala Leu Asp Pro Thr Pro Gln Pro Glu Gln Pro Phe
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 51

Leu Val Val Arg Arg Gly Gln Pro Phe Gln Pro Glu
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 52

Phe Ala Ala Val Ala Gln Pro Glu Gln Pro Phe Cys
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 53

Gly Gln Pro Phe Trp Leu Gln Pro Glu Gln Thr Leu
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 54

Tyr Val Leu Thr Pro Glu Gln Pro Phe Pro Gln Gln
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 55

Lys Ala Arg Phe Pro Gln Pro Glu Gln Pro Phe Leu
1               5                   10

```
<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 56

Gln Pro Phe Trp Leu Thr Leu His Phe Gln Pro Glu
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 57

Glu Gln Pro Phe Pro Gln Pro Phe Trp Leu Thr Leu
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 58

Arg Arg Gly Gln Pro Phe Trp Gln Pro Glu Gln Pro
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 59

Arg Gly Gln Pro Phe Gln Pro Glu Trp Leu Thr Leu
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 60

Gln Glu Gln Pro Glu Gln Pro Ala Gly Thr Lys Ala
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide
```

```
<400> SEQUENCE: 61

Ser Gln Pro Glu Gln Pro Phe Gly Met Val Asn Cys
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 62

Val Arg Arg Gly Pro Glu Gln Pro Phe Pro Gln Pro
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 63

Gly Gln Pro Phe Trp Gln Pro Glu Leu Thr Leu His
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 64

Leu Glu Gln Pro Glu Gln Pro Phe Ser Glu Lys Ser
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 65

Val Arg Arg Gly Gln Pro Phe Trp Leu Gln Pro Glu
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 66

Gln Pro Phe Gln Pro Glu Gln Pro Trp Leu Thr Leu
1               5                   10

<210> SEQ ID NO 67
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      Peptide

<400> SEQUENCE: 67

Phe Gly Gln Phe Pro Glu Gln Pro Glu Asp Gly Ile
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 68

Val Arg Arg Gly Gln Pro Phe Trp Gln Pro Glu Leu
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 69

Arg Asp Leu Tyr Leu Glu Gln Pro Glu Gln Pro Phe
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 70

Gln Pro Phe Gln Pro Glu Gln Trp Leu Thr Leu His
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 71

Asn Pro Glu Gln Pro Glu Gln Pro Ile Lys Ile Arg
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 72

Val Arg Arg Gly Gln Pro Phe Gln Pro Glu Gln Trp
1               5                   10
```

```
<210> SEQ ID NO 73
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 73

Tyr Lys Tyr Pro Glu Gln Pro Glu Gln Pro Phe Gly
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 74

Gly Pro Glu Gln Pro Phe Pro Gln Pro Phe Trp Leu
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 75

Gln Pro Phe Trp Leu Gln Pro Glu Gln Thr Leu His
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 76

Val Val Asp Trp Ile Gln Pro Glu Gln Pro Gln Gln
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 77

Pro Glu Gln Pro Phe Pro Gln Gln Asp Asp Gly Ser
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide
```

```
<400> SEQUENCE: 78

Arg Arg Gly Gln Pro Phe Gln Pro Glu Gln Trp Leu
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 79

Asn Gly Ile Leu Gly Pro Glu Gln Pro Glu Gln Cys
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 80

Val Val Asn Phe Pro Glu Gln Pro Glu Ser Asp Lys
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 81

Gly Gln Pro Phe Gln Pro Glu Trp Leu Thr Leu His
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 82

Gln Pro Glu Gln Pro Phe Val Asp Gln Gln Asp Cys
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 83

His Thr Tyr Lys Tyr Pro Glu Gln Pro Glu Gln Pro
1               5                   10

<210> SEQ ID NO 84
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      Peptide

<400> SEQUENCE: 84

Arg Arg Gly Gln Pro Phe Gln Pro Glu Trp Leu Thr
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 85

Gly Gln Pro Phe Trp Leu Thr Gln Pro Glu Leu His
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 86

Glu Asn Pro Glu Gln Pro Glu Gln Ile Lys Ile Arg
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 87

Gly Gln Pro Phe Trp Gln Pro Glu Gln Pro Leu Thr
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 88

Gly Gln Pro Phe Trp Leu Thr Leu Gln Pro Glu His
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 89

Trp Leu Thr Leu His Phe Pro Glu Gln Pro Glu Gly
1               5                   10
```

```
<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 90

Gln Pro Phe Trp Leu Thr Leu His Gln Pro Glu Gln
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 91

Arg Gly Gln Pro Phe Trp Gln Pro Glu Gln Pro Phe
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 92

Gln Pro Glu Gln Pro Gln Gln Asp Cys Thr Leu Ser
1               5                   10

<210> SEQ ID NO 93
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 93

Arg Arg Gly Glu Gln Pro Phe Pro Gln Pro Phe Trp
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 94

Val Leu Thr Gln Pro Glu Gln Pro Gln Gln Gly Phe
1               5                   10

<210> SEQ ID NO 95
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide
```

```
<400> SEQUENCE: 95

Gln Pro Phe Trp Leu Gln Pro Glu Gln Pro Phe Thr
1               5                   10

<210> SEQ ID NO 96
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 96

Gln Pro Phe Trp Gln Pro Glu Leu Thr Leu His Phe
1               5                   10

<210> SEQ ID NO 97
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 97

Phe Trp Leu Thr Leu His Phe Pro Glu Gln Pro Glu
1               5                   10

<210> SEQ ID NO 98
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 98

Arg Arg Gly Gln Pro Phe Trp Leu Thr Gln Pro Glu
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 99

Thr Tyr Lys Tyr Pro Glu Gln Pro Glu Gln Gly Ser
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 100

Gly Ile Leu Gly Pro Glu Gln Pro Glu Gln Pro Phe
1               5                   10

<210> SEQ ID NO 101
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      Peptide

<400> SEQUENCE: 101

Asp Leu Glu Gln Pro Phe Pro Gln Pro Gly Tyr Glu
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 102

Gly Gln Pro Phe Trp Gln Pro Glu Gln Pro Phe Leu
1               5                   10

<210> SEQ ID NO 103
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 103

Gly Gln Phe Pro Glu Gln Pro Glu Asp Gly Ile Leu
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 104

Arg Gly Gln Pro Phe Trp Leu Gln Pro Glu Gln Thr
1               5                   10

<210> SEQ ID NO 105
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 105

Asp Trp Ile Pro Glu Gln Pro Phe Pro Gln Gln Asp
1               5                   10

<210> SEQ ID NO 106
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 106

Arg Gly Gln Pro Phe Trp Leu Gln Pro Glu Gln Pro
1               5                   10
```

```
<210> SEQ ID NO 107
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 107

Lys Leu Val Val Asn Phe Pro Glu Gln Pro Glu Ser
1               5                   10

<210> SEQ ID NO 108
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 108

Asn Phe Gly Gln Phe Pro Glu Gln Pro Glu Asp Gly
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 109

Arg Phe Pro Gln Pro Glu Gln Pro Leu Arg Asp Ala
1               5                   10

<210> SEQ ID NO 110
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 110

Tyr Lys Tyr Pro Glu Gln Pro Glu Gln Gly Ser Ser
1               5                   10

<210> SEQ ID NO 111
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 111

Leu Asn Leu Glu Gln Pro Glu Gln Pro Phe Pro Phe
1               5                   10

<210> SEQ ID NO 112
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide
```

```
<400> SEQUENCE: 112

Leu Gly Pro Glu Gln Pro Glu Gln Pro Phe Cys Gly
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 113

Ala Gly Thr Lys Ala Arg Phe Pro Gln Pro Glu Gln
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 114

Tyr Lys Tyr Pro Glu Gln Pro Glu Gln Pro Gly Ser
1               5                   10

<210> SEQ ID NO 115
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 115

Lys Arg Gln Pro Glu Gln Pro Phe Lys Leu Val Ala
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 116

Arg Arg Gly Pro Glu Gln Pro Phe Pro Gln Pro Phe
1               5                   10

<210> SEQ ID NO 117
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 117

Gly Ser Ser Glu Glu Arg Glu Gln Pro Glu Gln Pro
1               5                   10

<210> SEQ ID NO 118
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      Peptide

<400> SEQUENCE: 118

Gln Pro Phe Gln Pro Glu Gln Pro Phe Trp Leu Thr
1               5                   10

<210> SEQ ID NO 119
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 119

Pro Glu Gln Pro Glu Gln Pro Gly Ser Ser Glu Glu
1               5                   10

<210> SEQ ID NO 120
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 120

Val Asp Trp Ile Gln Pro Glu Gln Pro Gln Gln Asp
1               5                   10

<210> SEQ ID NO 121
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 121

Leu Glu Asn Pro Glu Gln Pro Glu Gln Ile Lys Ile
1               5                   10

<210> SEQ ID NO 122
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 122

Gly Thr Lys Ala Arg Phe Pro Gln Pro Glu Gln Leu
1               5                   10

<210> SEQ ID NO 123
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 123

Asn Pro Glu Gln Pro Glu Gln Pro Phe Ile Lys Ile
1               5                   10
```

```
<210> SEQ ID NO 124
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 124

Gln Pro Phe Trp Gln Pro Glu Gln Leu Thr Leu His
1               5                   10

<210> SEQ ID NO 125
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 125

Arg Gly Gln Pro Phe Trp Leu Thr Gln Pro Glu Leu
1               5                   10

<210> SEQ ID NO 126
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 126

Glu Gln Pro Glu Gln Pro Glu Val Lys Val Arg Met
1               5                   10

<210> SEQ ID NO 127
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 127

Val Arg Arg Gly Glu Gln Pro Phe Pro Gln Pro Phe
1               5                   10

<210> SEQ ID NO 128
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 128

Gln Glu Thr Phe Ser Asp Leu Trp Lys Leu
1               5                   10

<210> SEQ ID NO 129
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 129

Ala Arg Glu Leu His Pro Glu Tyr Tyr Lys Asp
1               5                   10